United States Patent [19]
De Lange et al.

[11] Patent Number: 6,020,166
[45] Date of Patent: Feb. 1, 2000

[54] NUCLEIC ACID ENCODING AN ALTERED TELOMERE REPEAT BINDING FACTOR 2

[75] Inventors: Titia De Lange, New York, N.Y.; Bas Van Steensel, Seattle, Wash.; Alessandro Bianchi, Genève, Switzerland

[73] Assignee: The Rockfeller University, New York, N.Y.

[21] Appl. No.: 09/273,378

[22] Filed: Mar. 22, 1999

Related U.S. Application Data

[60] Division of application No. 09/018,628, Feb. 4, 1998, Pat. No. 5,917,019, which is a continuation-in-part of application No. 08/800,264, Feb. 13, 1997, Pat. No. 5,859,183.

[51] Int. Cl.[7] ............................. C12P 21/02; C12N 1/00; C12N 5/10; C12N 15/12; C12N 15/63
[52] U.S. Cl. ................. 435/69.1; 435/243; 435/252.3; 435/320.1; 435/325; 435/410; 536/23.1; 536/23.5
[58] Field of Search .................................. 536/23.1, 23.5; 435/410, 320.1, 243, 252.3, 325, 69.1

[56] References Cited

U.S. PATENT DOCUMENTS 5,733,730  3/1998  de Lange ..................................... 435/6

OTHER PUBLICATIONS

Bilaud et al, 1996, Nucl Acids Res, 24:1294–303.
Conrad et al, 1990, Cell, 63:739–50.
Gilson et al, 1995, J Mol Biol, 231:293–310.
Hanish et al, 1994, Proc Natl Acad Sci USA, 91:8861–5.
Harley et al, 1992, Exp Gerontol, 27:375–82.
Hovring et al, 1994, J Biol Med, 296:17663–9.
Krauskopf et al, 1996, Nature, 383–354–7.
Kyrion et al, 1992, Mol Cell Biol, 12:5159–73.
Li et al, 1996, Gen Dev, 10:1310–26.
Lundblad et al, 1996, Cell, 87:369–75.
Lustig et al, 1990, Science, 250:549–53.
McEachern et al, 1995, Nature, 376:403–9.
Metcalfe et al, 1996, Nature Gen, 13:350–3.
Muller et al, 1994, J Struct Biol, 113:1–12.
Saukumar et al, 1994, Oncogene, 9:1279–87.
Sandell et al, 1993, Cell, 75:729–41.
Shore et al, 1994, Trends Gen, 10:408–12.
Singer et al, 1994, Science, 266:404–9.
Smith et al, 1997, Trends Gen, 13:21–6.
Vignais et al, 1989, J Biol Chem, 264:8463–6.
Yu et al, 1990, Nature, 344:126–132.
Zakian, 1995a, Sacharomyces telomers: function, structure and replication, Cold Spring Harbor Laboratory Press, Cold Spring Harbor, pp. 107–38.
Zhong et al, 1992, Mol Cell Biol, 13:4834–43.
Chong et al, 1995, Science, 270:1663–7.
Blasco et al, Cell, 91:25–34.
Zakian et al, Cell, 91:1–3.
Pandita et al, Cytogenet Cell Genet, 71:86–93.
Sprung et al, 379:177–84.
Bodner et al, 1998, Science, 279:349–52.
van Steensel et al, 1998, Cell, 92:401–13.
van Steensel and de Lange, 1997, Nature, 385:740–3.

*Primary Examiner*—Terry McKelvey
*Attorney, Agent, or Firm*—Klauber & Jackson

[57] ABSTRACT

The present invention provides an isolated altered vertebrate telomere repeat binding factor (A-TRFs). Also included are the corresponding nucleic acids that encode the A-TRFs of the present invention, as well as the heterodimers formed by the association of an A-TRF with a TRF. In addition, pharmaceutical compositions containing the A-TRFs for treatment of diseases such as ataxia telangiectasia are also included. Methods of making, purifying and using the A-TRFs of the present invention are described. In addition, drug screening assays to identify drugs that mimic and/or complement the effect of the A-TRFs are presented.

21 Claims, 24 Drawing Sheets

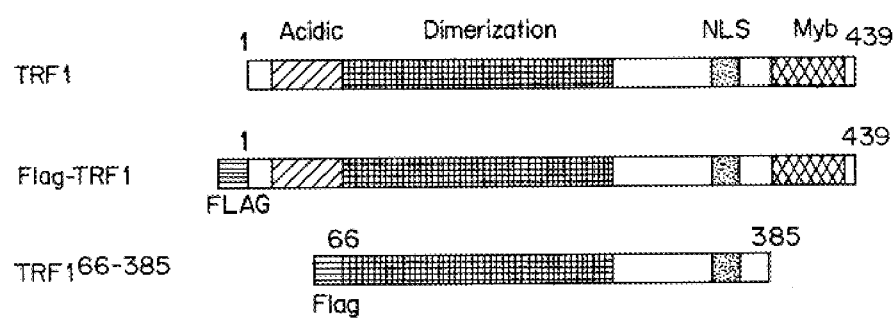
FIG. 1A
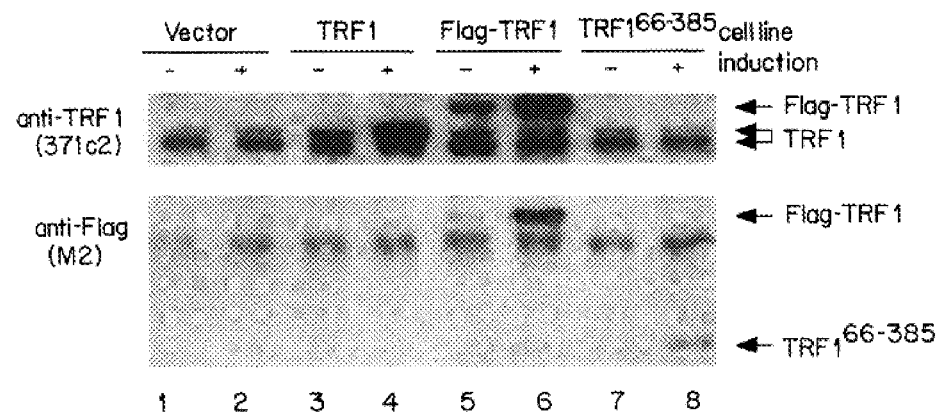
FIG. 1B
FIG. 1C

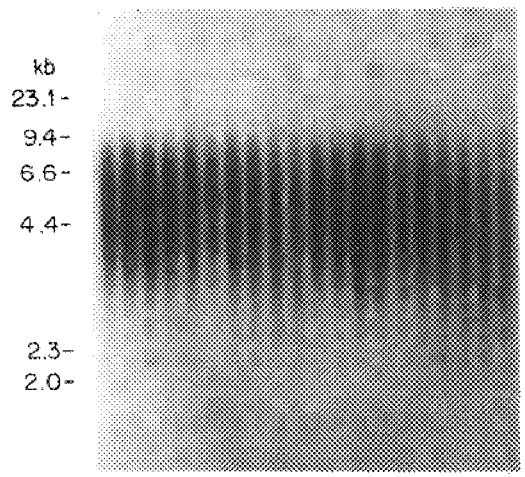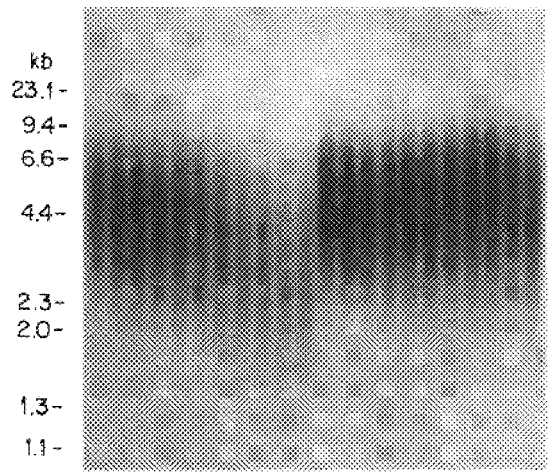
FIG.3A Vector
FIG.3B TRF 1

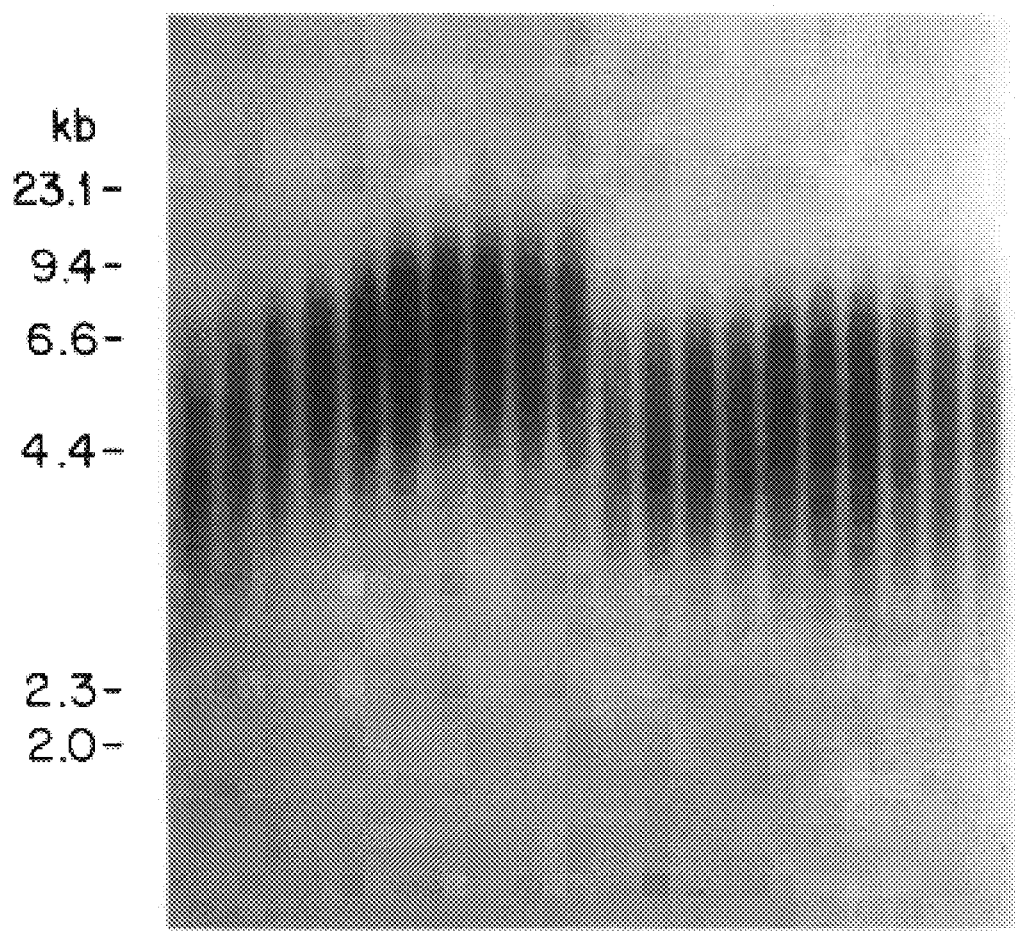

FIG. 7

| | GAD | Full length TRF1 | TRF1-Δ320-C |
|---|---|---|---|
| Full length TRF1 | 0 | 47 | 47 |
| 320-C | 0.8 | 142 | 159 |
| 263-C | 6.9 | 132 | n.d. |
| 210-C | 1.4 | 1.8 | n.d. |
| 68-C | 3.8 | 3.7 | n.d. |
| N-66 | 0 | 3.3 | n.d. |
| N-83 | 0 | 0 | n.d. |
| 66-263 | 11.1 | 164 | n.d. |

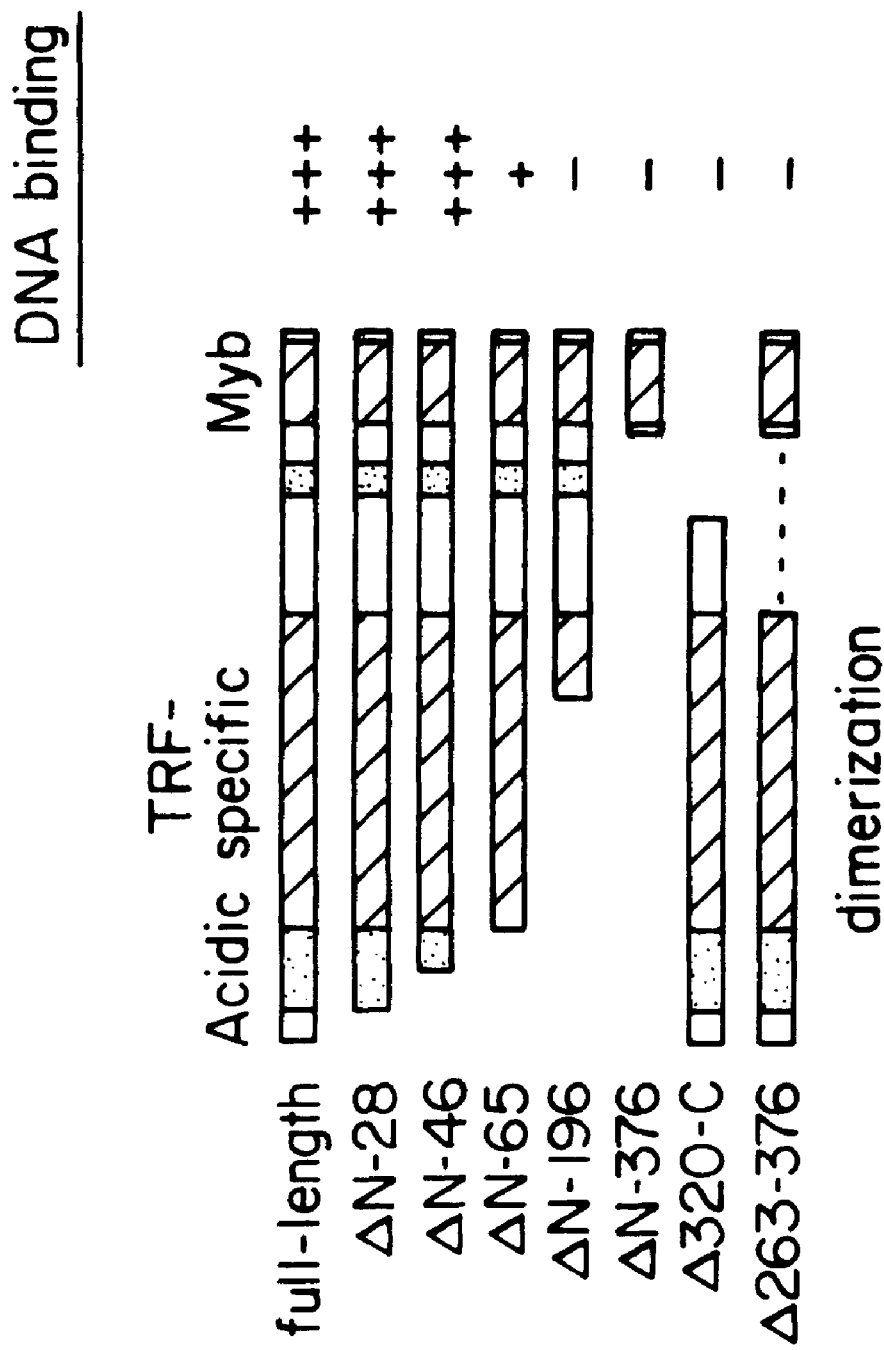

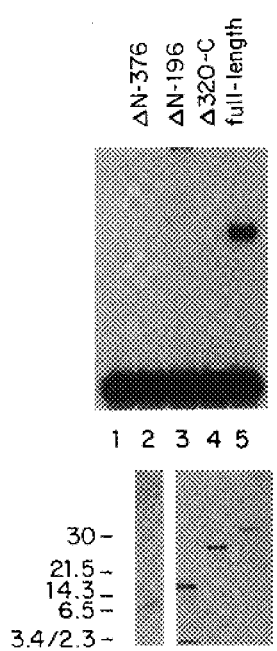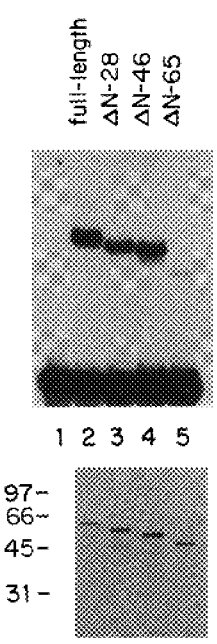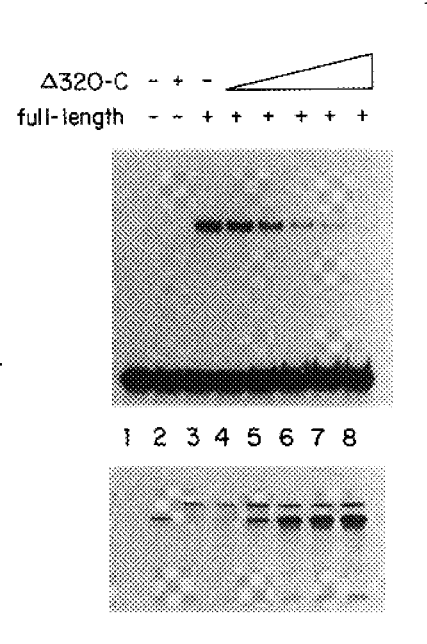

Permuted gel-shift probes

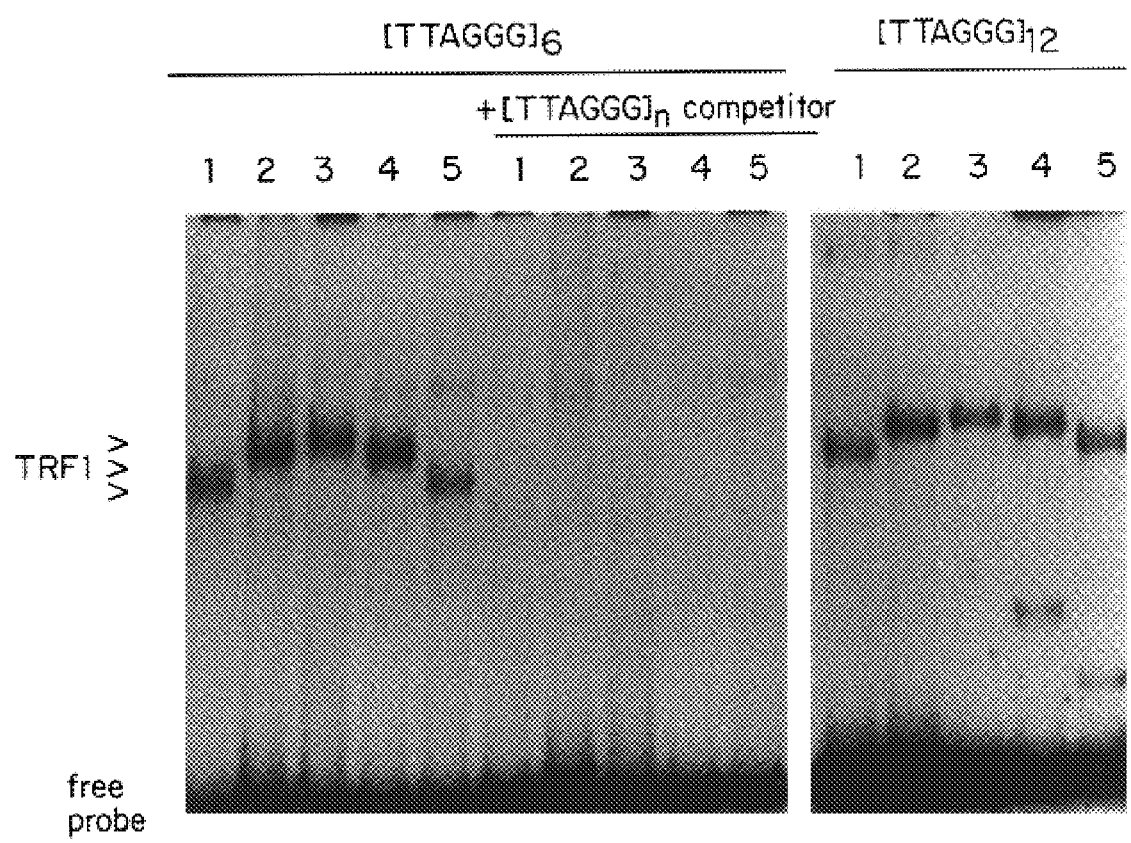

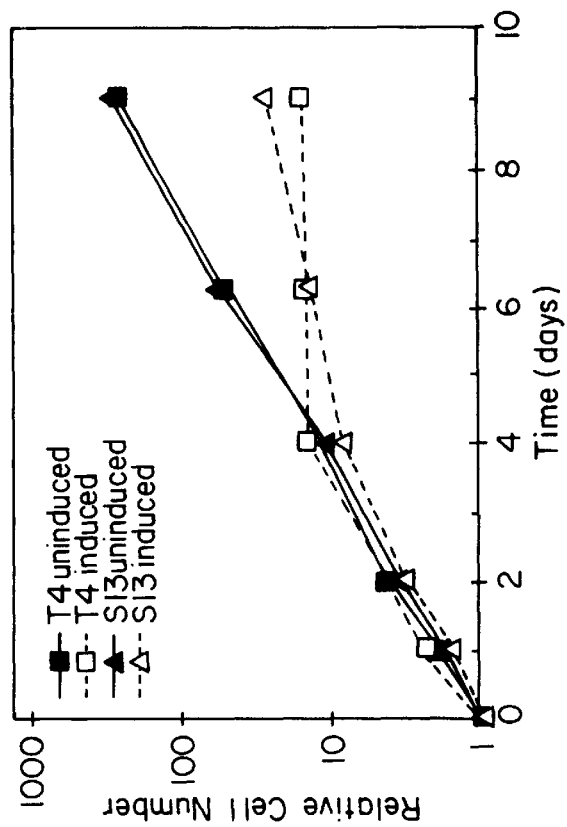
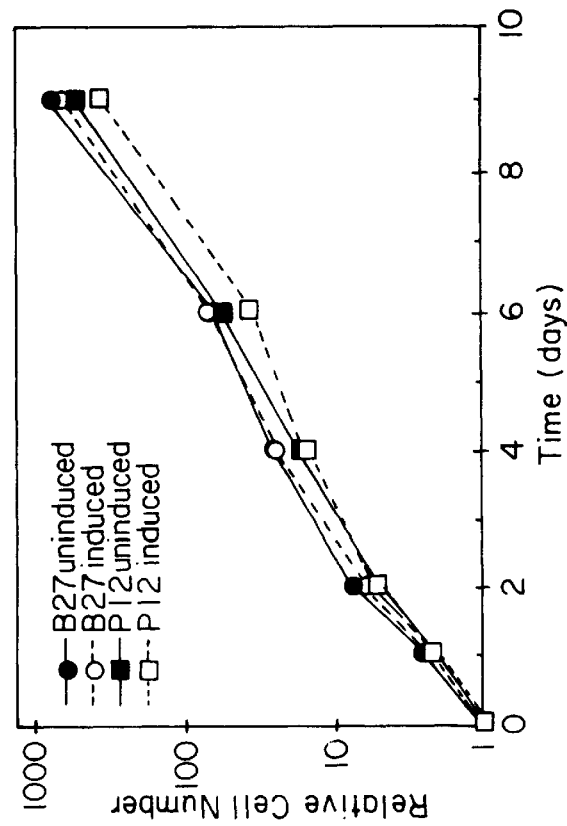
FIG. 14A
FIG. 14B

FIG.15A  FIG.15B  FIG.15C
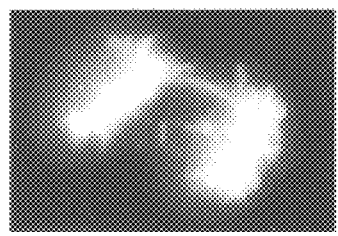
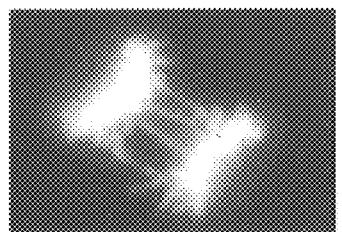
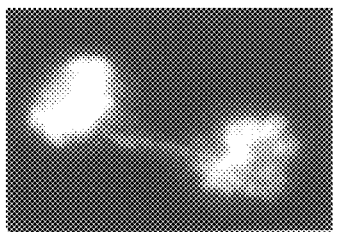
FIG.15D
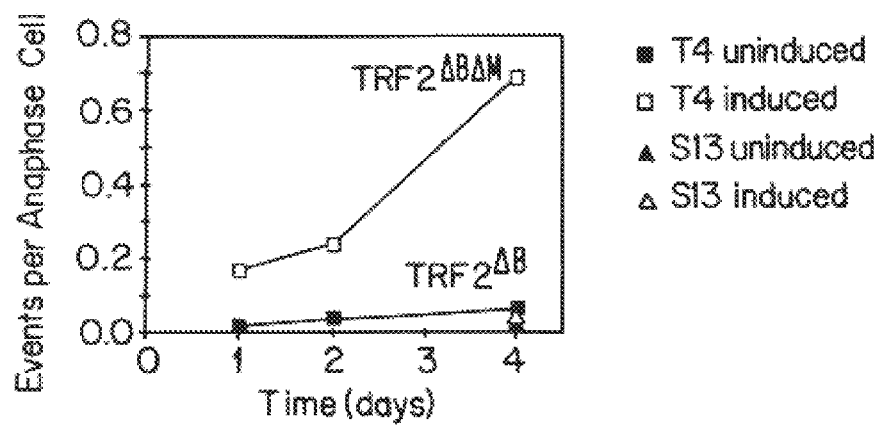
FIG.15E  FIG.15F
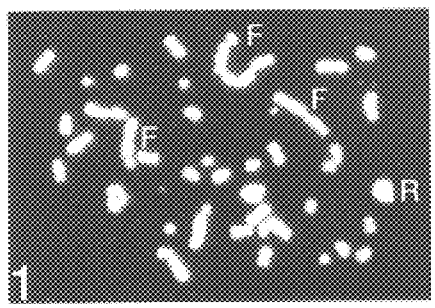
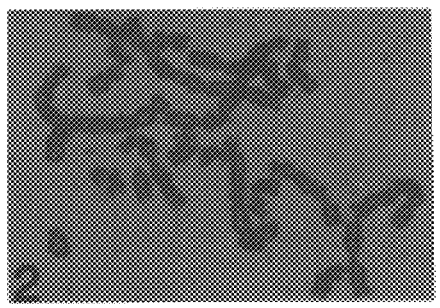
FIG.15G
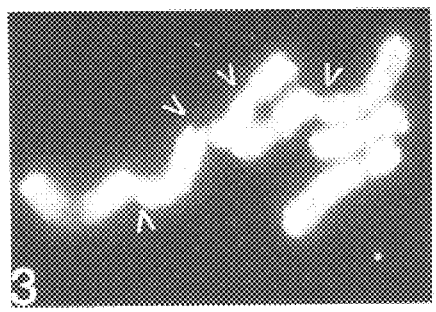

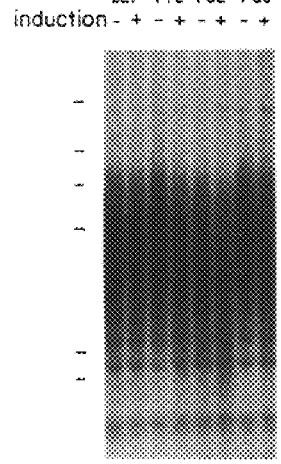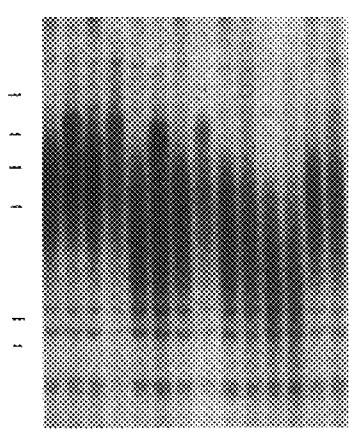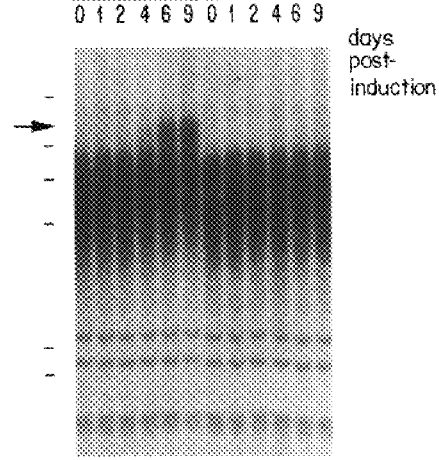
FIG. 16A
FIG. 16B
FIG. 16C

T4 ind. day 9 DNA
digested with Bal31
0 10 20 30 40 60 80 min

T19 ind. day 9 DNA
digested with Bal31

T4 ind. day 9 DNA
37 60 70 80 85 90 100 °C

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 1317 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
ATGGCGGAGG ATGTTTCCTC AGCGGCCCCG AGCCCGCGGC GGTGTGCGGA TGGTAGGGAT      60

GCCGACCCTA CTGAGGAGCA GATGGCAGAA ACAGAGAGAA ACGACGAGGA GCAGTTCGAA     120

TGCCAGGAAC TGCTCGAGTG CCAGGTGCAG GTGGGGGCCC CCGAGGAGGA GGAGGAGGAG     180

GAGGAGGACG CGGGCCTGGT GGCCGAGGCC GAGGCCGTGT GGCCGGGCTG GATGCTCGAT     240

TTCCTCTGCC TCTCTCTTTG CCGAGCTTTC CGCGACGGCC GCTCCGAGGA CTTCCGCAGG     300

ACCCGCAACA GCGCAGAGGC TATTATTCAT GGACTATCCA GTCTAACAGC TTGCCAGTTG     360

AGAACGATAT ACATATGTCA GTTTTTGACA AGAATTGCAG CAGGAAAAAC CCTTGATGCA     420

CAGTTTGAAA ATGATGAACG AATTACACCC TTGAATCAG CCCTGATGAT TTGGGGTTCA      480

ATTGAAAAGG AACATGACAA ACTTCATGAA GAAATACAGA ATTTAATTAA AATTCAGGCT     540

ATAGCTGTTT GTATGGAAAA TGGCAACTTT AAAGAAGCAG AAGAAGTCTT TGAAAGAATA     600
```

```
TTTGGTGATC CAAATTCTCA TATGCCTTTC AAAAGCAAAT TGCTTATGAT AATCTCTCAG      660

AAAGATACAT TTCATTCCTT TTTTCAACAC TTCAGCTACA ACCACATGAT GGAGAAAATT      720

AAGAGTTATG TGAATTATGT GCTAAGTGAA AAATCATCAA CCTTTCTAAT GAAGGCAGCG      780

GCAAAAGTAG TAGAAAGCAA AAGGACAAGA ACAATAACTT CTCAAGATAA ACCTAGTGGT      840

AATGATGTTG AAATGGAAAC TGAAGCTAAT TTGGATACAA GAAAAAGTGT TAGTGACAAA      900

CAGTCTGCGG TAACTGAATC CTCAGAGGGT ACAGTATCCT TATTGAGGTC TCACAAGAAT      960

CTTTTCTTAT CTAAGTTGCA ACATGGAACC CAGCAACAAG ACCTTAATAA GAAAGAAAGA     1020

AGAGTAGGAA CTCCTCAAAG TACAAAAAAG AAAAAGAAA GCAGAAGAGC CACTGAAAGC     1080

AGAATACCTG TTTCAAAGAG TCAGCCGGTA ACTCCTGAAA ACATCGAGC TAGAAAAAGA     1140

CAGGCATGGC TTTGGGAAGA AGACAAGAAT TTGAGATCTG GCGTGAGGAA ATATGGAGAG     1200

GGAAACTGGT CTAAAATACT GTTGCATTAT AAATTCAACA ACCGGACAAG TGTCATGTTA     1260

AAAGACAGAT GGAGGACCAT GAAGAAACTA AAACTGATTT CCTCAGACAG CGAAGAC       1317
```

(2) INFORMATION FOR SEQ ID NO:2:

(i) SEQUENCE CHARACTERISTICS:
        (A) LENGTH: 960 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:2:

```
CTGGTGGCCG AGGCCGAGGC CGTGTGGCCG GGCTGGATGC TCGATTTCCT CTGCCTCTCT       60

CTTTGCCGAG CTTTCCGCGA CGGCCGCTCC GAGGACTTCC GCAGGACCCG CAACAGCGCA      120

GAGGCTATTA TTCATGGACT ATCCAGTCTA ACAGCTTGCC AGTTGAGAAC GATATACATA      180

TGTCAGTTTT TGACAAGAAT TGCAGCAGGA AAAACCCTTG ATGCACAGTT TGAAAATGAT      240

GAACGAATTA CACCCTTGGA ATCAGCCCTG ATGATTTGGG GTTCAATTGA AAAGGAACAT      300

GACAAACTTC ATGAAGAAAT ACAGAATTTA ATTAAAATTC AGGCTATAGC TGTTTGTATG      360

GAAAATGGCA ACTTTAAAGA AGCAGAAGAA GTCTTTGAAA GAATATTTGG TGATCCAAAT      420

TCTCATATGC CTTTCAAAAG CAAATTGCTT ATGATAATCT CTCAGAAAGA TACATTTCAT      480

TCCTTTTTTC AACACTTCAG CTACAACCAC ATGATGGAGA AAATTAAGAG TTATGTGAAT      540

TATGTGCTAA GTGAAAAATC ATCAACCTTT CTAATGAAGG CAGCGGCAAA AGTAGTAGAA      600

AGCAAAAGGA CAAGAACAAT AACTTCTCAA GATAAACCTA GTGGTAATGA TGTTGAAATG      660

GAAACTGAAG CTAATTTGGA TACAAGAAAA AGTGTTAGTG ACAAACAGTC TGCGGTAACT      720

GAATCCTCAG AGGGTACAGT ATCCTTATTG AGGTCTCACA AGAATCTTTT CTTATCTAAG      780

TTGCAACATG GAACCCAGCA ACAAGACCTT AATAAGAAAG AAAGAAGAGT AGGAACTCCT      840

CAAAGTACAA AAAGAAAAA AGAAAGCAGA AGAGCCACTG AAAGCAGAAT ACCTGTTTCA      900

AAGAGTCAGC CGGTAACTCC TGAAAACAT CGAGCTAGAA AAAGACAGGC ATGGCTTTGG      960
```

(2) INFORMATION FOR SEQ ID NO:3:

(i) SEQUENCE CHARACTERISTICS:
        (A) LENGTH: 1311 base pairs
        (B) TYPE: nucleic acid
        (C) STRANDEDNESS: double (D) TOPOLOGY: linear (ii) MOLECULE TYPE: cDNA (iii) HYPOTHETICAL: NO (xi) SEQUENCE DESCRIPTION: SEQ ID NO:3:

| | | | | | |
|---|---|---|---|---|---|
| ATGGCGGAGG | ATGTTTCCTC | AGCGGCCCCG | AGCCCGCGGC | GGTGTGCGGA | TGGTAGGGAT | 60 |
| GCCGACCCTA | CTGAGGAGCA | GATGGCAGAA | ACAGAGAGAA | ACGACGAGGA | GCAGTTCGAA | 120 |
| TGCCAGGAAC | TGCTCGAGTG | CCAGGTGCAG | GTGGGGGCCC | CCGAGGAGGA | GGAGGAGGAG | 180 |
| GAGGAGGACG | CGGGCCTGGT | GGCCGAGGCC | GAGGCCGTGT | GGCCGGGCTG | GATGCTCGAT | 240 |
| TTCCTCTGCC | TCTCTCTTTG | CCGAGCTTTC | CGCGACGGCC | GCTCCGAGGA | CTTCCGCAGG | 300 |
| ACCCGCAACA | GCGCAGAGGC | TATTATTCAT | GGACTATCCA | GTCTAACAGC | TTGCCAGTTG | 360 |
| AGAACGATAT | ACATATGTCA | GTTTTTGACA | AGAATTGCAG | CAGGAAAAAC | CCTTGATGCA | 420 |
| CAGTTTGAAA | ATGATGAACG | AATTACACCC | TTGGAATCAG | CCCTGATGAT | TTGGGGTTCA | 480 |
| ATTGAAAAGG | AACATGACAA | ACTTCATGAA | GAAATACAGA | ATTTAATTAA | AATTCAGGCT | 540 |
| ATAGCTGTTT | GTATGGAAAA | TGGCAACTTT | AAAGAAGCAG | AAGAAGTCTT | TGAAAGAATA | 600 |
| TTTGGTGATC | CAAATTCTCA | TATGCCTTTC | AAAAGCAAAT | TGCTTATGAT | AATCTCTCAG | 660 |
| AAAGATACAT | TCATTCCTT | TTTTCAACAC | TTCAGCTACA | ACCACATGAT | GGAGAAAATT | 720 |
| AAGAGTTATG | TGAATTATGT | GCTAAGTGAA | AAATCATCAA | CCTTTCTAAT | GAAGGCAGCG | 780 |
| GCAAAAGTAG | TAGAAAGCAA | AAGGACAAGA | ACAATAACTT | CTCAAGATAA | ACCTAGTGGT | 840 |
| AATGATGTTG | AAATGGAAAC | TGAAGCTAAT | TTGGATACAA | GAAAAAGTGT | TAGTGACAAA | 900 |
| CAGTCTGCGG | TAACTGAATC | CTCAGAGGGT | ACAGTATCCT | TATTGAGGTC | TCACAAGAAT | 960 |
| CTTTTCTTAT | CTAAGTTGCA | ACATGGAACC | CAGCAACAAG | ACCTTAATAA | GAAAGAAAGA | 1020 |
| AGAGTAGGAA | CTCCTCAAAG | TACAAAAAAG | AAAAAAGAAA | GCAGAAGAGC | CACTGAAAGC | 1080 |
| AGAATACCTG | TTTCAAAGAG | TCAGCCGGTA | ACTCCTGAAA | AACATCGAGC | TTGGGGCAAA | 1140 |
| GAAGATGATT | CTAATTTGTT | AATTGGTATC | TATGAGTATG | CTATGGAAG | CTGGGAAATG | 1200 |
| ATTAAAATGG | ATCCAGACCT | CAGTTTAACA | CACAAGATTC | TTCCAGATGA | TCCTGATAAA | 1260 |
| AAACCACAAG | CAAAACAGTT | ACAGACCCGT | GCAGACTACC | TCATCAAACT | A | 1311 |

(2) INFORMATION FOR SEQ ID NO:4:

(i) SEQUENCE CHARACTERISTICS:
            (A) LENGTH: 975 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (xi) SEQUENCE DESCRIPTION: SEQ ID NO:4:

| | | | | | |
|---|---|---|---|---|---|
| ATGGCGGAGG | ATGTTTCCTC | AGCGGCCCCG | AGCCCGCGGC | GGTGTGCGGA | TGGTAGGGAT | 60 |
| GCCGACCCTA | CTGAGGAGCA | GATGGCAGAA | ACAGAGAGAA | ACGACGAGGA | GCAGTTCGAA | 120 |
| TGCCAGGAAC | TGCTCGAGTG | CCAGGTGCAG | GTGGGGGCCC | CCGAGGAGGA | GGAGGAGGAG | 180 |
| GAGGAGGACG | CGGGCCTGGT | GGCCGAGGCC | GAGGCCGTGT | GGCCGGGCTG | GATGCTCGAT | 240 |
| TTCCTCTGCC | TCTCTCTTTG | CCGAGCTTTC | CGCGACGGCC | GCTCCGAGGA | CTTCCGCAGG | 300 |
| ACCCGCAACA | GCGCAGAGGC | TATTATTCAT | GGACTATCCA | GTCTAACAGC | TTGCCAGTTG | 360 |

```
AGAACGATAT ACATATGTCA GTTTTTGACA AGAATTGCAG CAGGAAAAAC CCTTGATGCA      420

CAGTTTGAAA ATGATGAACG AATTACACCC TTGGAATCAG CCCTGATGAT TTGGGGTTCA      480

ATTGAAAAGG AACATGACAA ACTTCATGAA GAAATACAGA ATTTAATTAA AATTCAGGCT      540

ATAGCTGTTT GTATGGAAAA TGGCAACTTT AAAGAAGCAG AAGAAGTCTT TGAAAGAATA      600

TTTGGTGATC CAAATTCTCA TATGCCTTTC AAAAGCAAAT TGCTTATGAT AATCTCTCAG      660

AAAGATACAT TCATTCCTT TTTTCAACAC TTCAGCTACA ACCACATGAT GGAGAAAATT       720

AAGAGTTATG TGAATTATGT GCTAAGTGAA AAATCATCAA CCTTTCTAAT GAAGGCAGCG      780

GCAAAAGCTA GAAAAAGACA GGCATGGCTT TGGGAAGAAG ACAAGAATTT GAGATCTGGC     840

GTGAGGAAAT ATGGAGAGGG AAACTGGTCT AAAATACTGT TGCATTATAA ATTCAACAAC     900

CGGACAAGTG TCATGTTAAA AGACAGATGG AGGACCATGA AGAAACTAAA ACTGATTTCC    960

TCAGACAGCG AAGAC                                                     975
```

(2) INFORMATION FOR SEQ ID NO:5:

(i) SEQUENCE CHARACTERISTICS:
        (A) LENGTH: 439 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:5:

```
Met Ala Glu Asp Val Ser Ser Ala Ala Pro Ser Pro Arg Arg Cys Ala
 1               5                  10                  15

Asp Gly Arg Asp Ala Asp Pro Thr Glu Glu Gln Met Ala Glu Thr Glu
                20                  25                  30

Arg Asn Asp Glu Glu Gln Phe Glu Cys Gln Glu Leu Leu Glu Cys Gln
            35                  40                  45

Val Gln Val Gly Ala Pro Glu Glu Glu Glu Glu Glu Glu Glu Asp Ala
        50                  55                  60

Gly Leu Val Ala Glu Ala Glu Ala Val Trp Pro Gly Trp Met Leu Asp
65                  70                  75                  80

Phe Leu Cys Leu Ser Leu Cys Arg Ala Phe Arg Asp Gly Arg Ser Glu
                85                  90                  95

Asp Phe Arg Arg Thr Arg Asn Ser Ala Glu Ala Ile Ile His Gly Leu
                100                 105                 110

Ser Ser Leu Thr Ala Cys Gln Leu Arg Thr Ile Tyr Ile Cys Gln Phe
            115                 120                 125

Leu Thr Arg Ile Ala Ala Gly Lys Thr Leu Asp Ala Gln Phe Glu Asn
        130                 135                 140

Asp Glu Arg Ile Thr Pro Leu Glu Ser Ala Leu Met Ile Trp Gly Ser
145                 150                 155                 160

Ile Glu Lys Glu His Asp Lys Leu His Glu Glu Ile Gln Asn Leu Ile
                165                 170                 175

Lys Ile Gln Ala Ile Ala Val Cys Met Glu Asn Gly Asn Phe Lys Glu
            180                 185                 190

Ala Glu Glu Val Phe Glu Arg Ile Phe Gly Asp Pro Asn Ser His Met
        195                 200                 205

Pro Phe Lys Ser Lys Leu Leu Met Ile Ile Ser Gln Lys Asp Thr Phe
        210                 215                 220
```

```
His Ser Phe Phe Gln His Phe Ser Tyr Asn His Met Glu Lys Ile
225                 230                 235                 240

Lys Ser Tyr Val Asn Tyr Val Leu Ser Glu Lys Ser Ser Thr Phe Leu
                245                 250                 255

Met Lys Ala Ala Ala Lys Val Val Glu Ser Lys Arg Thr Arg Thr Ile
                260                 265                 270

Thr Ser Gln Asp Lys Pro Ser Gly Asn Asp Val Glu Met Glu Thr Glu
            275                 280                 285

Ala Asn Leu Asp Thr Arg Lys Ser Val Ser Asp Lys Gln Ser Ala Val
        290                 295                 300

Thr Glu Ser Ser Glu Gly Thr Val Ser Leu Leu Arg Ser His Lys Asn
305                 310                 315                 320

Leu Phe Leu Ser Lys Leu Gln His Gly Thr Gln Gln Gln Asp Leu Asn
                325                 330                 335

Lys Lys Glu Arg Arg Val Gly Thr Pro Gln Ser Thr Lys Lys Lys Lys
            340                 345                 350

Glu Ser Arg Arg Ala Thr Glu Ser Arg Ile Pro Val Ser Lys Ser Gln
        355                 360                 365

Pro Val Thr Pro Glu Lys His Arg Ala Arg Lys Arg Gln Ala Trp Leu
    370                 375                 380

Trp Glu Glu Asp Lys Asn Leu Arg Ser Gly Val Arg Lys Tyr Gly Glu
385                 390                 395                 400

Gly Asn Trp Ser Lys Ile Leu Leu His Tyr Lys Phe Asn Asn Arg Thr
                405                 410                 415

Ser Val Met Leu Lys Asp Arg Trp Arg Thr Met Lys Lys Leu Lys Leu
                420                 425                 430

Ile Ser Ser Asp Ser Glu Asp
            435

(2) INFORMATION FOR SEQ ID NO:6:

(i) SEQUENCE CHARACTERISTICS:
        (A) LENGTH: 320 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:6:

Leu Val Ala Glu Ala Glu Ala Val Trp Pro Gly Trp Met Leu Asp Phe
1               5                   10                  15

Leu Cys Leu Ser Leu Cys Arg Ala Phe Arg Asp Gly Arg Ser Glu Asp
                20                  25                  30

Phe Arg Arg Thr Arg Asn Ser Ala Glu Ala Ile Ile His Gly Leu Ser
            35                  40                  45

Ser Leu Thr Ala Cys Gln Leu Arg Thr Ile Tyr Ile Cys Gln Phe Leu
        50                  55                  60

Thr Arg Ile Ala Ala Gly Lys Thr Leu Asp Ala Gln Phe Glu Asn Asp
65                  70                  75                  80

Glu Arg Ile Thr Pro Leu Glu Ser Ala Leu Met Ile Trp Gly Ser Ile
                85                  90                  95

Glu Lys Glu His Asp Lys Leu His Glu Ile Gln Asn Leu Ile Lys
                100                 105                 110
```

-continued

```
Ile Gln Ala Ile Ala Val Cys Met Glu Asn Gly Asn Phe Lys Glu Ala
            115                 120                 125
Glu Glu Val Phe Glu Arg Ile Phe Gly Asp Pro Asn Ser His Met Pro
        130                 135                 140
Phe Lys Ser Lys Leu Leu Met Ile Ile Ser Gln Lys Asp Thr Phe His
145                 150                 155                 160
Ser Phe Phe Gln His Phe Ser Tyr Asn His Met Met Glu Lys Ile Lys
                165                 170                 175
Ser Tyr Val Asn Tyr Val Leu Ser Glu Lys Ser Ser Thr Phe Leu Met
            180                 185                 190
Lys Ala Ala Lys Val Val Glu Ser Lys Arg Thr Arg Thr Ile Thr
            195                 200                 205
Ser Gln Asp Lys Pro Ser Gly Asn Asp Val Glu Met Glu Thr Glu Ala
        210                 215                 220
Asn Leu Asp Thr Arg Lys Ser Val Ser Asp Lys Gln Ser Ala Val Thr
225                 230                 235                 240
Glu Ser Ser Glu Gly Thr Val Ser Leu Leu Arg Ser His Lys Asn Leu
                245                 250                 255
Phe Leu Ser Lys Leu Gln His Gly Thr Gln Gln Gln Asp Leu Asn Lys
            260                 265                 270
Lys Glu Arg Arg Val Gly Thr Pro Gln Ser Thr Lys Lys Lys Glu
            275                 280                 285
Ser Arg Arg Ala Thr Glu Ser Arg Ile Pro Val Ser Lys Ser Gln Pro
        290                 295                 300
Val Thr Pro Glu Lys His Arg Ala Arg Lys Arg Gln Ala Trp Leu Trp
305                 310                 315                 320
```

(2) INFORMATION FOR SEQ ID NO:7:

(i) SEQUENCE CHARACTERISTICS:
        (A) LENGTH: 437 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO:7:

```
Met Ala Glu Asp Val Ser Ser Ala Ala Pro Ser Pro Arg Arg Cys Ala
1               5                   10                  15
Asp Gly Arg Asp Ala Asp Pro Thr Glu Glu Gln Met Ala Glu Thr Glu
            20                  25                  30
Arg Asn Asp Glu Glu Gln Phe Glu Cys Gln Glu Leu Leu Glu Cys Gln
        35                  40                  45
Val Gln Val Gly Ala Pro Glu Glu Glu Glu Glu Glu Glu Glu Asp Ala
    50                  55                  60
Gly Leu Val Ala Glu Ala Glu Ala Val Trp Pro Gly Trp Met Leu Asp
65                  70                  75                  80
Phe Leu Cys Leu Ser Leu Cys Arg Ala Phe Arg Asp Gly Arg Ser Glu
                85                  90                  95
Asp Phe Arg Arg Thr Arg Asn Ser Ala Glu Ala Ile Ile His Gly Leu
            100                 105                 110
Ser Ser Leu Thr Ala Cys Gln Leu Arg Thr Ile Tyr Ile Cys Gln Phe
```

```
                115                 120                 125
Leu Thr Arg Ile Ala Ala Gly Lys Thr Leu Asp Ala Gln Phe Glu Asn
    130                 135                 140

Asp Glu Arg Ile Thr Pro Leu Glu Ser Ala Leu Met Ile Trp Gly Ser
145                 150                 155                 160

Ile Glu Lys Glu His Asp Lys Leu His Glu Glu Ile Gln Asn Leu Ile
                165                 170                 175

Lys Ile Gln Ala Ile Ala Val Cys Met Glu Asn Gly Asn Phe Lys Glu
            180                 185                 190

Ala Glu Glu Val Phe Glu Arg Ile Phe Gly Asp Pro Asn Ser His Met
        195                 200                 205

Pro Phe Lys Ser Lys Leu Leu Met Ile Ile Ser Gln Lys Asp Thr Phe
    210                 215                 220

His Ser Phe Phe Gln His Phe Ser Tyr Asn His Met Met Glu Lys Ile
225                 230                 235                 240

Lys Ser Tyr Val Asn Tyr Val Leu Ser Glu Lys Ser Ser Thr Phe Leu
                245                 250                 255

Met Lys Ala Ala Lys Val Val Glu Ser Lys Arg Thr Arg Thr Ile
            260                 265                 270

Thr Ser Gln Asp Lys Pro Ser Gly Asn Asp Val Glu Met Glu Thr Glu
        275                 280                 285

Ala Asn Leu Asp Thr Arg Lys Ser Val Ser Asp Lys Gln Ser Ala Val
    290                 295                 300

Thr Glu Ser Ser Glu Gly Thr Val Ser Leu Leu Arg Ser His Lys Asn
305                 310                 315                 320

Leu Phe Leu Ser Lys Leu Gln His Gly Thr Gln Gln Gln Asp Leu Asn
                325                 330                 335

Lys Lys Glu Arg Arg Val Gly Thr Pro Gln Ser Thr Lys Lys Lys
            340                 345                 350

Glu Ser Arg Arg Ala Thr Glu Ser Arg Ile Pro Val Ser Lys Ser Gln
        355                 360                 365

Pro Val Thr Pro Glu Lys His Arg Ala Trp Gly Lys Glu Asp Asp Ser
    370                 375                 380

Asn Leu Leu Ile Gly Ile Tyr Glu Tyr Gly Tyr Gly Ser Trp Glu Met
385                 390                 395                 400

Ile Lys Met Asp Pro Asp Leu Ser Leu Thr His Lys Ile Leu Pro Asp
                405                 410                 415

Asp Pro Asp Lys Lys Pro Gln Ala Lys Gln Leu Gln Thr Arg Ala Asp
            420                 425                 430

Tyr Leu Ile Lys Leu
        435

(2) INFORMATION FOR SEQ ID NO:8:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: N-terminal and C-terminal (xi) SEQUENCE DESCRIPTION: SEQ ID NO:8:
```

```
Met Ala Glu Asp Val Ser Ser Ala Ala Pro Ser Pro Arg Arg Cys Ala
  1               5                  10                  15

Asp Gly Arg Asp Ala Asp Pro Thr Glu Glu Gln Met Ala Glu Thr Glu
             20                  25                  30

Arg Asn Asp Glu Glu Gln Phe Glu Cys Gln Glu Leu Leu Glu Cys Gln
         35                  40                  45

Val Gln Val Gly Ala Pro Glu Glu Glu Glu Glu Glu Glu Glu Asp Ala
 50                  55                  60

Gly Leu Val Ala Glu Ala Glu Ala Val Trp Pro Gly Trp Met Leu Asp
 65                  70                  75                  80

Phe Leu Cys Leu Ser Leu Cys Arg Ala Phe Arg Asp Gly Arg Ser Glu
             85                  90                  95

Asp Phe Arg Arg Thr Arg Asn Ser Glu Ala Ile Ile His Gly Leu
            100                 105                 110

Ser Ser Leu Thr Ala Cys Gln Leu Arg Thr Ile Tyr Ile Cys Gln Phe
            115                 120                 125

Leu Thr Arg Ile Ala Ala Gly Lys Thr Leu Asp Ala Gln Phe Glu Asn
        130                 135                 140

Asp Glu Arg Ile Thr Pro Leu Glu Ser Ala Leu Met Ile Trp Gly Ser
145                 150                 155                 160

Ile Glu Lys Glu His Asp Lys Leu His Glu Ile Gln Asn Leu Ile
                165                 170                 175

Lys Ile Gln Ala Ile Ala Val Cys Met Glu Asn Gly Asn Phe Lys Glu
            180                 185                 190

Ala Glu Glu Val Phe Glu Arg Ile Phe Gly Asp Pro Asn Ser His Met
        195                 200                 205

Pro Phe Lys Ser Lys Leu Leu Met Ile Ile Ser Gln Lys Asp Thr Phe
        210                 215                 220

His Ser Phe Phe Gln His Phe Ser Tyr Asn His Met Met Glu Lys Ile
225                 230                 235                 240

Lys Ser Tyr Val Asn Tyr Val Leu Ser Glu Lys Ser Ser Thr Phe Leu
            245                 250                 255

Met Lys Ala Ala Ala Lys Ala Arg Lys Arg Gln Ala Trp Leu Trp Glu
        260                 265                 270

Glu Asp Lys Asn Leu Arg Ser Gly Val Arg Lys Tyr Gly Glu Gly Asn
        275                 280                 285

Trp Ser Lys Ile Leu Leu His Tyr Lys Phe Asn Asn Arg Thr Ser Val
290                 295                 300

Met Leu Lys Asp Arg Trp Arg Thr Met Lys Lys Leu Lys Leu Ile Ser
305                 310                 315                 320

Ser Asp Ser Glu Asp
            325

(2) INFORMATION FOR SEQ ID NO:9:

(i) SEQUENCE CHARACTERISTICS:
        (A) LENGTH: 597 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:9:

CTGGTGGCCG AGGCCGAGGC CGTGTGGCCG GGCTGGATGC TCGATTTCCT CTGCCTCTCT      60
```

```
CTTTGCCGAG CTTTCCGCGA CGGCCGCTCC GAGGACTTCC GCAGGACCCG CAACAGCGCA      120

GAGGCTATTA TTCATGGACT ATCCAGTCTA ACAGCTTGCC AGTTGAGAAC GATATACATA      180

TGTCAGTTTT TGACAAGAAT TGCAGCAGGA AAAACCCTTG ATGCACAGTT TGAAAATGAT      240

GAACGAATTA CACCCTTGGA ATCAGCCCTG ATGATTTGGG GTTCAATTGA AAAGGAACAT      300

GACAAACTTC ATGAAGAAAT ACAGAATTTA ATTAAAATTC AGGCTATAGC TGTTTGTATG      360

GAAAATGGCA ACTTTAAAGA AGCAGAAGAA GTCTTTGAAA GAATATTTGG TGATCCAAAT      420

TCTCATATGC CTTTCAAAAG CAAATTGCTT ATGATAATCT CTCAGAAAGA TACATTTCAT      480

TCCTTTTTTC AACACTTCAG CTACAACCAC ATGATGGAGA AAATTAAGAG TTATGTGAAT      540

TATGTGCTAA GTGAAAAATC ATCAACCTTT CTAATGAAGG CAGCGGCAAA AGTAGTA        597

(2) INFORMATION FOR SEQ ID NO:10:

(i) SEQUENCE CHARACTERISTICS:
        (A) LENGTH: 186 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:10:

AGAAAAAGAC AGGCATGGCT TTGGGAAGAA GACAAGAATT TGAGATCTGG CGTGAGGAAA       60

TATGGAGAGG GAAACTGGTC TAAAATACTG TTGCATTATA AATTCAACAA CCGGACAAGT      120

GTCATGTTAA AAGACAGATG GAGGACCATG AAGAAACTAA AACTGATTTC CTCAGACAGC      180

GAAGAC                                                                  186

(2) INFORMATION FOR SEQ ID NO:11:

(i) SEQUENCE CHARACTERISTICS:
        (A) LENGTH: 199 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:11:

Leu Val Ala Glu Ala Glu Ala Val Trp Pro Gly Trp Met Leu Asp Phe
 1               5                  10                  15

Leu Cys Leu Ser Leu Cys Arg Ala Phe Arg Asp Gly Arg Ser Glu Asp
                20                  25                  30

Phe Arg Arg Thr Arg Asn Ser Ala Glu Ala Ile Ile His Gly Leu Ser
            35                  40                  45

Ser Leu Thr Ala Cys Gln Leu Arg Thr Ile Tyr Ile Cys Gln Phe Leu
        50                  55                  60

Thr Arg Ile Ala Ala Gly Lys Thr Leu Asp Ala Gln Phe Glu Asn Asp
65                  70                  75                  80

Glu Arg Ile Thr Pro Leu Glu Ser Ala Leu Met Ile Trp Gly Ser Ile
                85                  90                  95

Glu Lys Glu His Asp Lys Leu His Glu Glu Ile Gln Asn Leu Ile Lys
            100                 105                 110
```

```
Ile Gln Ala Ile Ala Val Cys Met Glu Asn Gly Asn Phe Lys Glu Ala
        115                 120                 125

Glu Glu Val Phe Glu Arg Ile Phe Gly Asp Pro Asn Ser His Met Pro
        130                 135                 140

Phe Lys Ser Lys Leu Leu Met Ile Ile Ser Gln Lys Asp Thr Phe His
145                 150                 155                 160

Ser Phe Phe Gln His Phe Ser Tyr Asn His Met Met Glu Lys Ile Lys
                165                 170                 175

Ser Tyr Val Asn Tyr Val Leu Ser Glu Lys Ser Ser Thr Phe Leu Met
            180                 185                 190

Lys Ala Ala Ala Lys Val Val
        195
```

(2) INFORMATION FOR SEQ ID NO:12:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: C-terminal (xi) SEQUENCE DESCRIPTION: SEQ ID NO:12:

```
Arg Lys Arg Gln Ala Trp Leu Trp Glu Glu Asp Lys Asn Leu Arg Ser
1               5                   10                  15

Gly Val Arg Lys Tyr Gly Glu Gly Asn Trp Ser Lys Ile Leu Leu His
            20                  25                  30

Tyr Lys Phe Asn Asn Arg Thr Ser Val Met Leu Lys Asp Arg Trp Arg
        35                  40                  45

Thr Met Lys Lys Leu Lys Leu Ile Ser Ser Asp Ser Glu Asp
    50                  55                  60
```

(2) INFORMATION FOR SEQ ID NO:13:

(i) SEQUENCE CHARACTERISTICS:
        (A) LENGTH: 1125 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:13:

```
GAGGCACGGC TGGAAGAGGC AGTCAATCGC TGGGTGCTCA AGTTCTACTT CCACGAGGCG      60

CTGCGGGCCT TTCGGGGTAG CCGGTACGGG GACTTCAGAC AGATCCGGGA CATCATGCAG     120

GCTTTGCTTG TCAGGCCCTT GGGGAAGGAG CACACCGTGT CCCGATTGCT GCGGGTTATG     180

CAGTGTCTGT CGCGGATTGA AGAAGGGGAA AATTTAGACT GTTCCTTTGA TATGGAGGCT     240

GAGCTCACAC CACTGGAATC AGCTATCAAT GTGCTGGAGA TGATTAAAAC GGAATTTACA     300

CTGACAGAAG CAGTGGTCGA ATCCAGTAGA AAACTGGTCA AGGAAGCTGC TGTCATTATT     360

TGTATCAAAA ACAAAGAATT TGAAAAGGCT TCAAAAATTT TGAAAAACA TATGTCCAAG      420

GACCCCACAA CTCAGAAGCT GAGAAATGAT CTCCTGAATA TTATTCGAGA AAAGAACTTG     480
```

```
GCCCATCCTG TTATCCAGAA CTTTTCATAT GAGACCTTCC AGCAGAAGAT GCTGCGCTTC      540

CTGGAGAGCC ACCTGGATGA CGCCGAGCCC TACCTCCTCA CGATGGCCAA AAAGGCTTTG      600

AAATCTGAGT CCGCTGCCTC AAGTACAGGG AAGGAAGATA AACAGCCAGC ACCAGGGCCT      660

GTGGAAAAGC CACCCAGAGA ACCCGCAAGG CAGCTACGGA ATCCTCCAAC CACCATTGGA      720

ATGATGACTC TGAAAGCAGC TTTCAAGACT CTGTCTGGTG CACAGGATTC TGAGGCAGCC      780

TTTGCAAAAC TGGACCAGAA GGATCTGGTT CTTCCTACTC AAGCTCTCCC AGCATCACCA      840

GCCCTCAAAA ACAAGAGACC CAGAAAAGAT GAAAACGAAA GTTCAGCCCC GGCTGACGGT      900

GAGGGTGGCT CGGAACTGCA GCCCAAGAAC AAGCGCATGA CAATAAGCAG ATTGGTCTTG      960

GAGGAGGACA GCCAGAGTAC TGAGCCCAGC GCAGGCCTCA ACTCCTCCCA GGAGGCCGCT     1020

TCAGCGCCAC CATCCAAGCC CACCGTTCTC AACCAACCCC TCCCTGGAGA GAAGAATCCC     1080

AAAGTACCCA AAGGCAAGTG GAACAGCTCT AATGGGGTTG AAGAA                     1125
```

(2) INFORMATION FOR SEQ ID NO:14:

(i) SEQUENCE CHARACTERISTICS:
        (A) LENGTH: 410 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:14:

```
Glu Ala Arg Leu Glu Glu Ala Val Asn Arg Trp Val Leu Lys Phe Tyr
1               5                   10                  15

Phe His Glu Ala Leu Arg Ala Phe Arg Gly Ser Arg Tyr Gly Asp Phe
            20                  25                  30

Arg Gln Ile Arg Asp Ile Met Gln Ala Leu Leu Val Arg Pro Leu Gly
        35                  40                  45

Lys Glu His Thr Val Ser Arg Leu Leu Arg Val Met Gln Cys Leu Ser
    50                  55                  60

Arg Ile Glu Glu Gly Glu Asn Leu Asp Cys Ser Phe Asp Met Glu Ala
65                  70                  75                  80

Glu Leu Thr Pro Leu Glu Ser Ala Ile Asn Val Leu Glu Met Ile Lys
                85                  90                  95

Thr Glu Phe Thr Leu Thr Glu Ala Val Val Glu Ser Ser Arg Lys Leu
            100                 105                 110

Val Lys Glu Ala Ala Val Ile Ile Cys Ile Lys Asn Lys Glu Phe Glu
        115                 120                 125

Lys Ala Ser Lys Ile Leu Lys Lys His Met Ser Lys Asp Pro Thr Thr
    130                 135                 140

Gln Lys Leu Arg Asn Asp Leu Leu Asn Ile Ile Arg Glu Lys Asn Leu
145                 150                 155                 160

Ala His Pro Val Ile Gln Asn Phe Ser Tyr Glu Thr Phe Gln Gln Lys
                165                 170                 175

Met Leu Arg Phe Leu Glu Ser His Leu Asp Asp Ala Glu Pro Tyr Leu
            180                 185                 190

Leu Thr Met Ala Lys Lys Ala Leu Lys Ser Glu Ser Ala Ala Ser Ser
        195                 200                 205

Thr Gly Lys Glu Asp Lys Gln Pro Ala Pro Gly Pro Val Glu Lys Pro
    210                 215                 220
```

```
Pro Arg Glu Pro Ala Arg Gln Leu Arg Asn Pro Pro Thr Thr Ile Gly
225                 230                 235                 240

Met Met Thr Leu Lys Ala Ala Phe Lys Thr Leu Ser Gly Ala Gln Asp
            245                 250                 255

Ser Glu Ala Ala Phe Ala Lys Leu Asp Gln Lys Asp Leu Val Leu Pro
            260                 265                 270

Thr Gln Ala Leu Pro Ala Ser Pro Ala Leu Lys Asn Lys Arg Pro Arg
            275                 280                 285

Lys Asp Glu Asn Glu Ser Ser Ala Pro Ala Asp Gly Glu Gly Gly Ser
290                 295                 300

Glu Leu Gln Pro Lys Asn Lys Arg Met Thr Ile Ser Arg Leu Val Leu
305                 310                 315                 320

Glu Glu Asp Ser Gln Ser Thr Glu Pro Ser Ala Gly Leu Asn Ser Ser
            325                 330                 335

Gln Glu Ala Ala Ser Ala Pro Pro Ser Lys Pro Thr Val Leu Asn Gln
            340                 345                 350

Pro Leu Pro Gly Glu Lys Asn Pro Lys Val Pro Lys Gly Lys Trp Asn
            355                 360                 365

Ser Ser Asn Gly Val Glu Glu Lys Glu Thr Trp Val Glu Glu Asp Glu
370                 375                 380

Leu Phe Gln Val Gln Ala Ala Pro Asp Glu Asp Ser Thr Thr Asn Ile
385                 390                 395                 400

Thr Lys Lys Gln Lys Trp Thr Val Glu Glu
                405                 410

(2) INFORMATION FOR SEQ ID NO:15:

(i) SEQUENCE CHARACTERISTICS:
        (A) LENGTH: 1368 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:15:

GAGGCACGGC TGGAAGAGGC AGTCAATCGC TGGGTGCTCA AGTTCTACTT CCACGAGGCG      60

CTGCGGGCCT TTCGGGGTAG CCGGTACGGG GACTTCAGAC AGATCCGGGA CATCATGCAG     120

GCTTTGCTTG TCAGGCCCTT GGGGAAGGAG CACACCGTGT CCCGATTGCT GCGGGTTATG     180

CAGTGTCTGT CGCGGATTGA AGAAGGGGAA AATTTAGACT GTTCCTTTGA TATGGAGGCT     240

GAGCTCACAC CACTGGAATC AGCTATCAAT GTGCTGGAGA TGATTAAAAC GGAATTTACA     300

CTGACAGAAG CAGTGGTCGA ATCCAGTAGA AAACTGGTCA AGGAAGCTGC TGTCATTATT     360

TGTATCAAAA ACAAAGAATT TGAAAAGGCT TCAAAAATTT TGAAAAAACA TATGTCCAAG     420

GACCCCACAA CTCAGAAGCT GAGAAATGAT CTCCTGAATA TTATTCGAGA AAAGAACTTG     480

GCCCATCCTG TTATCCAGAA CTTTTCATAT GAGACCTTCC AGCAGAAGAT GCTGCGCTTC     540

CTGGAGAGCC ACCTGGATGA CGCCGAGCCC TACCTCCTCA CGATGGCCAA AAAGGCTTTG     600

AAATCTGAGT CCGCTGCCTC AAGTACAGGG AAGGAAGATA ACAGCCAGCC ACCAGGGCCT     660

GTGGAAAAGC CACCCAGAGA ACCCGCAAGG CAGCTACGGA ATCCTCCAAC CACCATTGGA     720

ATGATGACTC TGAAAGCAGC TTTCAAGACT CTGTCTGGTG CACAGGATTC TGAGGCAGCC     780

TTTGCAAAAC TGGACCAGAA GGATCTGGTT CTTCCTACTC AAGCTCTCCC AGCATCACCA     840
```

-continued

```
GCCCTCAAAA ACAAGAGACC CAGAAAAGAT GAAAACGAAA GTTCAGCCCC GGCTGACGGT      900

GAGGGTGGCT CGGAACTGCA GCCCAAGAAC AAGCGCATGA CAATAAGCAG ATTGGTCTTG      960

GAGGAGGACA GCCAGAGTAC TGAGCCCAGC GCAGGCCTCA ACTCCTCCCA GGAGGCCGCT     1020

TCAGCGCCAC CATCCAAGCC CACCGTTCTC AACCAACCCC TCCCTGGAGA GAAGAATCCC     1080

AAAGTACCCA AAGGCAAGTG GAACAGCTCT AATGGGGTTG AAGAAAAGGA GACTTGGGTG     1140

GAAGAGGATG AACTGTTTCA AGTTCAGGCA GCACCAGATG AAGACAGTAC AACCAATATA     1200

ACAAAAAAGC AGAAGTGGAC TGTAGAAGAA AGCGAGTGGG TCAAGGCTGG AGTGCAGAAA     1260

TATGGGGAAG GAAACTGGGC TGCCATTTCT AAAAATTACC CATTTGTTAA CCGAACAGCT     1320

GTGATGATTA AGGATCGCTG GCGGACCATG AAAAGACTTG GCATGAAC                  1368
```

(2) INFORMATION FOR SEQ ID NO:16:

(i) SEQUENCE CHARACTERISTICS:
        (A) LENGTH: 456 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:16:

```
Glu Ala Arg Leu Glu Glu Ala Val Asn Arg Trp Val Leu Lys Phe Tyr
1               5                  10                  15

Phe His Glu Ala Leu Arg Ala Phe Arg Gly Ser Arg Tyr Gly Asp Phe
            20                  25                  30

Arg Gln Ile Arg Asp Ile Met Gln Ala Leu Leu Val Arg Pro Leu Gly
        35                  40                  45

Lys Glu His Thr Val Ser Arg Leu Leu Arg Val Met Gln Cys Leu Ser
    50                  55                  60

Arg Ile Glu Glu Gly Glu Asn Leu Asp Cys Ser Phe Asp Met Glu Ala
65                  70                  75                  80

Glu Leu Thr Pro Leu Glu Ser Ala Ile Asn Val Leu Glu Met Ile Lys
                85                  90                  95

Thr Glu Phe Thr Leu Thr Glu Ala Val Val Glu Ser Ser Arg Lys Leu
            100                 105                 110

Val Lys Glu Ala Ala Val Ile Ile Cys Ile Lys Asn Lys Glu Phe Glu
        115                 120                 125

Lys Ala Ser Lys Ile Leu Lys Lys His Met Ser Lys Asp Pro Thr Thr
    130                 135                 140

Gln Lys Leu Arg Asn Asp Leu Leu Asn Ile Ile Arg Glu Lys Asn Leu
145                 150                 155                 160

Ala His Pro Val Ile Gln Asn Phe Ser Tyr Glu Thr Phe Gln Gln Lys
                165                 170                 175

Met Leu Arg Phe Leu Glu Ser His Leu Asp Asp Ala Glu Pro Tyr Leu
            180                 185                 190

Leu Thr Met Ala Lys Lys Ala Leu Lys Ser Glu Ser Ala Ala Ser Ser
        195                 200                 205

Thr Gly Lys Glu Asp Lys Gln Pro Ala Pro Gly Pro Val Glu Lys Pro
    210                 215                 220

Pro Arg Glu Pro Ala Arg Gln Leu Arg Asn Pro Pro Thr Thr Ile Gly
225                 230                 235                 240

Met Met Thr Leu Lys Ala Ala Phe Lys Thr Leu Ser Gly Ala Gln Asp
```

-continued

```
            245                 250                 255
Ser Glu Ala Ala Phe Ala Lys Leu Asp Gln Lys Asp Leu Val Leu Pro
                260                 265                 270
Thr Gln Ala Leu Pro Ala Ser Pro Ala Leu Lys Asn Lys Arg Pro Arg
            275                 280                 285
Lys Asp Glu Asn Glu Ser Ser Ala Pro Ala Asp Gly Glu Gly Gly Ser
        290                 295                 300
Glu Leu Gln Pro Lys Asn Lys Arg Met Thr Ile Ser Arg Leu Val Leu
305                 310                 315                 320
Glu Glu Asp Ser Gln Ser Thr Glu Pro Ser Ala Gly Leu Asn Ser Ser
                325                 330                 335
Gln Glu Ala Ala Ser Ala Pro Pro Ser Lys Pro Thr Val Leu Asn Gln
            340                 345                 350
Pro Leu Pro Gly Glu Lys Asn Pro Lys Val Pro Lys Gly Lys Trp Asn
        355                 360                 365
Ser Ser Asn Gly Val Glu Glu Lys Glu Thr Trp Val Glu Glu Asp Glu
    370                 375                 380
Leu Phe Gln Val Gln Ala Ala Pro Asp Glu Asp Ser Thr Thr Asn Ile
385                 390                 395                 400
Thr Lys Lys Gln Lys Trp Thr Val Glu Glu Ser Glu Trp Val Lys Ala
                405                 410                 415
Gly Val Gln Lys Tyr Gly Glu Gly Asn Trp Ala Ala Ile Ser Lys Asn
            420                 425                 430
Tyr Pro Phe Val Asn Arg Thr Ala Val Met Ile Lys Asp Arg Trp Arg
        435                 440                 445
Thr Met Lys Arg Leu Gly Met Asn
    450                 455
```

(2) INFORMATION FOR SEQ ID NO:17:

(i) SEQUENCE CHARACTERISTICS:
        (A) LENGTH: 2907 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:17:

```
GGAATTCGGC ACGAGGGACG GCGGGCCCCG CTTCCGGCCC GGGCGTCGTG CGTGACCCAG      60

CGGCGTCACA GCCGAGGAAG CGGCCCGGCC GGGAGGGCGG GGAGGCGCGC GGCGATCGGA     120

CACGATGGCG GGAGGAGGCG GGAGTAGCGA CGGCAGCGGG CGGGCAGCTG GCAGGCGGGC     180

GTCCCGCAGT AGCGGGCGGG CCCGGCGGGG GCGCCACGAG CCGGGGCTGG GGGGCCCGGC     240

GGAGCGCGGC GCGGGGAGG CACGGCTGGA AGAGGCAGTC AATCGCTGGG TGCTCAAGTT     300

CTACTTCCAC GAGGCGCTGC GGGCCTTTCG GGGTAGCCGG TACGGGGACT TCAGACAGAT     360

CCGGGACATC ATGCAGGCTT TGCTTGTCAG GCCCTTGGGG AAGGAGCACA CCGTGTCCCG     420

ATTGCTGCGG GTTATGCAGT GTCTGTCGCG GATTGAAGAA GGGGAAAATT TAGACTGTTC     480

CTTTGATATG GAGGCTGAGC TCACACCACT GGAATCAGCT ATCAATGTGC TGGAGATGAT     540

TAAAACGGAA TTTACACTGA CAGAAGCAGT GGTCGAATCC AGTAGAAAAC TGGTCAAGGA     600

AGCTGCTGTC ATTATTTGTA TCAAAAACAA AGAATTTGAA AAGGCTTCAA AAATTTTGAA     660

AAAACATATG TCCAAGGACC CCACAACTCA GAAGCTGAGA AATGATCTCC TGAATATTAT     720
```

-continued

```
TCGAGAAAAG AACTTGGCCC ATCCTGTTAT CCAGAACTTT TCATATGAGA CCTTCCAGCA    780
GAAGATGCTG CGCTTCCTGG AGAGCCACCT GGATGACGCC GAGCCCTACC TCCTCACGAT    840
GGCCAAAAAG GCTTTGAAAT CTGAGTCCGC TGCCTCAAGT ACAGGGAAGG AAGATAAACA    900
GCCAGCACCA GGGCCTGTGG AAAAGCCACC CAGAGAACCC GCAAGGCAGC TACGGAATCC    960
TCCAACCACC ATTGGAATGA TGACTCTGAA AGCAGCTTTC AAGACTCTGT CTGGTGCACA   1020
GGATTCTGAG GCAGCCTTTG CAAAACTGGA CCAGAAGGAT CTGGTTCTTC CTACTCAAGC   1080
TCTCCCAGCA TCACCAGCCC TCAAAAACAA GAGACCCAGA AAAGATGAAA ACGAAAGTTC   1140
AGCCCCGGCT GACGGTGAGG GTGGCTCGGA ACTGCAGCCC AAGAACAAGC GCATGACAAT   1200
AAGCAGATTG GTCTTGGAGG AGGACAGCCA GAGTACTGAG CCCAGCGCAG GCCTCAACTC   1260
CTCCCAGGAG GCCGCTTCAG CGCCACCATC CAAGCCCACC GTTCTCAACC AACCCCTCCC   1320
TGGAGAGAAG AATCCCAAAG TACCCAAAGG CAAGTGGAAC AGCTCTAATG GGGTTGAAGA   1380
AAAGGAGACT TGGGTGGAAG AGGATGAACT GTTTCAAGTT CAGGCAGCAC CAGATGAAGA   1440
CAGTACAACC AATATAACAA AAAAGCAGAA GTGGACTGTA GAAGAAAGCG AGTGGGTCAA   1500
GGCTGGAGTG CAGAAATATG GGAAGGAAA CTGGGCTGCC ATTTCTAAAA ATTACCCATT   1560
TGTTAACCGA ACAGCTGTGA TGATTAAGGA TCGCTGGCGG ACCATGAAAA GACTTGGCAT   1620
GAACTGAAAC AGGCTTTCAT TTCCACAGAA TTCACAGGAG CATGGTTCCT AATAATAGCC   1680
CCTGATAGTC TGCTCTTTCT TTCTTTTTCT TTTTTTTTTT TTTTGAGAC AGAGTCTCGC   1740
TCTGTCACCC AGGCTGGAGT GCAGTGGCGT GATCTCGGCT CACTGCGACC TCCGTCTCCC   1800
GGGCTCACGC CATTCTCCTG CCTCAGCCTC CGAGTAGCTG GGACTACAGG CGCCCGCCAT   1860
CACGCCCGGC TAATGTTTTG TATTTTTAGT AAANACGGGG TTTCACCGTG TTGGCCAGGA   1920
TGGTCTCGAT CTCCTGACCT CGTGATCCAC CCAACTCGGC CTCCCAAAGT GCTGGGATTA   1980
CAGGCATGAN CCACCGCGCC TGGCATCTGC TGTTTCTTTC AGAAGCTGGG CTGGGATGAG   2040
AATTTTGGGC AACCTCCTTC GACGTGGGGG AGGTCCCATT TCCACTTCAT CACTGTTGGA   2100
GATCATGGAG CTAAGAAGCA GAGCCAAGTC CACCCATGTC CTTGGCAGAG ATGACGGCAC   2160
ACAGCTTGTG CAGTGCCAGA ATATCATTAG CGTTTCCCTT CTTTAGTGGT TTGCTTAAAT   2220
TTAAATCCCT GGTAATCTGT AGAACCTTCT CCTAGGAAAT GGTGAAGTCT ATTAGGAGCC   2280
ACTTGTGACT CCATGACCTG TTAAAACCAG CAATGTGAGT ATTATTTGGA GTAAATTTGT   2340
TCCACGTCAA GTTCTGGCCT TCTGATGCAA ATGCAAAGGA ACTTAGTNTG TTATGAACCC   2400
AGGTTGATGA CAGACCAGTC CTTGTGGAAT AAGATTCCCT TTAAAAACTC TTTAGCCAGT   2460
CGTGACATCA ACCCTAGACC TGTCTGCCTT GGCATTTGCT GTCAANATNT GCTGGGCTAT   2520
GTAGGCAGGT TAATCCTCCA CTTCTCATGT GGTTGAACCA GTGTGTTTTT TGGTAAAATG   2580
GTGATTGTAG ATAAGATTAG TTCCCTGATC CCCTGCCCCC TGTCCCCTGC CTCTTTTCCC   2640
AATTCCCTTC CTTATGCTGG ACTTTTAAAG CTTAAAAAAA ATCCGATTGA ATATAAATGC   2700
CTAATTTCAT TCTTTTGTGA AATGGTTGCT TCCTCCTGAT TCCCTAATTG TGCTGTGTTC   2760
GTGTCTTGCA CTGGAATTCA ACATTCCCTT CTCCTTTTGT ACTGTGTTGT GCTTGCTGTC   2820
TCTCCCGGAC ACCCTTAAAG ACTGTCTTTT TAGCAAAAAA TTTCAGTAAA GTGTTTTCTG   2880
TAATCTTTTT TTAAAAAAAA AAAAAAA                                       2907
```

(2) INFORMATION FOR SEQ ID NO:18:

(i) SEQUENCE CHARACTERISTICS:

(A) LENGTH: 500 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:18:

Met Ala Gly Gly Gly Ser Ser Asp Gly Ser Gly Arg Ala Ala Gly
1               5                   10                  15

Arg Arg Ala Ser Arg Ser Ser Gly Arg Ala Arg Arg Gly Arg His Glu
            20                  25                  30

Pro Gly Leu Gly Gly Pro Ala Glu Arg Gly Ala Gly Glu Ala Arg Leu
            35                  40                  45

Glu Glu Ala Val Asn Arg Trp Val Leu Lys Phe Tyr Phe His Glu Ala
        50                  55                  60

Leu Arg Ala Phe Arg Gly Ser Arg Tyr Gly Asp Phe Arg Gln Ile Arg
65                  70                  75                  80

Asp Ile Met Gln Ala Leu Leu Val Arg Pro Leu Gly Lys Glu His Thr
                85                  90                  95

Val Ser Arg Leu Leu Arg Val Met Gln Cys Leu Ser Arg Ile Glu Glu
            100                 105                 110

Gly Glu Asn Leu Asp Cys Ser Phe Asp Met Glu Ala Glu Leu Thr Pro
            115                 120                 125

Leu Glu Ser Ala Ile Asn Val Leu Glu Met Ile Lys Thr Glu Phe Thr
    130                 135                 140

Leu Thr Glu Ala Val Val Glu Ser Ser Arg Lys Leu Val Lys Glu Ala
145                 150                 155                 160

Ala Val Ile Ile Cys Ile Lys Asn Lys Glu Phe Glu Lys Ala Ser Lys
                165                 170                 175

Ile Leu Lys Lys His Met Ser Lys Asp Pro Thr Thr Gln Lys Leu Arg
            180                 185                 190

Asn Asp Leu Leu Asn Ile Ile Arg Glu Lys Asn Leu Ala His Pro Val
            195                 200                 205

Ile Gln Asn Phe Ser Tyr Glu Thr Phe Gln Gln Lys Met Leu Arg Phe
    210                 215                 220

Leu Glu Ser His Leu Asp Asp Ala Glu Pro Tyr Leu Leu Thr Met Ala
225                 230                 235                 240

Lys Lys Ala Leu Lys Ser Glu Ser Ala Ala Ser Ser Thr Gly Lys Glu
                245                 250                 255

Asp Lys Gln Pro Ala Pro Gly Pro Val Glu Lys Pro Pro Arg Glu Pro
            260                 265                 270

Ala Arg Gln Leu Arg Asn Pro Pro Thr Thr Ile Gly Met Met Thr Leu
            275                 280                 285

Lys Ala Ala Phe Lys Thr Leu Ser Gly Ala Gln Asp Ser Glu Ala Ala
    290                 295                 300

Phe Ala Lys Leu Asp Gln Lys Asp Leu Val Leu Pro Thr Gln Ala Leu
305                 310                 315                 320

Pro Ala Ser Pro Ala Leu Lys Asn Lys Arg Pro Arg Lys Asp Glu Asn
                325                 330                 335

Glu Ser Ser Ala Pro Ala Asp Gly Glu Gly Gly Ser Glu Leu Gln Pro
            340                 345                 350

Lys Asn Lys Arg Met Thr Ile Ser Arg Leu Val Leu Glu Glu Asp Ser
            355                 360                 365

```
Gln Ser Thr Glu Pro Ser Ala Gly Leu Asn Ser Gln Glu Ala Ala
    370                 375                 380

Ser Ala Pro Pro Ser Lys Pro Thr Val Leu Asn Gln Pro Leu Pro Gly
385                 390                 395                 400

Glu Lys Asn Pro Lys Val Pro Lys Gly Lys Trp Asn Ser Ser Asn Gly
                405                 410                 415

Val Glu Glu Lys Glu Thr Trp Val Glu Glu Asp Glu Leu Phe Gln Val
            420                 425                 430

Gln Ala Ala Pro Asp Glu Asp Ser Thr Thr Asn Ile Thr Lys Lys Gln
            435                 440                 445

Lys Trp Thr Val Glu Glu Ser Glu Trp Val Lys Ala Gly Val Gln Lys
    450                 455                 460

Tyr Gly Glu Gly Asn Trp Ala Ala Ile Ser Lys Asn Tyr Pro Phe Val
465                 470                 475                 480

Asn Arg Thr Ala Val Met Ile Lys Asp Arg Trp Arg Thr Met Lys Arg
                485                 490                 495

Leu Gly Met Asn
            500

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:19:

TTGAATTCGA GGCACGGCTG GAAGAG                                      26

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:20:

CGGGATCCTG TTTCAGTTCA TGCCAA                                      26

(2) INFORMATION FOR SEQ ID NO:21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:21:

CGGGATCCTC ATTCTACAGT CCACTTCTGC T                                31
```

(2) INFORMATION FOR SEQ ID NO:22:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (ii) MOLECULE TYPE: cDNA
        (A) DESCRIPTION: TRF2

(iii) HYPOTHETICAL: NO (vi) ORIGINAL SOURCE:
        (A) ORGANISM: Homo sapiens (xi) SEQUENCE DESCRIPTION: SEQ ID NO:22:

```
GCACGGCTGG AAGAGGCAGT CAATCGCTGG GTGCTCAAGT TCTACTTCCA CGAGGCGCTG      60

CGGGCCTTTC GGGGTAGCCG GTACGGGGAC TTCAGACAGA TCCGGGACAT CATGCAGGCT     120

TTGCTTGTCA GGCCCTTGGG GAAGGAGCAC ACCGTGTCCC GATTGCTGCG GGTTATGCAG     180

TGTCTGTCGC GGATTGAAGA AGGGGAAAAT TTAGACTGTT CCTTTGATAT GGAGGCTGAG     240

CTCACACCAC TGGAATCAGC TATCAATGTG CTGGAGATGA TTAAAACGGA ATTTACACTG     300

ACAGAAGCAG TGGTCGAATC CAGTAGAAAA CTGGTCAAGG AAGCTGCTGT CATTATTTGT     360

ATCAAAAACA AAGAATTTGA AAAGGCTTCA AAAATTTTGA AAAAACATAT GTCCAAGGAC     420

CCCACAACTC AGAAGCTGAG AAATGATCTC CTGAATATTA TTCGAGAAAA GAACTTGGCC     480

CATCCTGTTA TCCAGAACTT TTCATATGAG ACCTTCCAGC AGAAGATGCT GCGCTTCCTG     540

GAGAGCCACC TGGATGACGC CGAGCCCTAC CTCCTCACGA TGGCCAAAAA GGCTTTGAAA     600
```

(2) INFORMATION FOR SEQ ID NO:23:

(i) SEQUENCE CHARACTERISTICS:
        (A) LENGTH: 200 amino acids
        (B) TYPE: amino acid
        (C) STRANDEDNESS: single
        (D) TOPOLOGY: linear (ii) MOLECULE TYPE: protein
        (A) DESCRIPTION: TRF2

(iii) HYPOTHETICAL: NO (vi) ORIGINAL SOURCE:
        (A) ORGANISM: Homo sapiens (xi) SEQUENCE DESCRIPTION: SEQ ID NO:23:

```
Ala Arg Leu Glu Glu Ala Val Asn Arg Trp Val Leu Lys Phe Tyr Phe
1               5                   10                  15

His Glu Ala Leu Arg Ala Phe Arg Gly Ser Arg Tyr Gly Asp Phe Arg
            20                  25                  30

Gln Ile Arg Asp Ile Met Gln Ala Leu Leu Val Arg Pro Leu Gly Lys
        35                  40                  45

Glu His Thr Val Ser Arg Leu Leu Arg Val Met Gln Cys Leu Ser Arg
    50                  55                  60

Ile Glu Glu Gly Glu Asn Leu Asp Cys Ser Phe Asp Met Glu Ala Glu
65                  70                  75                  80

Leu Thr Pro Leu Glu Ser Ala Ile Asn Val Leu Glu Met Ile Lys Thr
                85                  90                  95

Glu Phe Thr Leu Thr Glu Ala Val Val Glu Ser Ser Arg Lys Leu Val
            100                 105                 110
```

-continued

```
Lys Glu Ala Ala Val Ile Ile Cys Ile Lys Asn Lys Glu Phe Glu Lys
            115                 120                 125

Ala Ser Lys Ile Leu Lys Lys His Met Ser Lys Asp Pro Thr Thr Gln
    130                 135                 140

Lys Leu Arg Asn Asp Leu Leu Asn Ile Ile Arg Glu Lys Asn Leu Ala
145                 150                 155                 160

His Pro Val Ile Gln Asn Phe Ser Tyr Glu Thr Phe Gln Gln Lys Met
                165                 170                 175

Leu Arg Phe Leu Glu Ser His Leu Asp Asp Ala Glu Pro Tyr Leu Leu
            180                 185                 190

Thr Met Ala Lys Lys Ala Leu Lys
    195                 200
```

NUCLEIC ACID ENCODING AN ALTERED TELOMERE REPEAT BINDING FACTOR 2

CROSS-REFERENCE TO RELATED APPLICATIONS

The present Application is a Division of application U.S. Ser. No. 09/018,628 filed on Feb. 4, 1998, U.S. Pat. No. 5,917,019, which is a Continuation-in-Part of U.S. Ser. No. 08/800,264 filed on Feb. 13, 1997, now issued as U.S. Pat. No: 5,859,183 on Jan. 12, 1999, the disclosures of which are hereby incorporated by reference in their entireties. Applicants claim the benefit of this Applications under 35 U.S.C. §120.

GOVERNMENTAL SUPPORT

The research leading to the present invention was supported, at least in part, by a grant from U.S. Government Granting Agency, Grant No. GM 49046. Accordingly, the Government may have certain rights in the invention.

FIELD OF THE INVENTION

The present invention relates generally to an altered vertebrate telomeric repeat binding factor (A-TRF) that alters the binding of a telomeric repeat binding factor (TRF) to a telomere repeat sequence, to the nucleotide acids encoding the A-TRFs, and to therapeutic methods of use thereof. The A-TRFs have a particular use in counteracting the telomere shortening associated with aging and certain diseases such as ataxia telangiectasia.

BACKGROUND OF THE INVENTION

Telomeres are terminal structural elements found at the end of chromosomes [Muller, *The Collecting Net-Woods Hole*, 13:181–195 (1939)] that protect natural double-stranded DNA ends from degradation, fusion, and recombination with chromosome-internal DNA [McClintock, *Genetics*, 26:234–282 (1941); Lundblad et al., *Cell*, 87:369–375 (1996)]. Telomeres are also thought to play a role in the architecture of the nucleus [Agard et al., *Nature*, 302:676–681 (1983); Rabl, *Morphol. J*, 10:214–330 (1885)], and to provide a solution to the end-replication problem that arises as a consequence of successive replication of linear DNA by DNA polymerases which would otherwise result with progressively shorter terminal sequences [Watson, *Nature*, 239:197–201 (1972)]. In tetrahymena, impaired telomere function leads to a defect in cytokinesis and to cell death [Yu et al., *Nature*, 344:126–132 (1990)]. Similarly, in yeast, loss of a single telomere results in cell cycle arrest and chromosome instability [Sandell and Zakian, *Cell*, 75:729–741 (1993)] and cells undergoing generalized telomere shortening eventually senesce [Lundblad and Szostak, *Cell*, 57:633–643 (1989); Singer and Gottschling, *Science*, 266:404–409 (1994)].

A ribonucleoprotein reverse transcriptase, telomerase, can elongate telomeres using an internal RNA component as template for the addition of the appropriate G-rich sequence to the 3' telomere termini [Greider and Blackburn, *Cell*, 43:405–413 (1985)]. This activity is thought to compensate for the inability of polymerases to replicate chromosome ends, but other mechanisms of telomere maintenance may operate as well [Pluta et al., *Nature*, 337:429–433 (1989)].

Telomeres contain a tandem array of repeat sequences, typically five to eight base pairs long, that are G-rich in the strand that extends to the end of the chromosome DNA. These repeat units appear to be both necessary and sufficient for telomere function [Lundblad et al., 1989, supra; Szostak et al., *Cell*, 36:459–568 (1982)]. All telomeres of a single genome are composed of the same repeats and these sequences are highly conserved across species. For instance, Oxytricha chromosomes terminate in TTTMGGGG repeats [Klobutcher et al., *Proc. Natl. Acad. Sci. USA*, 78:3015–3019 (1981)], Tetrahymena utilizes an array of $(TTGGGG)_n$. [Blackburn et al., *J. Mol. Biol.*, 120:33–53 (1978)], and plant chromosomes carry the sequence $(TTTAGGG)_n$ [Richards et al., *Cell*, 53:127–136 (1988)].

Telomeres of trypanosomes and all vertebrates, including mammals, contain the repeat sequence TTAGGG [Blackburn et al., *Cell*, 36:447–458 (1984); Brown, *Nature*, 338:774–776 (1986); Cross et al., *Nature*, 338:771–774 (1989); Moyzis et al., *Proc. Natl. Acad. Sci. USA*, 85:6622–6626 (1988); Van der Ploeg et al., *Cell*, 36:459–468 (1984)]. This 6 bp sequence is repeated in long tandem arrays at the chromosome ends, which may be as long as 100 kb in the mouse, and varies from 2 to 30 kb in humans [Zhong et al., *Mol. Cell. Biol.*, 13:4834–4943 (1992)].

During the development of human somatic tissue, telomeres undergo progressive shortening; in contrast, sperm telomeres increase with donor age [Broccoli et al., *Proc. Natl. Acad. Sci. USA*, 92:9082–9086 (1995); de Lange, *Proc. Natl. Acad. Sci. USA*, 91:2882–2885 (1994)]. Most if not all human somatic tissue chromosomes lose terminal TTAGGG repeats with each division, e.g., about 15–40 bp per year in the skin and blood. It is unclear what effect this diminution has since human telomeres are between 6–10 kb at birth. On the other hand, it is not yet known how many kilobases of TIAGGG repeats are necessary for optimal telomere function.

Primary human fibroblasts grown in culture lose about 50 bp of telomeric DNA per doubling (PD) before they stop dividing at a senescence stage [Allsopp et al., *Proc. Natl. Acad. Sci. USA*, 89:10114–10118 (1992)]. Importantly, there is an excellent correlation between the number of divisions that the cells go through and their initial telomere length. Indeed, it has been suggested that the correlation represents a molecular clock, which limits the potential of primary cells to replicate [Harley et al., *Nature* (London), 345:458–460 (1990); Harley et al., *Exp. Gerontol*, 27:375–382 (1992)]. Thus, immortalization of human somatic cells appears to involve a mechanism to halt telomere shortening. Recently Bodner et al. [*Science*, 279:349–352 (1998)] have reported a direct correlation between the introduction of telemorase into a cell and the proliferative life-span of the cell.

Changes in telomeric dynamics also appear to play a role in the malignant transformation of human cells [Broccoli et al., 1995, supra]. For example, telomeres of tumor cells are generally significantly shorter than those of the corresponding normal cells. Telomerase activation appears to be an obligatory step in the immortalization of human cells and in particular, in ovarian carcinoma [de Lange, 1994, supra]. Hanish et al. [*Proc. Natl. Acad. Sci. USA*, 91:8861–8865 (1994)] examined the requirements for the formation of human telomeres from TTAGGG seeds, and found that telomere formation was not correlated with the ability of human telomerase to elongate telomeric sequences in vitro, and did not appear to be a result of homologous recombination. Rather, the sequence dependence of telomere formation matched the in vitro binding requirements for TRF, a telomeric TTAGGG repeat binding protein that is associated with human and mouse telomeres in interphase and in mitosis.

Indeed, the only known protein components of mammalian telomeres are the TRF proteins, duplex TTAGGG repeat binding factors that are localized at telomeres in interphase and metaphase chromosomes [Zhong et al., 1992, supra; Chong et al., *Science*, 270:1663–1667 (1995); Ludérus et al., *J. Cell Biol.*, 135:867–881 (1996); Broccoli et al., *Hum. Mol. Genetics*, 6:69–76 (1997); see Smith and de Lange, *Trends in Genetics*, 13:21–26 (1997) for review]. Human TRF1 (hTRF1) is a low-abundance activity found in nuclear extracts from all human cells and tissues and a similar activity is present in other vertebrates [Zhong et al., 1992, supra; Chong et al., 1995, supra (U.S. patent application Ser. No. 08/519,103 filed Aug. 25, 1995, hereby incorporated by reference in its entirety)]. TRF2 (also referred to as orf2) has been identified as a TRF1 homolog. [Bilaud et al., *Nucl. Acids Res.*, 24:1294–1303 (1996) (U.S. patent application Ser. No. 08/938,052 filed Sep. 26, 1997, hereby incorporated by reference in its entirety)]. Similar duplex telomeric DNA binding proteins in yeasts have been implicated in telomere length control, telomere stability, and telomeric silencing [reviewed in Shore, *Trends Gen.*, 10:408–412 (1994); Zakian, *Saccharomyces telomere. function, structure and replication*, Cold Spring Harbor Laboratory Press, Cold Spring Harbor, pp. 107–138 (1995a); see also McEachern and Blackburn, *Nature*, 376:403–409 (1995); Krauskopf and Blackburn, *Nature*, 383:354–357 (1996)].

TRF1 has DNA binding properties in vitro that are consistent with its presence along the double-stranded telomeric repeat array at chromosome ends. TRF1 binds efficiently to arrays of duplex TTAGGG repeats, irrespective of the presence of a DNA terminus [Zhong et al., 1992, supra]. Single-stranded telomeric DNA is not an effective TRF1 substrate and neither are heterologous telomeric sequences, such as double-stranded arrays of TTGGGG, TTAGGC, TTTAGGG, TTAGGGGG, and TAGGG repeats [Zhong et al., 1992, supra; Hanish et al., 1994, supra; Chong et al., 1995, supra]. This sequence specificity of TRFs match the sequence requirements for de novo telomere formation in human cells, suggesting that TRF proteins are involved in this process [Hanish et al., 1994, supra].

Interestingly, TRF1 binding is stimulated by longer repeat arrays with 6 or 12 repeat providing a better binding substrate than 3 repeats [Zhong et al., 1992, supra]. Since DNA fragments with 3, 6, or 12 telomeric repeats each bind exactly the same protein mass, this enhancement is not due to cooperative interactions between multiple TRF1 binding units. The minimal TRF1 binding site and the mechanism by which this protein differentiates between telomeric arrays of different length remain to be deter-mined.

Mouse and human TRF1 are novel proteins with three recognizable domains: an acidic domain at the N-terminus, a conserved TRF-specific domain, and a C-terminal domain with strong homology to the DNA binding domain of Myb oncoproteins (see FIG. 1; [Chong et al., 1995, supra; U.S. patent application Ser. No. 08/519,103 filed Aug. 25, 1995]). c-Myb oncoproteins are transcriptional activators that carry three imperfect 50 amino acid repeats, two of which are required for DNA binding. In c-Myb, the two Myb repeats fold into helix-turn-helix motifs that are closely packed on the DNA such that their recognition helices together contact a single short PyAACNG site [Ogata et al., *Cell*, 79:629–648 (1994)]. In other Myb-related DNA binding proteins, Myb repeats have been found in four configurations: three tandem repeats (for instance, in the yeast protein BAS1 [Hovring et al., *J. Biol. Chem.*, 296:17663–17669 (1994)]), two tandem repeats (in many plant transcription factors [Ramachandran et al., *Curr. Op. Genet. Dev.*, 4:642–646 (1994)]), and in the fission yeast protein cdc5 [Ohi et al., *EMBO J.*, 13:471–483 (1994)], two repeats separated by a linker (in the yeast proteins Reb1p and Rap1p (Repressor/Activator protein 1) and in the mouse protein MIDA1 [Morrow et al., *Mol. Cell. Biol.*, 13:1173–1182 (1993); Konig et al., *Cell*, 85:125–136 (1996); Sitzmann et al., *Oncogene*, 12:1889–1894 (19 96)]; and single Myb repeats (in several yeast, plant, Drosophila, and mouse proteins [England et al., *Proc. Natl. Acad. Sci. USA*, 89:683–687 (1991); Brigati et al., *Mol. Cell. Biol.*, 13:1306–1314 (1993); da Costa e Silva et al., *The Plant Journal*, 4:125–135 (1993); Baranowskij et al., *EMBO J.*, 13:5383–5392 (1994); Lugert and Werr, *Plant Molecular Biology*, 25:493–506 (1994); Stokes and Perry, *Mol. Cell. Biol.*, 15:2745–2753 (1995)].

The group of proteins with one Myb repeat, which includes TRF1 and TRF2, had presented a conundrum, since in other Myb-related factors at least two Myb repeats are required for DNA binding [Henry et al., *Proc. Natl. Acad. Sci. USA*, 18:2617–2623 (1990); Saikumar et al., *Proc. Natl. Acad. Sci. USA*, 87:8452–8456 (1990); Hovring et al., 1994, supra].

Remarkably, TRF1 evolved rapidly [Broccoli et al., 1997, supra] and does not show significant amino acid identity with Rap1p, the major duplex telomeric DNA binding protein of the yeasts *Saccharomyces cerevisiae* [Shore, 1994, supra] and *Kluyveromyces lactis* [Larson et al., *Gene*, 150:35–41 (1994); Krauskopf and Blackburn, 1996, supra]. Yet, the yeast and mammalian telomeric proteins appear to be distantly-related, since both carry Myb-related DNA binding domains [Konig et al., 1996, supra]. Rap1p contains two Myb repeats, which, separated by a 40 amino acid linker, dock onto two GGTGT sequences that are separated by 3 bp. Since Rap1p and c-Myb bind DNA differently (Ogata et al., 1994, supra; Konig et al., 1996, supra), no a priori predictions can be made on the DNA binding mode of TRF1 and TRF2. Indeed the fact that TRF1 and TRF2 contain only a single Myb motif [Chong et al., 1995, supra] points to a crucial difference in the way these factors bind to DNA compared with c-Myb and Rap1p.

Mammalian telomeres show a species-specific length setting suggesting a regulatory mechanism that controls telomere length in the germline. Telomere length control is also evident from the stability of telomeres in telomerase expressing cells lines and from the observation that newly-formed telomeres acquire a length appropriate for the host cell. The latter observation suggests that cells monitor and modulate the length of individual telomeres, a process likely to involve a protein such as a TRF, that binds to the duplex telomeric repeat region at mammalian chromosome ends.

Therefore, there is a need to identify agents that can modify and/or control telomere lengthening and/or telomere maintenance. More particularly, there is a need to identify an agent that can modify or/inhibit the activity of TRFs either individually, such as an inhibitor to TRF1 or TRF2 or a more general agent that inhibits two or more TRFs. Furthermore, there is a need to characterize such an agent.

The citation of any reference herein should not be construed as an admission that such reference is available as "Prior Art" to the instant application.

SUMMARY OF THE INVENTION

The present invention provides an isolated altered vertebrate telomere repeat binding factor (A-TRF) that impedes a telomere repeat binding factor (TRF) from binding to its specific telomere repeat sequence. The A-TRF of the present invention minimally contains a functional portion of the TRF dimerization domain and forms a heterodimer with a TRF. In preferred embodiments the telomere repeat sequence is TTAGGG. The present invention also includes the corresponding nucleic acids that encode the A-TRFs of the present invention, as well as the heterodimers formed by the association of an A-TRF with a TRF.

A heterodimer formed by the association of a TRF with an A-TRF of the present invention has a measurably lower binding affinity for the TRF telomeric repeat sequence than does the corresponding TRF homodimer. Preferably there is at least a two-fold lower binding affinity, and more preferably there is at least a ten-fold lower binding affinity. In the most preferred embodiment the heterodimer does not bind to the telomeric repeat sequence at all. Thus the A-TRF hinders and/or prevents the binding of TRF to its telomere repeat sequence binding site. One embodiment of the present invention is an A-TRF that is an altered TRF1, A-TRF1 which can form a heterodimer with TRF1. A particular embodiment of this type is a human A-TRF1. Another embodiment is an altered TRF2. In a particular embodiment of this type the A-TRF2 is human A-TRF2.

The present invention provides A-TRFs in a variety of forms, all of which are included in the present invention, along with all of the nucleic acids that encode these A-TRFs. For example an A-TRF can be a truncated TRF. One particular A-TRF is a truncated TRF1 that has an amino acid sequence selected from the group consisting of SEQ ID NO:6, and SEQ ID NO:6 comprising a conservative substitution thereof. In another such embodiment, the A-TRF is a truncated TRF2 that has an amino acid sequence of SEQ ID NO:14 or SEQ ID NO:14 comprising a conservative substitution thereof. The nucleic acids that encode such A-TRFs are included in the present invention, including the isolated nucleic acid having a nucleotide sequence of SEQ ID NO:2, which encodes a A-TRF1, and the isolated nucleic acid having a nucleotide sequence of SEQ ID NO:13 which encodes a A-TRF2.

In another example, the A-TRF can contain a dysfunctional DNA binding domain. In one such embodiment, the A-TRF contains a deletion in the amino acid sequence of the DNA binding domain. In another such embodiment the A-TRF contains an insertion in the amino acid sequence of the DNA binding domain that disrupts DNA binding. In still another embodiment, the A-TRF contains a non-conservative amino acid substitution in the amino acid sequence of the DNA binding domain that disrupts DNA binding. The nucleic acids that encode such A-TRFs are also included in the present invention.

The present invention also includes an A-TRF that contains a substitute DNA binding domain, i.e., a DNA binding domain that is not a TRF DNA binding domain. In one such embodiment, the substitute DNA binding domain is an alternative Myb DNA binding domain. In a particular embodiment of this type, the A-TRF has an amino acid sequence selected from the group consisting of SEQ ID NO:7, and SEQ ID NO:7 comprising a conservative substitution thereof. The nucleic acids that encode such A-TRFs are included in the present invention, including the isolated nucleic acid having a nucleotide sequence of SEQ ID NO:3.

Yet another example of an A-TRF of the present invention is a TRF having a deletion, an insertion, or a non-conservative amino acid substitution in a region of the TRF outside of the dimerization domain that adversely effects the ability of a heterodimer formed between such an A-TRF and a TRF to bind to its specific telomere repeat sequence. In one particular embodiment of this rype, the A-TRF has an amino acid sequence selected from the group consisting of SEQ ID NO:8, and SEQ ID NO:8 comprising a conservative substitution thereof. The nucleic acids that encode such A-TRFs are included in the present invention, including the isolated nucleic acid having a nucleotide sequence of SEQ ID NO:4.

The dimerization domain of a TRF is included in the present invention. A polypeptide consisting of the dimerization domain can also function as an A-TRF. In one specific embodiment the A-TRF is an A-TRF1 and the dimerization domain has an amino acid sequence selected from the group consisting of SEQ ID NO:11, and SEQ ID NO:11 comprising a conservative substitution thereof. In another embodiment the A-TRF is an A-TRF2 and the dimerization domain has an amino acid sequence of SEQ ID NO:23, or SEQ ID NO:23 comprising a conservative substitution thereof. The nucleic acids that encode such dimerization domains are included in the present invention, including the isolated human nucleic acid having a nucleotide sequence of SEQ ID NO:9, and SEQ ID NO:22 for example. Dimerization domains from other species for TRF2 and TRF1 are included in U.S. patent application Ser. No. 08/938,052 filed Sep. 26, 1997 (hereby incorporated herein by reference in its entirety) which are also contemplated by the present invention.

The present invention, also includes specific antibodies that react with an A-TRF, but do not cross-react with a TRF. The antibodies are raised against A-TRFs purified from natural or recombinant sources, or produced by chemical synthesis, and derivatives or analogs thereof, including fusion proteins. Such antibodies include but are not limited to polyclonal, monoclonal, chimeric, single chain, Fab fragments, and a Fab expression library. These antibodies may be labeled. Also included is an immortal cell line that produces a monoclonal antibody of the present invention.

The nucleic acids encoding the A-TRFs of the present invention can be DNA, and cloning vectors that comprise such DNAs are therefore also included. Nucleic acids encoding an A-TRF of the present invention can also contain a heterologous nucleotide sequence. Expression vectors which comprise DNA encoding an A-TRF, and which are operatively associated with an expression control sequence, are also included. In addition, the present invention contains unicellular hosts that are transfected or transformed with the expression vectors of the present invention. In one such embodiment the unicellular host is a bacterium. The present invention also includes mammalian cells transfected or transformed with the expression vector of the present invention.

The present invention also includes a nucleic acid encoding a DNA binding domain of a vertebrate telomere repeat binding factor (TRF) having an amino acid sequence selected from the group consisting of SEQ ID NO:12, and SEQ ID NO:12 comprising a conservative substitution thereof.

Pharmaceutical compositions comprising an A-TRF and a pharmaceutically acceptable carrier are also included in the present invention. Such pharmaceutical compositions may be used to aid in counteracting the telomere shortening associated with aging or with a disease, i.e. a composition containing an A-TRF1, or alternatively can be used as an anti tumor agent, i.e. a composition containing an A-TRF2. One such embodiment includes a telomerase stimulating drug along with an A-TRF and a pharmaceutically acceptable carrier. Another embodiment includes telomerase along with an A-TRF and a pharmaceutically acceptable carrier. In yet another embodiment, both telomerase and a telomerase stimulating drug are included with an A-TRF and a pharmaceutically acceptable carrier. When the A-TRF is A-TRF1, such embodiments may be used specifically to treat ataxia telangiectasia, and/or Downs Syndrome. A related feature of this aspect of the invention is the use of such embodiments to counteract the aging process. In particular, such treatment can be used in cosmetic therapy. In addition, the A-TRF1s of the present invention can also be used to prevent and/or treat (1) atrophy of the skin through loss of extracellular matrix homeostasis in dermal fibroblasts [Takeda et al., *Arch. Dermatol.*, 130:87 (1994); (2) age-related macular degeneration [Boulton et al., *J. Neurosci.*, 15:4992 (1995)]; and (3) atherosclerosis [Kamazaki et al.,*J. Med. Sci.*, 42:97 (1993)]. In such embodiments, the A-TRF1 (or nucleic cid encoding the same) can be administered alone or together with telomerase or a telomerase mimic or agonist [See also, Bodner et al., *Science*, 279:349–352 (1998)]. Alternatively, the demonstration that A-TRF2 administration can lead to inhibition of tumor cell growth (Example 3) indicates that a pharmaceutical composition comprising an A-TRF2 can be used in an anti-tumor therapy.

In a preferred embodiment a pharmaceutical composition that aids in counteracting the telomere shortening associated with aging and/or disease contains a pharmaceutically acceptable carrier along with an A-TRF having an amino acid sequence selected from the group consisting of SEQ ID NO:6, and SEQ ID NO:6 comprising a conservative substitution thereof.

The present invention also includes methods of counteracting the telomere shortening associated with aging and/or disease that comprises administering a therapeutically effective amount of a pharmaceutical composition containing an A-TRF1 of the present invention to an animal subject. Similarly, methods of counteracting telomere maintenance in a diseased cell, e.g. viral-infected cell or tumor cell, comprising administering a therapeutically effective amount of a pharmaceutical composition containing an A-TRF2 of the present invention to an animal subject are included in the present invention. In one particular embodiment of this method, the animal subject is a mammal. In a preferred embodiment of this type, the mammal is a human. Any of the pharmaceutical embodiments comprising A-TRF1s or A-TRF2s of the present invention may be suitable for their respective uses.

The present invention also includes methods of producing an A-TRF. In one embodiment, an expression vector comprising a nucleic acid encoding an A-TRF is introduced into a cell. The cell is then cultured under conditions that allow the A-TRF to be expressed. In one such embodiment, the cell is a bacterial cell. In yet another embodiment, the cell is an insect cell. In still another such embodiment, the cell is a mammalian cell. Human A-TRFs of the present invention may also be inserted into a non-human mammal, such as a mouse or pig, and be expressed transgenically. Methods of purifying the expressed A-TRFs of the present invention are also included, as are the products isolated from such procedures.

The present invention also includes methods of identifying an A-TRF. In one such embodiment a candidate A-TRF is contacted with a TRF under conditions where heterodimer formation occurs. The binding of TRF to a specific nucleic acid is then determined. A candidate A-TRF is identified as an A-TRF on the basis of the heterodimer having a relative affinity for the specific nucleic acid that is measurably less than that of the corresponding TRF homodimer. Preferably there is at least a two-fold lower binding affinity. More preferably at least a ten-fold lower binding affinity is observed. In the most preferred embodiment, the heterodimer does not bind to the telomeric repeat sequence at all.

In one embodiment the binding of TRF to a specific nucleic acid is determined with a gel-shift assay. In another embodiment the binding of TRF to a specific nucleic acid is determined with a SouthWestern assay. In still another embodiment the binding of TRF to a specific nucleic acid is determined with a nitrocellulose filter-binding assay. In a yet another embodiment, the ability of TRF to bend a DNA probe is determined. In a preferred embodiment the specific nucleic acid comprises a telomere repeat binding sequence of the TRF.

Methods of identifying an A-TRF of the present invention include those where both the TRF and the A-TRF are expressed in an in vitro transcription/translation system. In one such embodiment, a labeled nucleic acid is used as a probe. In an alternative embodiment of the present invention, the TRF and the A-TRF are co-expressed in situ in a cell culture system. In one such embodiment the TRF and the A-TRF are co-expressed in a vertebrate cell. In a particular embodiment of this type, the binding of TRF to a specific nucleic acid is performed by determining the ability of a candidate A-TRF to inhibit the co-localization of TRF with telomeric DNA. A candidate A-TRF is identified as an A-TRF if the co-localization of TRF with telomeric DNA co-expressed in the presence of the candidate A-TRF is measurably less than that of TRF expressed in the absence of the candidate A-TRF. In preferred embodiments of this type the vertebrate cell is a HeLa cell.

The present invention also includes drug screening assays to identify drugs that mimic and/or complement the effect of the A-TRFs. One such aspect of the invention includes a method of selecting a drug that specifically interferes with the formation of a TRF homodimer, or A-TRF-TRF homodimer. In one embodiment of this type, a candidate drug is contacted with a TRF, or a fragment thereof, or an A-TRF under conditions where the TRF, or the fragment thereof, or the A-TRF dimerizes in the absence of the candidate drug. The amount of dimer formed is determined. A drug is selected on the basis that the dimer formed in the presence of the drug is measurably less than that formed in the absence of the drug. The determination can be made in any of a number of ways including as an absolute amount of dimer, or as a percentage of monomer paired in dimers relative to the total monomer present. In one embodiment the absolute amount of dimer formed is determined and a drug is selected when there is at least a two-fold decrease in that absolute amount of dimer formed in the presence of the drug. In a more preferred embodiment of this type, at least a ten-fold decrease in the absolute amount of dimer formed is determined in the presence of the drug. In the most preferred embodiment no measurable dimer is formed in the presence of the drug. These drugs can be used in pharmaceutical compositions and methods described above either in place of the A-TRF or combined with an A-TRF to counteract telomere shortening associated with aging and/or disease.

Yet another aspect of the invention includes an assay for identifying analogues e.g. drugs, that mimic the DNA bending activity of a vertebrate TRF homodimer. This assay takes advantage of the DNA bending properties of the vertebrate TRF homodimer, which can be detected as a retardation in the migration of specific labeled DNA probes bound to a TRF homodimer. In one such embodiment, labeled DNA probes consisting of variable TTAGGG repeat arrays, e.g. 6mers or 12mers, are incubated with candidate compounds and the mobility of the resulting complexes are analyzed on native polyacrylamide or agarose gels. Candidate compounds that cause retardation in the migration of the labeled DNA probe are selected as analogues. In one particular embodiment of this type, the analogues are potential drugs that can be used to inhibit telomere elongation. Such drugs can be used for example, either alone or in tandem with telomerase inhibiting drugs in cancer therapy.

Accordingly, it is a principal object of the present invention to provide inhibitors of TRFs. Such inhibitors can promote telomere elongation and/or retard telomere shortening in a vertebrate cell, or alternatively can prevent the maintenance of the correct structure at telomere termini.

It is a further object of the present invention to provide a purified A-TRF that binds to a TRF, and thereby counteracts the effect of TRF by interfering with the binding of TRF to its telomere repeat sequence.

It is a further object of the present invention to provide structural characteristics and properties of a purified A-TRF, including the nucleic acid and amino acid sequences.

It is a further object of the present invention to provide an antibody specific for an A-TRF that binds to the A-TRF but does not bind to a TRF. It is a further object of the present invention to provide a method of producing an A-TRF, including through modification of a TRF, and through recombinant technology.

It is a further object of the present invention to provide a method of selecting an A-TRF from putative A-TRFs on the basis of binding to a TRF and/or inhibiting a TRF from associating with its telomere repeat sequence.

It is a further object of the present invention to provide a method of designing putative A-TRFs through altering the amino acid and/or nucleic acid sequences of a TRF.

It is a further object of the present invention to provide a method of screening drug libraries for agents that mimic or supplement A-TRF activity by interfering with a TRF from binding to a specific nucleic acid sequence.

It is a further object of the present invention to provide a method of treating a condition that involves telomere shortening, such as ataxia telangiectasia, Downs Syndrome, cancer, and aging.

It is a further object of the present invention to provide a method of treating a condition that would be helped by promotion of cell senescence.

These and other aspects of the present invention will be better appreciated by reference to the following drawings and Detailed Description.

BRIEF DESCRIPTION OF THE DRAWINGS

FIGS. 1A–1C. Tetracycline-regulated expression of TRF1 alleles in HT1080 cells. FIG. 1A depicts a schematic representing the domain structure of TRF1 and the alleles used in this study. FIGS. 1B and 1C depict Western analysis of TRF1 expression in clonal HT1080tTA cells transfected with the TRF1 alleles shown in FIG. 1A. Cells were grown with or without doxycycline (uninduced and induced, respectively) and whole cell lysates were analyzed by Western blotting using an antibody against the acidic N-terminal domain of TRF1 (Ab 371C2) in FIG. 1B or an anti-FLAG monoclonal FIG. 1C. Endogenous HT1080 TRF1 is represented by a doublet of which the top band co-migrates with the transfected full length protein (lane 4 in FIG. 1B). The bottom band of the doublet is likely to represent an alternatively spliced form of TRF1 which lacks an exon encoding 20 amino acids in the non-conserved region of the protein located between the dimerization domain and the Myb domain.

FIG. 2A depicts an SDS PAGE which shows $^{35}$S-methionine labelled in vitro translation products obtained with full length TRF1 having an amino acid sequence of SEQ ID NO:5, and TIF1$^{66-385}$ each alone and as mixtures created by co-translation of a constant amount of full length TRF1 and an increasing amount of TRF1$^{66-385}$. FIG. 2B depicts the gel-shift analysis of the TTAGGG repeat binding activity obtained with unlabelled proteins synthesized in parallel with the experiment in FIG. 2A. FIGS. 2C–2E depict the co-localization of endogenous TRF1 with telomeric DNA in HeLa interphase nuclei. FIG. 2C depicts the detection of endogenous TRF1 with polyclonal antibody Ab371C2 (directed against the acidic N-terminus of TRF1) and a FITC-conjugated donkey anti-rabbit antibody (green). In FIG. 2D telomeric DNA was visualized in the same nuclei by fluorescence in situ hybridization of a digoxigenin-labelled [CCCUAA]$_{27}$ RNA followed by sheep anti-digoxigenin and TRITC conjugated donkey anti-sheep IgG (red). In FIG. 2E a superimposition of the images in FIGS. 2C and 2D is shown. White and yellow indicates co-localization of TRF1 with telomeric DNA. Control experiments indicated that there was no cross-reactivity between the antibodies used. FIGS. 2F and 2G demonstrate that overexpression of A-TRF1$^{66-385}$ inhibits binding of endogenous TRF1 to telomeres. HeLa cells transiently co-transfected with the tTA expression construct and the A-TRF1$^{66-385}$ construct were stained with a monoclonal antibody against the FLAG tag (M2) followed by a FITC-labelled donkey anti-mouse antibody (green). FIG. 2G shows the same cells stained for endogenous TRF1 with Ab371C2 and donkey anti-rabbit Cy3 (red). DAPI was used to stain DNA in FIGS. 2C through 2G (blue).

FIGS. 3A–3C. Telomere length changes in response to TRF1. FIGS. 3A–3C depict blots of HinfI digested genomic DNA from three clonal HT1080tTA cell lines (A, B6; B, D4; C, K10) carrying the indicated TRF1 alleles. Each cell line was passaged for 124 PDs in the presence (uninduced) or absence (induced) of doxycycline and DNA samples were analyzed at the indicated PDs. The blots were probed with a TTAGGG repeat probe to detect telomeric restriction fragments.

FIG. 6A depicts a schematic representation of the two hTRF1 derivatives (I and II) that differed in size by approximately 26 kDa. Form I contains the 26-kDa GFP protein fused to the N-terminus of hTRF1. Form II contains an N-terminal addition of 43 amino acids encoded by polylinker sequences. in vitro translation of the TRF1 derivatives depicted in FIG. 6A. FIG. 6C depicts a gel-shift assay with TRF1 derivative I (lane 2), TRF1 derivative II (lane 5), or a mixture of the two (lanes 3 and 4). The probe is a restriction fragment containing the sequence [TTAGGG]

Figure 2A:
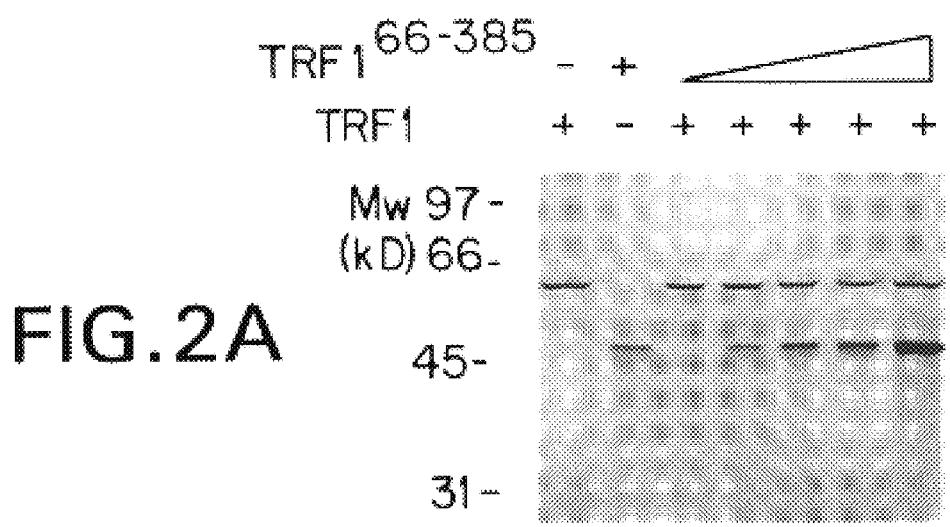
FIGS. 2A–2G. Characterization of the dominant interfering activity of the altered TRF, A-RF1$^{66-385}$, having an amino acid sequence of SEQ ID NO:6.

12. For the reactions in lanes 3 and 4 the TRF1 derivatives were produced by co-translation. The ratio of plasmids used in the coupled transcription/translation reaction was 1:1 for lane 3 and 1:2 (excess of hTRF1 derivative II) for lane 4. Lane 1 represents a reaction with mock in vitro translation product. The protein composition of the gel-shift complexes are indicated to the right of the gel.

FIG. 7. Identification of the dimerization domain of TRF1 using the two-hybrid system. β-galactosidase levels were measured for strains containing plasmids expressing various LexA-TRF1 hybrid genes (as indicated) along with plasmids expressing either the GAL4 activation domain (GAD) or GAD fusions containing full length or truncated (Δ320-C) TRF1. The values represent an average of three independent transformants. Values below 0.01 are indicated by 0; n.d.= not determined.

FIGS. 8A–8D. Deletion mapping of the sequences in TRF1 required for DNA binding. FIG. 8A depicts a schematic of the deletion mutants used and summary of their DNA binding activity. FIGS. 8B and 8C depict gel-shift reactions with the indicated TRF1 derivatives. FIG. 8D depicts co-translation experiments showing that TRF1 requires two Myb repeats for DNA binding. Increasing amounts of Δ320-C were co-translated with full length hTRF1 and the mixtures were assayed for TTAGGG repeat binding activity. The gel-shift probe in FIGS. 8B-8D is a [TTAGGG]$_{12}$ containing restriction fragment. To ensure that each protein was present at the same concentration, the proteins were synthesized in parallel in the presence of $^{35}$S-methionine and the labelled products were analyzed on SDSlPAGE (shown above each of the gel-shift assays).

Figure 9A:
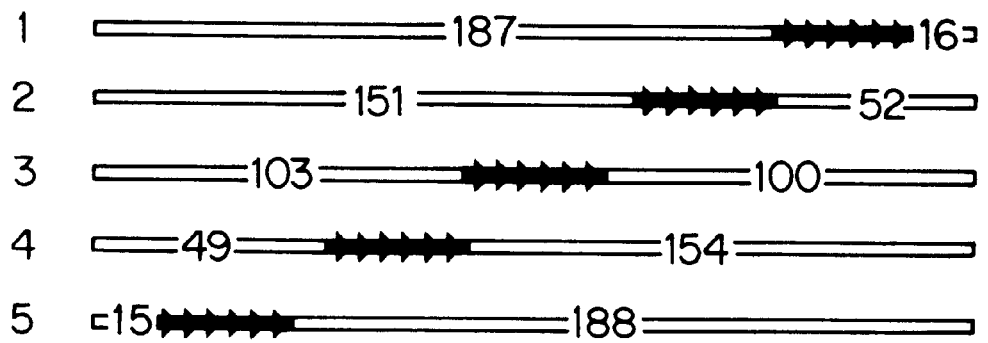
Figure 9C:
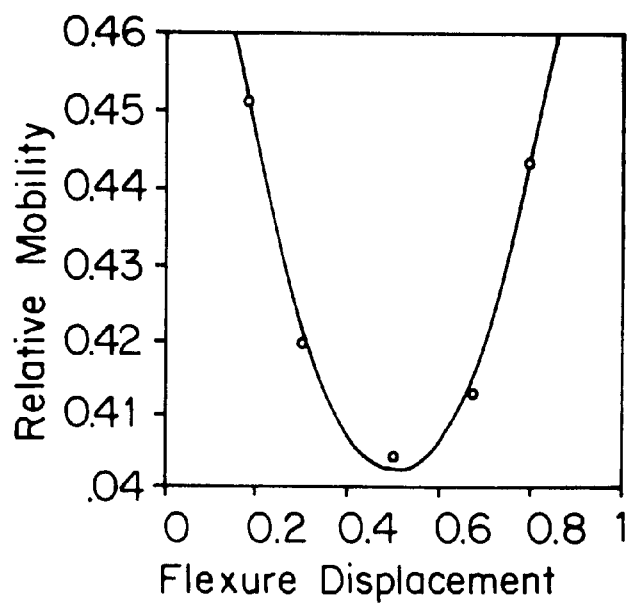

FIGS. 9A–9C. hTRF1 bends DNA. FIG. 9A depicts a schematic representation of two sets of five PCR-generated permuted gel-shift probes carrying either 3, 6, or 12 complete tandem TTAGGG repeats. The length of the non-telomeric sequences in each of the probes is indicated. FIG. 9B depicts a gel-shift assay with partially purified HeLa TRF1 and the labelled probes shown in FIG. 9A. The assay on the left side was performed with probes containing [TTAGGG]$_6$ sites with or without added unlabelled [TTAGGG]. competitor DNA as indicated. The assay on the right hand side was performed with probes containing [TTAGGG]$_{12}$ sites. FIG. 9C depicts a plot of the relative mobility (mobility of bound DNA/mobility of free DNA) of each of the TRF1 complexes against the flexure displacement in each probe. The data points represent probes 1–5 from right to left; values on the x-axis indicate the distance from the middle of the TTAGGG repeat site to the 5' end of the probe divided by the length of the probe. The data points were interpolated with the function derived by Ferrari [Ferrari et al., *EMBO J.*, 11:4497–4506 (1992)].

Figure 10A:
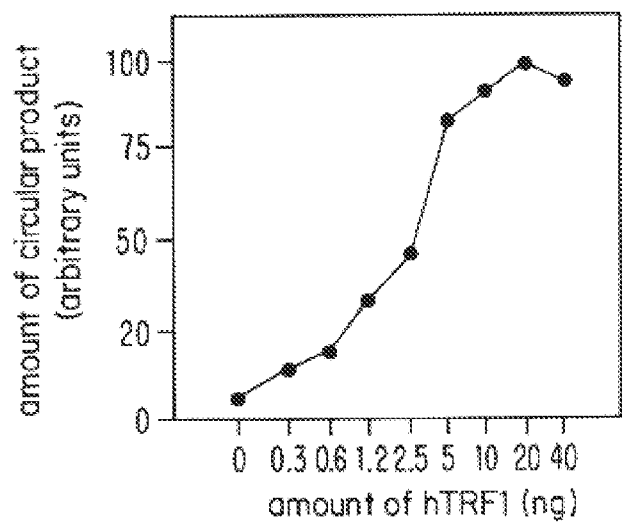
Figure 10B:
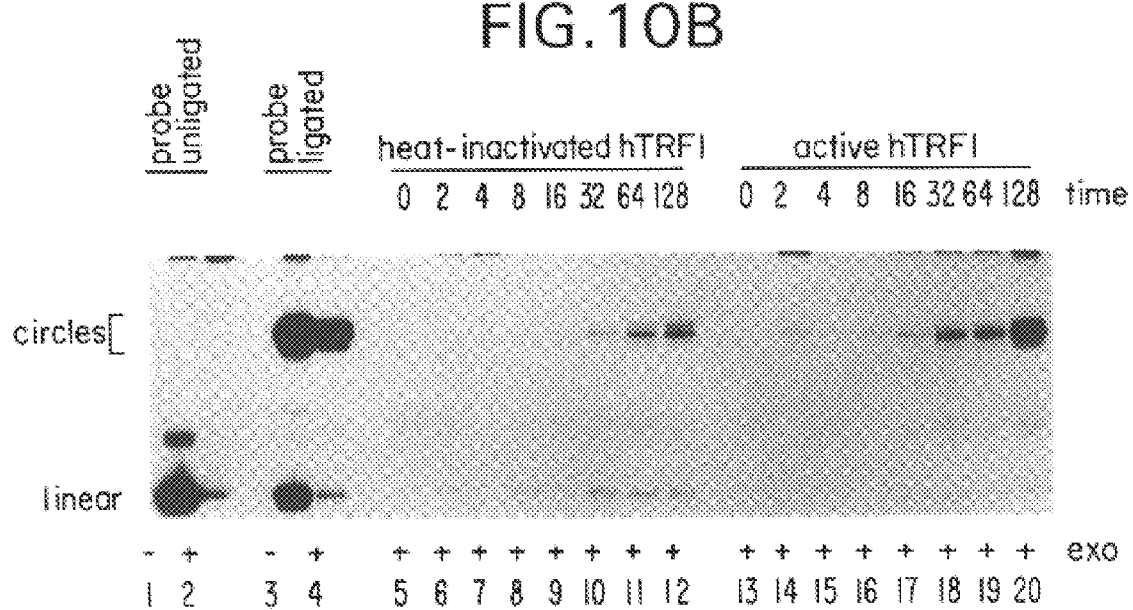

FIGS. 10A–10C. hTRF1 enhances DNA cyclization. FIG. 10A depicts the effect of increasing amounts of baculovirus-expressed hTRF1 on cyclization of a 217-bp DNA fragment containing 27 WTAGGG repeats. FIG. 10B depicts the rate of cyclization of the 217-bp DNA fragment that was measured in the presence of either heat-inactivated (lanes 5–12) or active (lanes 13–20) baculovirus-expressed hTRF1. Ligation time (in minutes) is indicated over lanes 5–20. Exonuclease digestion was performed as indicated prior to loading of samples in order to eliminate linear ligation products. Lanes 1 and 2 show unligated samples. In lanes 3 and 4, the fragment was ligated with a 20-fold higher concentration of ligase as compared to samples 5–20. Lane 4 is under-loaded due to loss of DNA after exonuclease digestion.

Figure 11:
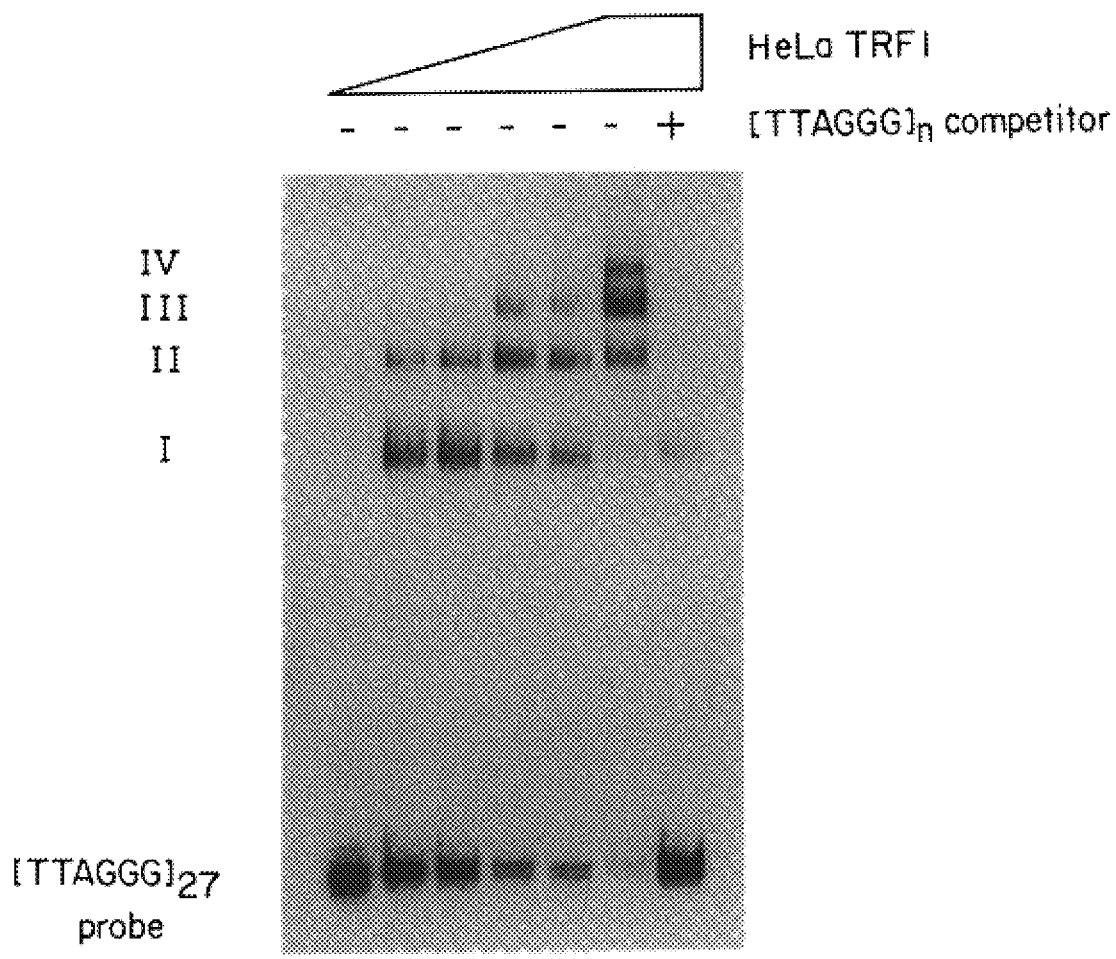

FIG. 11. hTRF1 dimers do not show strong cooperative interactions. Increasing amounts (1, 2, 3, 4, and 8 μl) of partially purified HeLa TRF was added to a labeled probe derived from plasmid pTH5 (de Lange et al., 1990) which carries 27 tandem TTAGGG repeats. Complexes containing 1–4 TRF1 dimers are identified to the left of the gel (Roman numerals). The first lane is a mock reaction in absence of hTRF1. Unlabelled TTAGGG repeat competitor DNA was added to the reaction in the last lane.

Figure 12A:
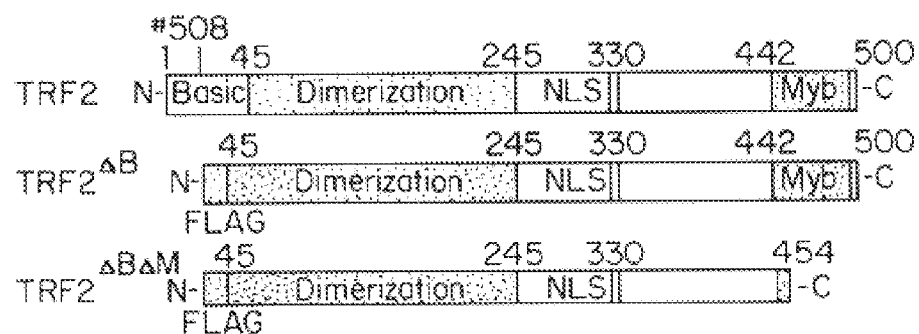
Figure 12B:
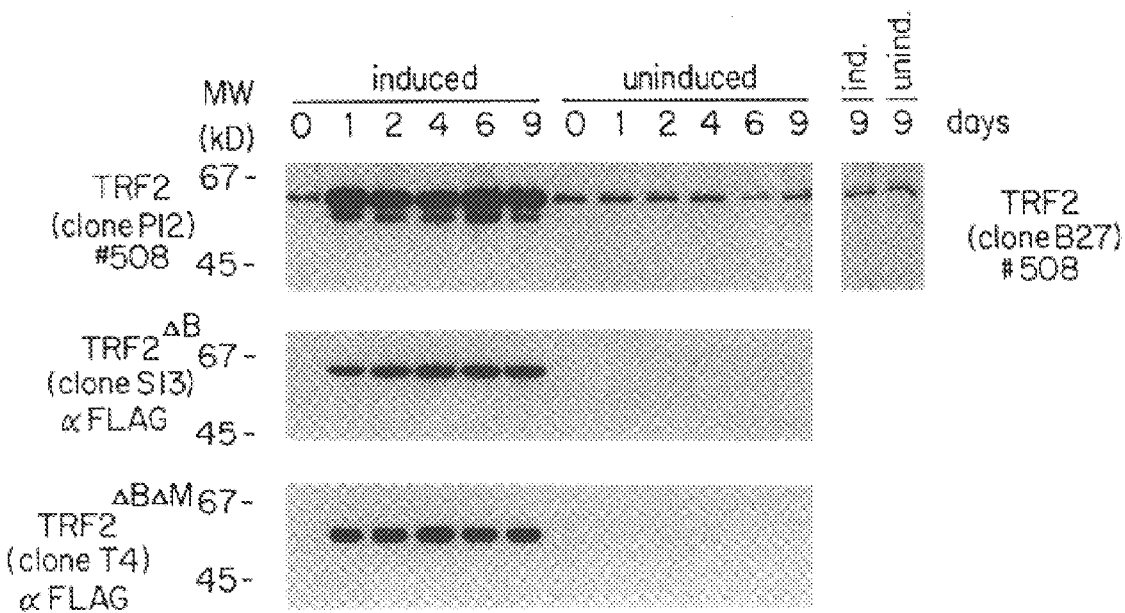

FIGS. 12A–12B. Inducible expression of TRF2 proteins in HTC75 cells. FIG. 12A depicts a schematic of full length human TRF2 [Broccoli et al., *Nature Gen.*, 17:231–235 (1997)] and the deletion mutants TRF2$^{\Delta B}$ and TRF2$^{\Delta B \Delta M}$. The approximate position of the peptide used to raise the polyclonal αTRF2 antibody #508 is indicated. The two TRF2 deletion mutants carry an N-terminal FLAG epitope.

FIG. 12B shows a Western analysis for the inducible expression of the three forms of TRF2 shown in FIG. 12A. Whole cell extracts were prepared from clonal HTC75-derived cell lines expressing the full length TRF2 (clone P12, having a nucleotide sequence of SEQ ID NO:17 which encodes the amino acid sequence of SEQ ID NO:18), TRF2$^{\Delta B}$ (clone S13, having a nucleotide sequence of SEQ ID NO:15 which encodes the amino acid sequence of SEQ ID NO:16), TRF2$^{\Delta B \Delta M}$ (clone T4, having a nucleotide sequence of SEQ ID NO:13 which encodes the amino acid sequence of SEQ ID NO:14), and control cell line B27, which contains the empty vector. Extracts were prepared from cells grown in parallel in the presence (uninduced) or absence (induced) of doxycyclin for the indicated time. For each extract 20 μg of protein was fractioned, blotted and incubated with the primary antibodies indicated in the Figure.

Figure 13A:
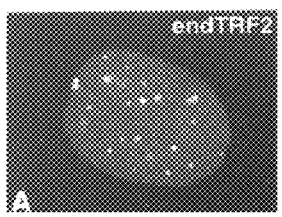
Figure 13B:
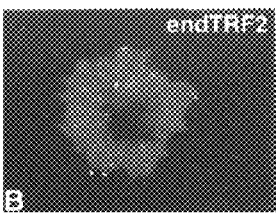

FIGS. 13A–13L. In vivo effects of the TRF2 mutants on telomere binding of endogenous wild-type TRF1 and TRF2 in transiently transfected HeLa cells. FIGS. 13A–B show the localization of endogenous wild-type TRF2 using antibody #508 (green/yellow) in an interphase nucleus (FIG. 13A) and on mitotic chromosomes (FIG. 13B) of HeLa cells. DNA was stained with DAPI (shown in red).

Figure 13C:
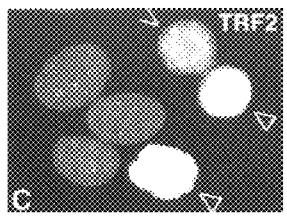
Figure 13D:
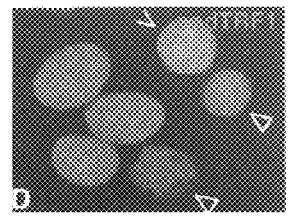
Figure 13E:
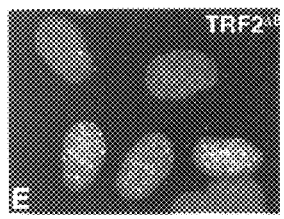

FIGS. 13C–13D show HeLa cells transiently transfected with wild-type TRF were dual-labeled for TRF2 using antibody #508 (green in FIG. 13C) and endogenous TRF1 using mouse serum #2 (end TRF1, red in FIG. 13D). Three transfected cells overexpressing TRF2 are indicated by arrowheads; the other three cells were probably not transfected and showed levels of endogenous TRF2 similar to untransfected control cells.

Figure 13F:
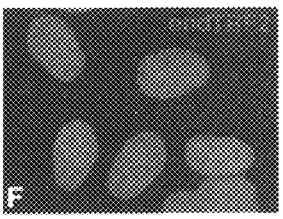
Figure 13G:
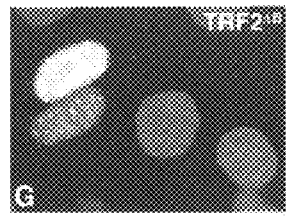
Figure 13H:
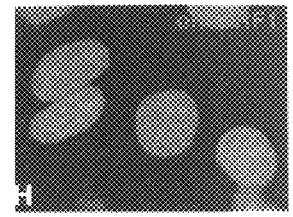

FIGS. 13E–13H show HeLa cells transiently transfected with TRF2$^{\Delta B}$ that were dual-labeled for FLAG-tagged mutant protein using antibody M2 (green in FIGS. 13E and FIG. 13G) and either endogenous TRF2 (endTRF2, red in FIG. 13F) or endogenous TRF1 (endTRF1, red in FIG. 13H).

Figure 13I:
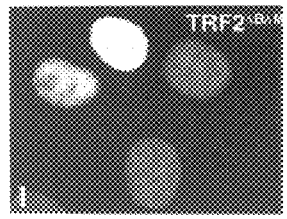
Figure 13J:
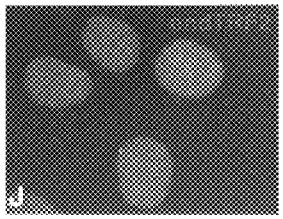
Figure 13K:
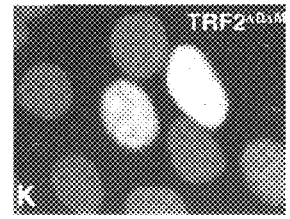
Figure 13L:
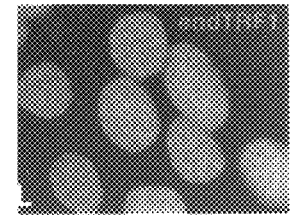

FIGS. 13I–13L show HeLa cells transiently transfected with TRF2$^{\Delta B \Delta M}$ that were dual-labeled for FLAG-tagged mutant protein using antibody M2 (green in FIGS. 13I and 13K) and either endogenous TRF2 (red in FIG. 13J) or endogenous TRF1 (red in FIG. 13L). DAPI staining of nuclear DNA in C-L is shown in blue.

Figure 14C:
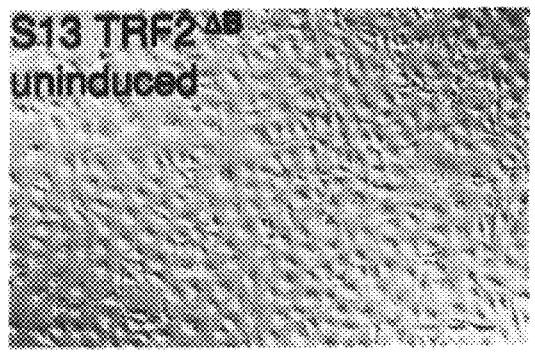
Figure 14D:
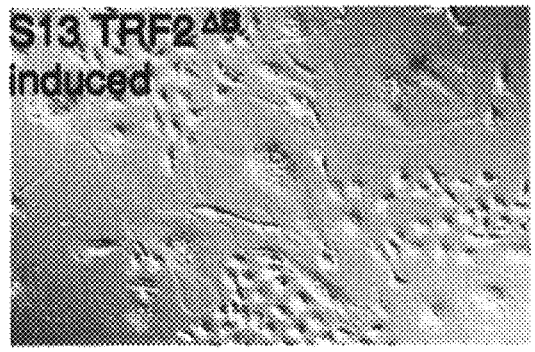
Figure 14E:
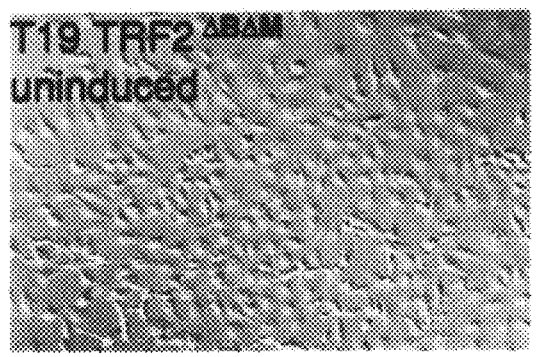
Figure 14F:
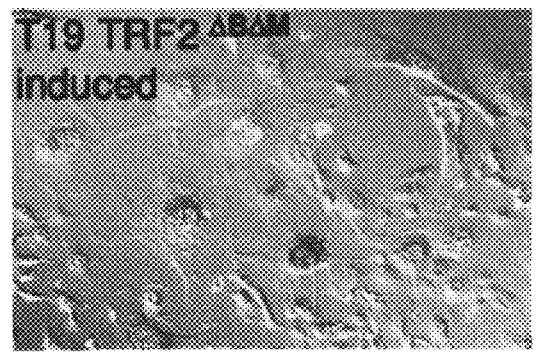
Figure 14G:
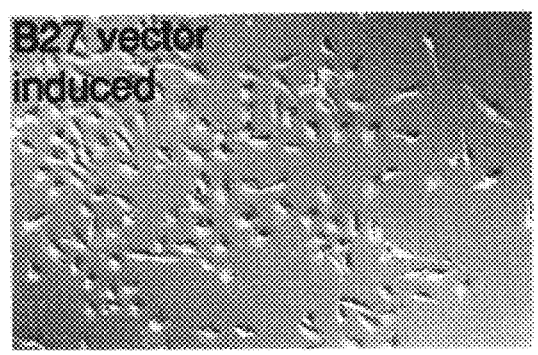
Figure 14H:
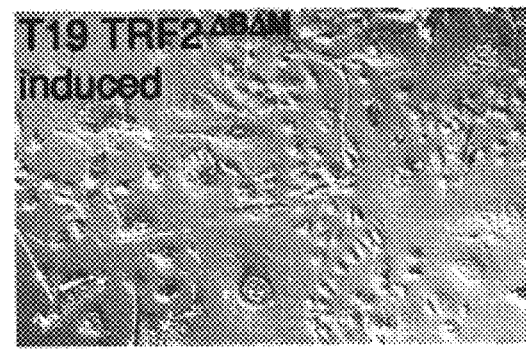

FIGS. 14A–14H. Growth arrest and induction of a senescent phenotype in response to TRF2 mutants. FIGS. 14A and 14B contain graphs showing the effect of induction of full length TRF2 (clone P12), TRF2$^{\Delta B}$(clone S13), and TRF2$^{\Delta B \Delta M}$ (clone T4) on the growth of HTC75 cells. B27 is a clonal HTC75 cell line containing the vector.

FIGS. 14C–14H show the morphological changes of the indicated HTC75 clones expressing the indicated TRF2 alleles grown for 9 days in the presence or absence (uninduced and induced, respectively) of doxycyclin. Cells were stained for β-galactosidase activity at pH 6.0 and photographed using DIC optics.

FIGS. 15A–15G depicts the induction of anaphase bridges and metaphase fusions by $TRF2^{\Delta B\Delta M}$. FIGS. 15A–C shows three anaphase cells displaying $TRF2^{\Delta B\Delta M}$-induced anaphase bridges and a lagging chromosome (cell on left). DNA was stained with DAPI.

FIG. 15D shows the induction of anaphase bridged and lagging chromosomes (together referred to as "events" on the y-axis) in T4 cells expressing the $TRF2^{\Delta B\Delta M}$ and lack of induced fusions in S13 cells expressing $TRF2^{\Delta B}$. For each time point one hundred anaphase cells were scored for anaphase bridges and lagging chromosomes.

FIGS. 15E–15G shows telomere fusions in metaphase chromosomes from T4 cells induced to express $TRF2^{\Delta B\Delta M}$ (FIG. 15E) Metaphase chromosomes showing end-to-end fusions stained with DAPI. Several fusion events (F) and a ring chromosome (R) are indicated. FIG. 16F Metaphase chromosomes G-banded with Trypsin showing multiple end-to-end fusions. FIG. 16G Detection of telomeric TTAGGG repeats at the sites of telomere fusion (arrowheads). TTAGGG repeats were detected using a fluorescently labelled PNA [CCCTAA]$_3$ probe (green). DNA was stained with DAPI.

Figure 16D:
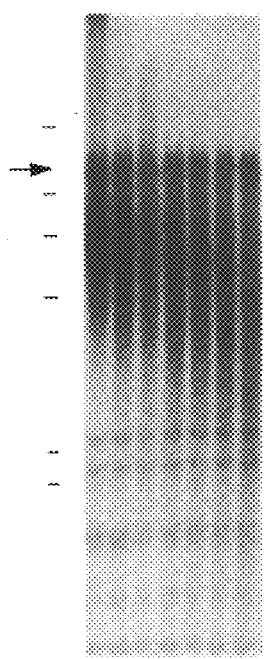
Figure 16E:
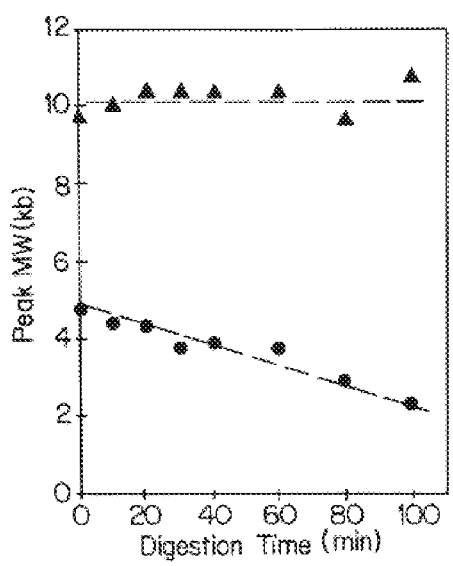
Figure 16F:
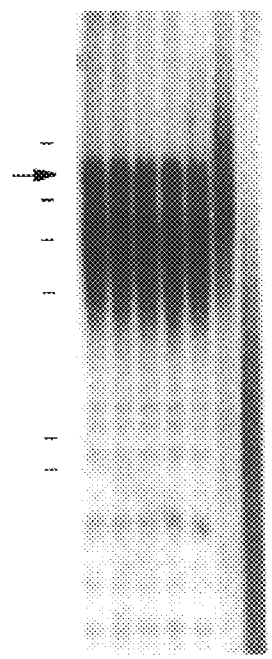

FIGS. 16A–16F. Detection of telomere fusions in naked DNA. FIG. 16A shows the telomere structure in clonal HTC75 lines expressing wildtype TRF2 (P clones) and in a vector control cell line (clone B27) grown in the presence and absence of doxycyclin (− and + induction respectively) for eight population doublings.

FIG. 16B shows the telomere structure in clonal lines expressing the indicated deletion of alleles of TRF2 grown with and without doxycyclin for 9 days (− and + induction respectively).

FIG. 16C depicts the time course of changes in telomere structure in T4 cells induced to express $TRF2^{\Delta B\Delta M}$ and in S24 cells induced to express $TRF2^{\Delta B}$.

FIG. 16D shows the Bal31 exonuclease digestion of DNA from T4 cells induced to express $TRF2^{\Delta B\Delta M}$ for 9 days.

FIG. 16E shows the quantitation of Bal131 exonuclease experiment similar to that shown in FIG. 16D performed with DNA from T19 cells induced to express $TRF2^{\Delta B\Delta M}$ for 9 days.

FIG. 16F shows the heat stability of the telomeric fusions. DNA derived from the same cells used in FIG. 16D was treated for 10 minutes at the indicated temperatures and immediately loaded on an agarose gel.

FIGS. 16A–16F shows all genomic DNA samples were digested with Hinfl an dRsal and analysed by blotting using a TTAGGG repeat scientific probe (see Experimental Procedures in Example 3). The position of λHindIII DNA marker fragments (23, 9.4, 6.6, 4.4, 2.3, and 2.0 kb) is indicated next to each blot.

Figure 17A:
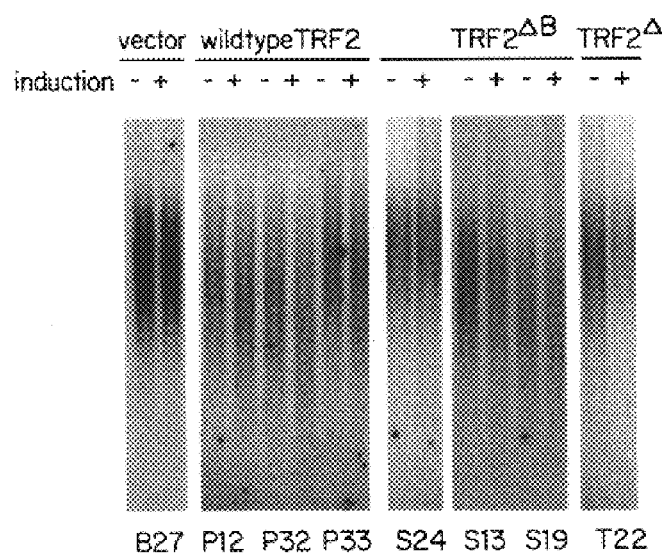

FIGS. 17A–17D. Expression of $TRF2^{\Delta B\Delta M}$ causes loss of G-strand overhang signals in the presence of telomerase activity. FIG. 17A shows the G-strand overhang assays performed on DNA derived from the indicated cell lines (grown in the presence or absence of doxycyclin for 9 days as indicated) expressing the indicated TRF2 polypeptides.

Figure 17B:
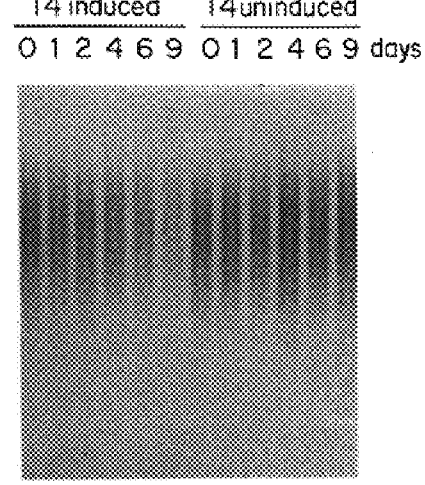

FIG. 17B depicts the time course of the loss of G-tails in the T4 clone expressing $TRF2^{\Delta B\Delta M}$.

Figure 17C:
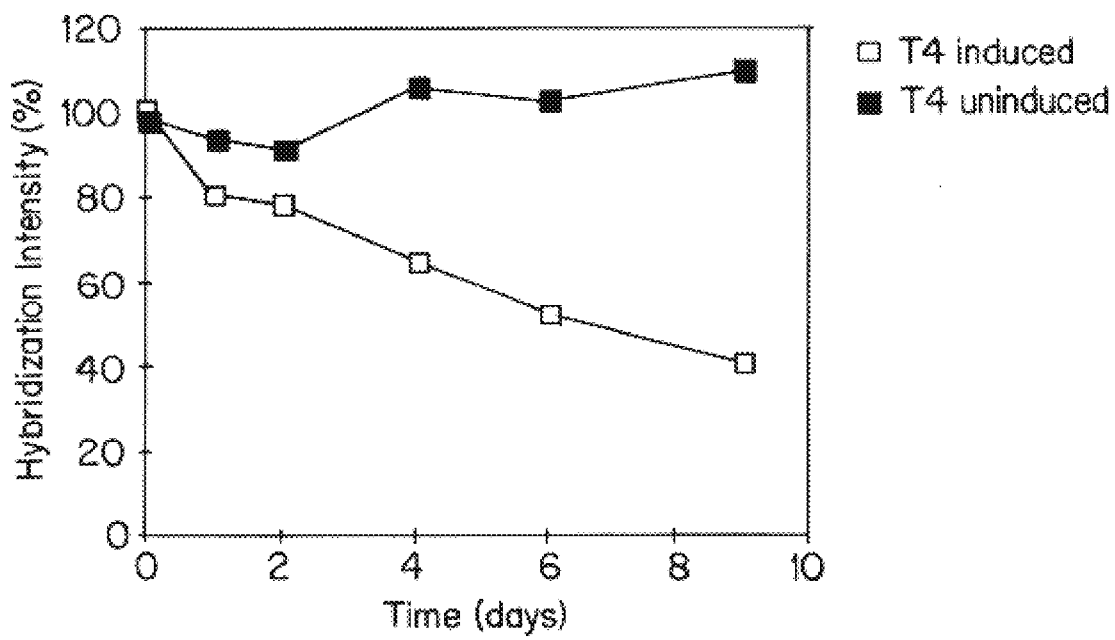

FIG. 17C shows the quantitation of the loss of G-strand overhangs upon induction of $TRF2^{\Delta B\Delta M}$ in two independents experiments performed with the T4 clone. The data were derived from two experiments similar to those shown in FIG. 17B and the average value was plotted.

Figure 17D:
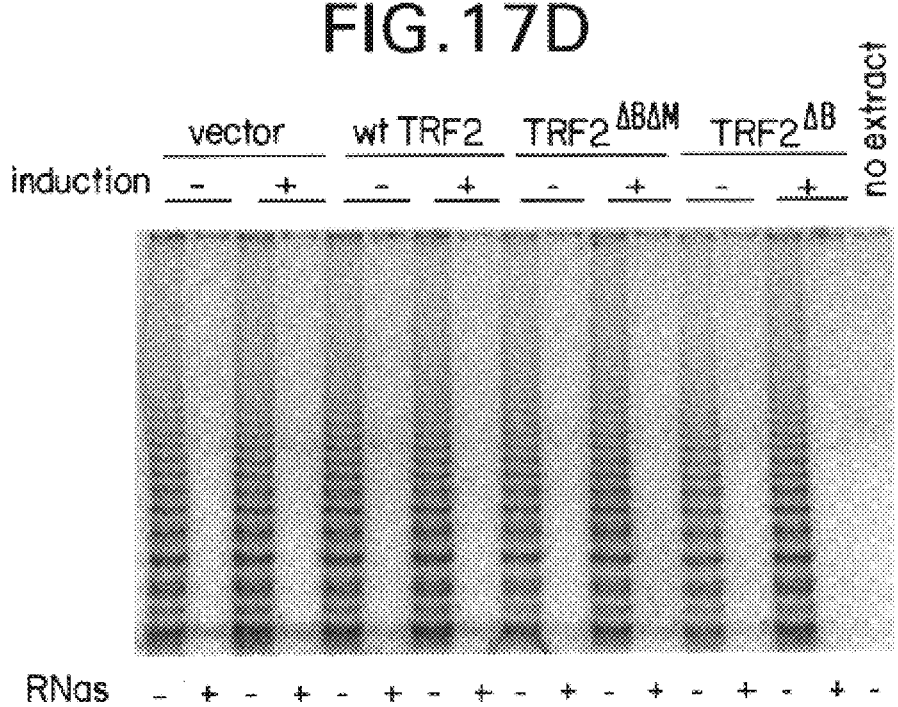

FIG. 17D shows the similar telomerase activity in four HTC75 clonal lines expressing the indicated TRF2 polypeptides grown for 9 days in the presence or absence of doxycyclin (− and + induction respectively). For each extract, identical amounts of protein (0.5 μg) were tested using the TRAP assay.

Figure 18:
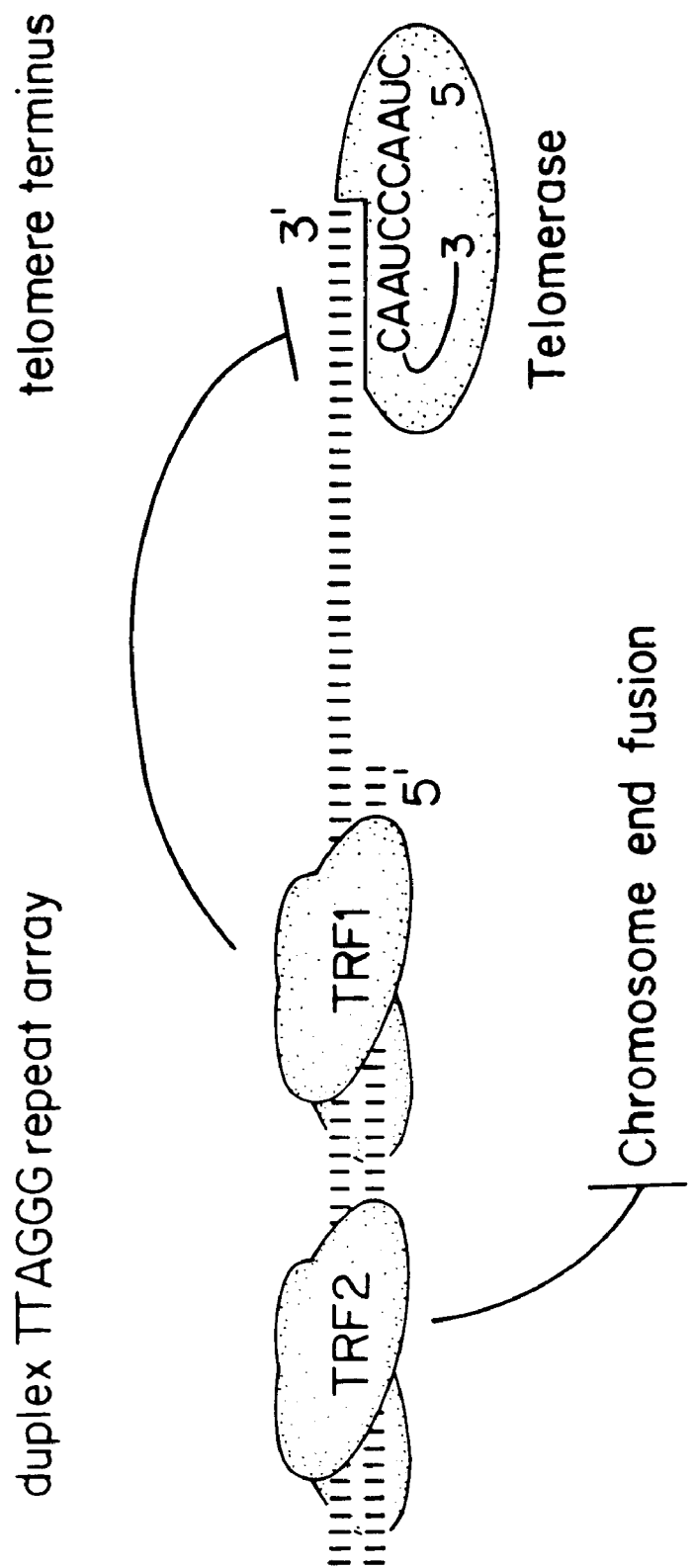

FIG. 18 illustrates the role of human telomeric proteins in telomere protection and telomere length regulation. TRF1 is depicted as a negative regulator of telomere maintenance, proposed to act by inhibiting telomerase at individual chromosome ends [van Steensel and de Lange, *Nature*, 385:740–743 (1997); Example 1] TRF2 is involved in the protection of chromosome ends by inhibiting end-to-end fusions. Thus, in the process of adding TTAGGG repeats, telomerase synthesizes binding sites for two proteins onto chromosome ends, one of which ensures telomere integrity and the other regulates the length of the telomeres.

DETAILED DESCRIPTION OF THE INVENTION

It has only recently become apparent that telomere dynamics plays a major role in the life-cycle of a cell. The regulation of telomere length has been implicated in the process of aging, as well as in cancer, and other human diseases. For example, the mutation in ataxia telangiectasia has recently be shown to confer a predisposition to accelerated telomere shortening in peripheral blood lymphocytes [Metcalfe et al., *Nature Genetics*, 13:350–353 (1996)].

Telomeres undergo progressive shortening during the development of human somatic tissue. Such telomere shortening eventually limits cell proliferation and leads to aging. Consistently, the number of cell divisions that primary human fibroblasts go through in culture is dependent on their initial telomere length. This correlation corresponds to a molecular clock that limits the potential of primary cells to replicate, and indicates that immortalization of human somatic cells involves a mechanism that must halt normal telomere shortening. This implies that successfully inducing the elongation of telomeres, either in vitro or in vivo, will counteract this aspect of the aging process, and could extend the life-span of human cells and tissues.

Indeed, cancer cells appear to have the ability to maintain their telomeres at specific lengths. Not surprisingly, many cancer cells contain the enzyme telomerase, which acts to lengthen telomeres and thereby counteract the shortening of the telomere that would otherwise occur during normal cellular division. Major efforts in the pharmaceutical industry are currently focused on telomerase as a target in cancer chemotherapy. The rationale of this approach is that inhibition of telomerase should lead to telomere shortening in the tumors and this process is eventually expected to halt proliferation of the cancer cells. In addition, telomeres of cancer cells are generally significantly shorter than those of the corresponding normal cells. This decrease in telomere length may be a factor in the instability of the genome of cancer cells.

The telomeric repeat binding factor1, TRF1, plays a role in the regulation of telomere maintenance by acting as a negative regulator of telomere elongation. TRFs are dimeric proteins that bind to a specific telomeric repeat sequence found at the ends of telomeres. In vertebrates, the telomeric repeat sequence is TTAGGG. TRFs have at least three distinct structural domains, two of which have known functions: a DNA binding domain encompassing the region of the protein that binds to the specific telomeric repeat sequence, and a dimerization domain encompassing the region of the monomer that binds to its germinate partner to form a dimer. The remaining structural feature is a polar N-terminal region of unknown function that can be either acidic, e.g., in TRFs of the TRF1 type, or basic, e.g., in TRFs of the TRF2 type.

In humans, the telomere maintenance is controlled by a negative feedback mechanism that stabilizes telomeres in telomerase-expressing cells. TRF1 regulates telomere length, at least in part, by binding to the ends of telomeres and inhibiting telomerase-catalyzed telomere elongation. Thus long term overexpression of TRF1s in telomerase-positive tumor cell lines results in a gradual and progressive telomere shortening, whereas the expression of a dominant-negative allele encoding an A-TRF inhibits binding of endogenous TRF1 to telomeres, and thereby permits telomere elongation.

Inhibition of TRF1 has been shown to lead to telomere elongation of cells expressing telomerase in vitro. Based on this data it follows that in vivo inhibition of TRF1 will result in telomere elongation in cells that express telomerase. Telomerase is expressed in self-renewing tissues such as bone marrow cells, peripheral blood T and B cells, and in basal keratinocytes. In these cells, and in other normal human cells that express telomerase, inhibition of TRF1 activity should lead to telomere elongation and concomitant extension of life-span.

Aside from the myriad of therapeutic applications for cells containing an A-TRF1 of the present invention, exemplified herein, cells having an extended life-span due, at least in part to the presence of the A-TR1;, can also have important ex vivo applications such as in the production of bioengineered products.

TRF2 is a telomeric protein that is required to maintain the correct structure at telomere termini, and thereby protect against end-to-end fusions. TRF2, therefore, plays a role in the successful progression through the cell division cycle. As such, TRF2 is involved in the main functions ascribed to telomeres in somatic human cells and is therefore a player in the loss of telomere function and growth arrest that accompanies telomere shortening in normal and transformed human cells.

A striking consequence of the loss of TRF2 function which can be achieved by the expression of the A-TRF2, $TF2^{\Delta B \Delta M}$, is the formation of end-to-end fusions detectable in metaphase and anaphase chromosomes. The presence of telomeric sequences at the fusions is demonstrated below by in situ hybridization, and the fused telomeric fragments were found to be detectable in protein-free genomic DNA. Yet while the telomeric TTAGGG repeats persisted, the telomeres failed to protect the chromosome ends from fusion, indicating that the duplex stretch of TTAGGG repeats persisted, the telomeres failed to protect the chromosome ends from fusion, indicating that the duplex stretch of TTAGGG repeats itself is insufficient for telomere protection in human cells. Therefore the protective function of telomeres is at least partially conferred by a nucleoprotein complex containing TRF2.

As described below TRF2 also plays a crucial role in the maintenance of unpaired G-strand overhangs at telomere termini. Loss of TRF2 from telomeres caused by expression of a A-TRF2, i.e., the dominant negative $TRF2^{\Delta B \Delta M}$ allele resulted in a ~50% reduction in the single-stranded TTAGGG repeat signal. Inhibition of TRF2 appears to result in an actual loss of G-tail DNA sequences from human chromosome ends. Such G-tail loss could be the consequence of a failure to protect the overhangs from degradation or could result from a deficiency in creating new G-tails after DNA replication.

TRF2 is the first telomere associated protein implicated in the maintenance of the correct DNA configuration of the telomeric 3' overhang. It was previously shown that telomerase is not involved in the maintenance of G-tails in yeast and mammals [Dionne and Wellinger, Proc. Natl. Acad. Sci. USA, 93:13902–13907 (1996)] and none of the other telomeric proteins identified in eukaryotes are known to affect this aspect of telomere synthesis. Data provided herein indicated that changes in telomerase expression are unlikely to be involved in this process. Therefore, TRF2 appears to protect telomeres from fusion through the maintenance of their single-strand TTAGGG repeat overhangs. This view is consistent with the finding that G-strand overhangs are a universal feature of eukaryotic telomeres [reviewed in Wellinger and Sen, Eur. J. Cancer, 33:735–749 (1997)] and identification of G-strand binding proteins in several systems. Thus, one of the main objectives of the transactions at telomeres may be to create and maintain a protrusion of single-stranded telomeric repeats that can bind specific proteins. This terminal complex could constitute the unique aspect of telomeres that allows cells to distinguish natural chromosome ends from broken DNA.

The present invention provides an altered vertebrate TRF monomer that binds to a TRF monomer to form a heterodimer (i.e., a dimer consisting of an A-TRF and a TRF). The present invention further provides these heterodimers. Relative to the corresponding TRF homodimer, the heterodimer has a reduced affinity for a specific telomeric repeat sequence. In preferred embodiments, the heterodimer does not bind the specific telomeric repeat sequence at all. The A-TRF can be missing portions of, or all of the DNA binding domain, or it can contain either a dysfunctional, or a non-functional DNA binding domain, including a substitute DNA binding domain that binds to an alternative DNA sequence.

Since the activity of TRF1 is inhibited by the A-TRF1s of the present invention, administration of an A-TRF1 can lead to the lengthening of the telomeres and thereby extend the life-span of the effected self-renewing tissues in which telomerase and TRF1 are expressed. This extension of life-span of the cells has cosmetic applications, such as in ointments or therapeutics to maintain youthful appearance, as well as being therapeutic for syndromes in which depletion of self-renewing activity leads to disease states. Some examples of the latter type include the immunodeficiency associated with ataxia telangiectasia, with HIV infection, and with Down's syndrome.

Similarly, the activity of TRF2 is inhibited by the A-TRF2s of the present invention, administration of an A-TRF2 can lead to telomere fusion and cell senescence. Selective administration can thereby lead to selective cell growth, i.e., retardation or full prevention of diseased cell proliferation.

In addition to in vivo strategies to elongate the telomeres in self-renewing tissues, for some cells it should also be possible to use in vitro therapy to change telomere length and improve the life-span of the tissue. In one such example, hematopoietic precursor cells are isolated from patients and grown for a limited time in vitro. During in vitro growth of such cells, an A-TRF1 of the present invention is administered to elongate the telomeres of the cells. Once the desired elongation is obtained, the cells are reintroduced into the patient.

In still another embodiment, an A-TRF of the invention can be provided, whether directly or by genetic engineering, to primary cells in tissue culture. Where such cells lack telomerase activity, telomerase can be introduced as well. In this way, the invention permits longer propagation or immortalization of cells in tissue culture, without requiring transformation of the cells or the need to create a hybridoma. Such cells in culture could include transfected cells for: expression of heterologous proteins by fermentation; skin or other organ cells for transplantation; non-hybridoma plasma β cells for production of useful monoclonal antibodies; tumor-specific cytotoxic T cells or tumor infiltrating cells for cancer therapy; and test cells for in vitro toxicity, efficacy, or other bioassays of drugs that more closely match cells in vivo. Thus, an advantage of the invention is that it permits propagation of cells in tissue culture without transforming the cells, thus making them useful for transplantation in vivo.

Indeed TRF1 is shown herein to be a negative regulator of telomere maintenance in cells expressing telomerase. The action of TRF1 occurs in cis, governing telomere elongation by telomerase at individual telomeres. The results described herein indicate that if large amounts of TRF1 protein is present on a telomere, that telomere terminus cannot be elongated by telomerase. As a consequence, the telomere will shorten. The truncated form of TRF1 inhibits this function of TRF1. Therefore, introduction of the truncated TRF1 allele (A-TRF1) results in telomere elongation. One utility of the present invention is therefore in the manipulation of telomere length in human cells for research purposes and/or for clinical applications.

Telomere elongation can be induced by introducing an A-TRF1 gene through standard gene transfer techniques (transfection, lipofection, retroviral transfer, adenovirus transfer, etc.) into human cells that express telomerase. The target cells for A-TRF1 delivery could be all and any human cell expressing telomerase. Included are: human tumor cells, immortalized human cell lines, primary human cells that naturally express telomerase (including self-renewing cells such as T-cells, β-cells, colonic crypt cells, endometricol cells, hair follicle cells, basal skin keratinocytes), and human cells that express telomerase after in vitro activation of telomerase.

Cells in which telomere length can be manipulated are an important tool for basic analysis of telomere structure, function, and dynamics and for the analysis of telomerase function and regulation. In addition, the manipulation of telomere length provides insight in the relationship between telomere dynamics and cellular life-span.

Telomere lengthening further has the potential application of changing the life-span of human cells, since telomere shortening limits the proliferative capacity of human cells. Thus, elongation of telomere expression of A-TRF1 will extend the life-span of human cells. Extension of life-span is relevant for the treatment of aging diseases and creation of cell populations used in gene-therapy. For instance, patient-derived bone marrow cells may be expanded in the laboratory and subjected to A-TRF1 mediated telomere elongation. Cells with elongated telomeres can be expected to be a more effective for transplants and gene-therapy because their in vivo life-span would be extended. Similar avenues exist for other human cells types, including cell types in which telomerase is not normally expressed, since telomerase may be temporarily activated in vitro.

Increased opportunity for in vitro life-span extension of normal human cells through A-TRF1 mediated telomere elongation also has applications in creating large populations of normal human cells in the laboratory. Large numbers of human cells can be important for generation of tissues (e.g. skin for burn victims) and generation of certain protein products (e.g. through gene therapy).

Similarly, expression of derivatives of TRF2 in human tumor cells leads to loss of the G-strand overhang at telomeres, telomere-telomere fusions, formation of anaphase bridges, chromosome breaks, arrest in cell growth, and expression of senescence markers. Such deletion forms of TRF2 (including A-TRF2s) could therefore be used to interfere with the growth of tumor cells. Genes encoding deletion forms of TRF2, such as A-TRF2s could be introduced into tumor cells in a specific way by gene transfer techniques and rapid cessation of tumor growth would be expected to result. Similarly, drugs may be found by screening for inhibitors of TRF2 function that would induce cell cycle arrest in human tumor cells. Such drugs are likely to have clinical utility in cancer treatment.

The induction of senescence by two deletion versions of TRF2 or A-TRF2s in general has applications in the study of this pathway. The inducible expression of these proteins in HTC75 cells as described herein leads to an inducible senescence phenotype. Such a system in which senescence is easily manipulated and induced has utility for the study of basic biology of senescence and in addition may have clinical application as an assay system for drugs that interfere with senescence and that therefore may extend the life-span of human cells.

More specifically, the direct correlation shown between telomere maintenance and cellular senescence, by [Bodner et al., Science, 279:349–352 (1993)] for example indicates that the compositions of matter and processes provided by the present invention can also play a direct role in preventing and/or treating (1) atrophy of the skin through loss of extracellular matrix homeostasis in dermal fibroblasts [Takeda et al., Arch. Dermatol. 130:87 (1994)]; (2) age-related macular degeneration [Bouton et al., J. Neurosci. 15:4992 (1995)]; (3) and atherosclerosis [Kumazaki et al., J. Med. Sci., 42:97 (1993)]. In addition, Bodner et al., [supra] has pointed out that cells having an extended life-span can also have important ex vivo applications in the production of bioengineered products such as recombinant proteins.

As used herein the terms "telomere repeat binding factor," "telomeric binding factor," "TRF," and any variants not specifically listed, may be used herein interchangeably, and as used throughout the present Application and Claims refer to proteinaceous material including single or multiple proteins. Accordingly, proteins displaying substantially equivalent activity are likewise contemplated. Also, the terms "telomere repeat binding factor," and "TRF" are intended to include within their scope proteins specifically recited herein as well as all substantially homologous analogs and allelic variations. TRFs have two structural domains in which the functions are known: a DNA binding domain encompassing the region of the protein that binds to the specific telomeric repeat sequence, and a dimerization domain encompassing the region of the monomer that binds to its germinate partner to form a dimer. Unless otherwise stated, the use of the term TRF indicates normal, wild type TRF as opposed to "A-TRF" which is defined below.

"TRF1" is one particular member of the TRF family. TRF1 has been purified from a human source. Human TRF1 has an amino acid sequence of SEQ ID NO:5 and has an apparent molecular weight of approximately 60 kDa, and thus in specific embodiments TRF is a protein having an apparent molecular weight of 60 kDa. In particular, the dimerization domain of human TRF1 comprises the amino acid sequence of SEQ ID NO:11 (AAs 66–264 of SEQ ID NO:5) encoded in a particular embodiment of the invention by nucleotide sequence SEQ ID NO:9; whereas the DNA binding domain comprises the amino acid sequence SEQ ID NO:12 (amino acid residues 378–439 of SEQ ID NO:5) encoded in a particular embodiment of the invention by nucleotide sequence SEQ ID NO:10. Human TRF1 is naturally encoded by a nucleic acid having the sequence of SEQ ID NO:1.

"TRF2" is another member of the TRF family. The human enzyme is naturally encoded by a nucleic acid having the sequence of SEQ ID NO:17 and the amino acid sequence of SEQ ID NO:18.

As used herein an "altered TRF" ("A-TRF") is a modified vertebrate TRF that binds to TRF to form a heterodimer. The resulting heterodimer has a measurably lower binding affinity for the TRF telomeric repeat sequence than does the corresponding TRF homodimer. Preferably there is at least a two-fold lower binding affinity; more preferably at least a ten-fold lower binding affinity. In the most preferred embodiment the heterodimer does not measurably bind to the telomeric repeat sequence at all. Thus the A-TRF hinders and/or prevents the binding of TRF to its telomere repeat sequence binding site. One particular embodiment of the present invention is "A-TRF1" which is an altered TRF1. In another embodiment, the A-TRF is an "A-TRF2" which is an altered TRF2.

As used herein a TRF "heterodimer" is dimer formed between a TRF monomer and a second monomer, including between a TRF monomer and an A-TRF monomer, in which the second monomer has a property not common to the corresponding TRF monomer. For example, the primary amino acid sequence of the second monomer can differ from that of the TRF monomer by more than a simple conservative substitution in an individual amino acid residue. Such non-identity in primary amino acid sequence can be due to a deletion, insertion, or truncation; or the other monomer can have a non-conservative substitution in an individual amino acid residue.

As used herein an A-TRF having a "dysfunctional DNA binding domain" has either a "malfunctioning DNA binding domain" e.g., the resulting heterodimer formed from the A-TRF and TRF has an affinity for the specific telomere repeat sequence that is measurably less than that of the corresponding TRF homodimer; or a "non-functioning DNA binding domain," e.g., the resulting heterodimer formed from the A-TRF and TRF does not measurably bind to the telomeric repeat sequence.

An A-TRF of the present invention can consist of the remainder of a TRF that has had its DNA binding domain deleted either in part or in toto through chemical, biochemical, or genetic manipulations. One such example is a truncated TRF. A truncated TRF1 having the amino acid sequence of SEQ ID NO:6 (AAs: 66–385) or SEQ ID NO:6 comprising conservative substitutions thereof is included in this class of A-TRF. In one particular embodiment of this type, the truncated TRF1 is encoded by a nucleic acid having the sequence of SEQ ID NO:2. A related example is an A-TRF in which only part of the binding domain of the corresponding TRF has been deleted. Similarly, a truncated TRF2 having the amino acid sequence of SEQ ID NO:14 or SEQ ID NO:14 comprising conservative substitutions thereof is also included in this class of A-TRF. In one particular embodiment of this type, the truncated TRF2 is encoded by a nucleic acid having the sequence of SEQ ID NO:13.

The present invention also includes A-TRFs which have a substitute DNA binding domain in place of the TRF binding domain. The DNA binding domain can be any such DNA binding domain including alternative Myb domains. One such example of this type is an A-TRF1 wherein the TRF1 Myb domain is replaced by the Myb domain of the mouse chromodomain protein CHD1. One embodiment of this type is A-TRF1$^{CHD1Myb}$ which has the amino acid sequence of SEQ ID NO:7, or SEQ ID NO:7 having conservative substitutions thereof. Because CHD1 binds AT-repeats, the Myb domain of this protein does not interact with the telomere repeat sequence TTAGGG. Since CHD1 is extremely abundant in mammalian cells, the expression of the A-TRF1$^{CHD1Myb}$ chimeric protein does not have an effect on CHD1 function. In one specific embodiment of this type, the A-TRF1$^{CHD1Myb}$ is encoded by a nucleic acid having the sequence of SEQ ID NO:3.

The present invention also includes altered TRFs that contain a deletion in the non-conserved hinge region of the corresponding TRF that either diminishes or completely abolishes the ability of the heterodimer, formed with a TRF, to bind to the specific telomere repeat sequence of the TRF. One example of this type is an A-TRF, A-TRF1$^{263-385}$, that has the amino acid sequence of SEQ ID NO:8 (AAs: 1–262, 386–439 of SEQ ID NO:5), or SEQ ID NO:8 having conservative substitutions thereof.

A-TRF1$^{D263-385}$ acts as a dominant negative allele, yet still contains the three conserved domains of a TRF including the two Myb domains required for DNA binding. In one specific embodiment of this type, the A-TRF1$^{D263-385}$ is encoded by a nucleic acid having the sequence of SEQ ID NO:3.

Alternatively the altered TRF can contain non-conservative amino acid alterations in its DNA binding domain and/or in the non-conserved hinge region which abolishes DNA binding activity.

All of the A-TRFs of the present invention can be modified, placed in a fusion of chimeric peptide or protein, or labeled e.g., to have an N-terminal FLAG-tag, or as described in detail below. In a particular embodiment an A-TRF can be modified to contain a marker protein such as green fluorescent protein as described in U.S. Pat. No. 5,625,048 filed Apr. 29, 1997 and WO 97/26333, published Jul. 24, 1997 each of which are hereby incorporated by reference herein in their entireties.

The present invention also relates to certain therapeutic methods based upon the telomere elongating consequences of administering an A-TRF1. Thus, the A-TRF1s may be administered to inhibit or potentiate TRF activity, in aging, or human diseases such as ataxia telangiectasia. Similarly, A-TRF2s may be used to retard and/or halt (selective) cell growth.

In addition, the TRF inhibitory effect of administering an A-TRF could be used in combination with telomerase therapy and/or with telomerase activating drugs. Inhibition of TRF together with enhancing telomerase activity may synergize the effects of these two telomere elongating effectors.

The present invention also includes methods of making, identifying, purifying, characterizing A-TRFs (including candidate A-TRFs) and analogs thereof; and methods of using A-TRFs and analogs thereof. A-TRFs can be produced by modifications including proteolytic cleavage of TRFs isolated from natural sources, through genetic engineering techniques, or chemical synthesis, e.g., by solid phase peptide synthesis; or produced de novo by genetic engineering methodology or solid phase peptide synthesis.

The present invention also includes methods of identifying A-TRFs. A candidate A-TRF, produced as described above, is a TRF that has been modified in such a manner that a skilled artisan would believe that the modified TRF would, at the minimum, retain affinity for its unmodified germinate binding partner. In the broadest sense of this aspect of the invention, a candidate A-TRF is contacted with a TRF. If a heterodimer does not form, the candidate A-TRF is rejected. If a heterodimer is formed, the binding of the heterodimer to a specific nucleic acid is determined. If the heterodimer has a relative affinity for the specific nucleic acid that is measurably less than that of the corresponding homodimer, the candidate A-TRF is selected and identified as an A-TRF. In one such embodiment the specific nucleic acid is the specific telomeric repeat sequence for the corresponding homodimer. In a preferred embodiment of this type, the heterodimer does not bind at all to the specific nucleic acid. The binding of the heterodimer and the homodimer to the selected nucleic acid can be performed by any standard DNA-protein binding assay including a gel-shift assay, a SouthWestern assay, through the use of nitrocellulose filter binding assays, or by a DNA bending assay; the specific nucleic acid can contain a label as described below.

In one specific embodiment a coupled in vitro transcription-in vitro translation system is employed to obtain both TRF alone, and a mixture created by the co-transcription/translation of TRF and a candidate A-TRF. The binding of the resulting lone TRF homodimer, and the TRF-candidate A-TRF heterodimer to a specific nucleic acid is determined individually by a DNA binding assay. If the heterodimer has a relative affinity for the specific nucleic acid that is less than that for the corresponding homodimer, the candidate A-TRF is selected. In preferred embodiments of this method, the heterodimer does not bind at all to the specific nucleic acid.

Transcription of the TRF and the candidate A-TRF does not require a particular RNA polymerase, and thus can be achieved with essentially any RNA polymerase such as T7, or T3, or SP6 RNA polymerase. Similarly, numerous translation systems may be employed such as the rabbit reticulocyte, or the wheat germ translation system. The binding of the heterodimer and the homodimer to the selected nucleic acid also can be performed by any standard DNA-protein binding assay including a gel-shift assay, a SouthWestern assay, a DNA bending assay or through the use of a nitrocellulose filter binding assay. The specific nucleic acid can also contain a label. In a particular embodiment of this type, the selected nucleic acid sequence is the telomeric repeat sequence to which the TRF naturally binds. In another particular embodiment of this type, the amount of the candidate A-TRF is co-transcribed/translated in increasing amounts, whereas the amount of the TRF co-transcribed/translated remains constant.

In one variation of this embodiment, in vitro translation products are also obtained for the candidate A-TRF alone. The binding of the A-TRF homodimer is determined by a DNA binding assay, allowing the relative affinity of the A-TRF homodimer to the TRF homodimer to be ascertained. If the candidate A-TRF homodimer binds the specific nucleotide sequence equivalently to the TRF homodimer, the candidate A-TRF can be rejected.

In another specific embodiment, a vertebrate cell in which endogenous TRF co-localizes with telomeric DNA is transfected with a nucleic acid comprising a candidate A-TRF. A candidate A-TRF is selected as an A-TRF for its ability to inhibit the co-localization of TRF with the telomeric DNA. In one embodiment of this type, the endogenous TRF co-localizes with telomeric DNA in interphase nuclei. A non-exhaustive list of appropriate vertebrate cells that may be so employed includes HeLa, HT1080, 293, Daudi, Raji, WI38, and IMR 90 cells. In preferred embodiments, the vertebrate cell is a HeLa cell.

In one specific embodiment of this method endogenous TRF1 and telomeric DNA are visualized to determine if they co-localize. Endogenous TRF1 in the nucleus of a HeLa cell is detected with a rabbit polyclonal antibody that cross-reacts with TRF1, and a FITC-conjugated donkey anti-rabbit antibody. Telomeric DNA is visualized in the same nucleus by fluorescence in situ hybridization of a digoxigenin-labelled $[CCCUAA]_{27}$ RNA followed by sheep anti-digoxigenin and TRITC conjugated donkey anti-sheep IgG. The HeLa cell is transfected with a candidate A-TRF1, which is expressed in excess of the endogenous concentration of TRF1. A candidate A-TRF1 is selected as an A-TRF if the endogenous TRF1 no longer co-localizes with the telomeric DNA. In a related embodiment the A-TRF1 can be synthesized with a FLAG tag and visualized with a mouse monoclonal antibody against the FLAG tag and a labeled donkey anti-mouse antibody. Although specific labels and animal sources for antibodies are presented in the above specific embodiment, a skilled artisan would know how to substitute analogous alternative labels and animal sources for those specifically mentioned.

The present invention also includes methods of using A-TRFs to identify drugs that interfere with the binding of TRF to its telomere repeat sequence. One such aspect includes drug screening assays to identify drugs that mimic and/or complement the effect of the A-TRFs. In one such embodiment, a drug library is screened by assaying the binding activity of TRF to a specific nucleic acid. The effect of a prospective drug on the affinity of the TRF-DNA binding is determined. If the drug decreases the binding affinity of the TRF to a DNA binding site, it becomes a candidate drug. Drugs can be screened for their particular ability to either disrupt the homodimers, hinder the dimerization process, or disrupt the TRF-DNA binding. In a variation of this embodiment, drugs may be screened that can enhance the binding of the TRF homodimer; or of the homodimer to its telomere repeat sequence.

The present invention also contains drug screening assays that may use any of a number of methods known in the art for determining the stability of protein-protein interactions in a dimer, including for fragments thereof, or determining the binding affinity of a TRF for a specific nucleic acid sequence. In particular, the A-TRF of the present invention may be used to distinguish between these two mechanisms, since the effect of a drug to disrupt direct TRF-DNA binding will have an additive effect with an A-TRF, whereas a drug that inhibits dimer formation will disrupt homodimer and heterodimer formation equally. Candidate drugs can be obtained from any number of drug libraries known in the art including those as described below.

In one embodiment the stability of preformed DNA-protein complex between a TRF homodimer and its corresponding telomere repeat sequence is examined in the presence and absence of a candidate drug as follows: a complex between the TRF homodimer and a labeled oligonucleotide comprising a telomere repeat sequence, e.g., $(TTAGGG)_6$ is allowed to form. Unlabeled oligonucleotides are added in vast molar excess after the reaction reaches equilibrium. At various times after the addition of unlabeled competitor DNA, aliquots are layered on a running native polyacrylamide gel to determine free and bound oligonucleotides. This procedure is performed in the presence and absence of the candidate drug. A candidate drug is selected on the basis of its ability to cause an increase in the amount of free labeled oligonucleotide.

In other binding assays, a telomere repeat sequence is either placed or coated onto a solid support. Methods for placing the telomere repeat sequence on the solid support are well known in the art and include such things as linking biotin to the oligonucleotide and linking avidin to the solid support. A corresponding TRF is allowed to equilibrate with the bound oligonucleotide and candidate drugs are tested to see if they disrupt the protein-DNA binding. Disruption leads to either a release of the TRF which may be expressed as a faster off time, and/or a greater concentration of released TRF. Enhancement leads to either a slower release of the TRF which may be expressed as a slower off time, and/or a lower concentration of released fragment. A candidate drug is selected on the basis of its ability to catalyze the release of the TRF.

The TRF may be labeled as described above. For example, in one embodiment a fluorescence-labeled TRF is used to measure the effect of a drug on the TRF-DNA binding. In another embodiment the natural ultraviolet absorbance of the TRF is used. In yet another embodiment, a BIAcore chip (Pharmacia) coated with the oligonucleotide is used and the change in surface conductivity can be measured.

An alternative assay takes advantage of the DNA bending properties of the TRF homodimer, which can be detected by a retardation in the migration of specific labeled DNA probes bound to a TRF homodimer. In such assays, labeled DNA probes consisting of variable TTAGGG repeat arrays, e.g. 6mers, or 12mers, can be incubated with a candidate A-TRF and a TRF, and the mobility of complexes formed between the TRF and the DNA probe is analyzed on native polyacrylamide gels, e.g., in a gel-shift assay. A candidate A-TRF that inhibits the TRF-associated retardation in the migration of such a labeled DNA probe is selected.

In one particular embodiment of this type, PCR primers that contain varied amounts of tandem TTAGGG repeats can be generated as the DNA probes. Such probes can be end-labelled with $^{32}P$-γ-ATP and polynucleotide kinase. The labelled probes are then isolated by preparative acrylamide gel-electrophoresis.

Genes Encoding Altered TRF Proteins

The present invention contemplates isolation of a gene encoding a vertebrate TRF, including a full length, or naturally occurring form of the TRF from any animal, particularly mammalian, and more particularly a human source, and modifying that TRF to produce the corresponding A-TRF of the present invention.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "heterologous nucleotide sequence" as used herein is a nucleotide sequence that is added to a nucleotide sequence of the present invention by recombinant methods to form a nucleic acid which is not naturally formed in nanture. Such nucleic acids can encode chimeric and/or fusion proteins. Thus the heterologous nucleotide sequence can encode peptides and/or proteins which contain regulatory and/or structural properties. In another such embodiment the heterlogous nucleotide can encode a protein or peptide that functions as a means of detecting the protein or peptide encoded by the nucleotide sequence of the present invention after the recombinant nucleic acid is expressed. In still another such embodiment the heterlogous nucleotide can function as a means of detecting a nucleotide sequence of the present invention. A heterlogous nucleotide sequence can comprise non-coding sequences including restriction sites, regulatory sites, promoters and the like.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). However, unless specifically stated otherwise, a designation of a nucleic acid includes both the non-transcribed strand referred to above, and its corresponding complementary strand. Such designations include SEQ ID NOs:. A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; preferably at least about 15 nucleotides; and more preferably the length is at least about 20 nucleotides; and most preferably 30 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into MRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell, 50:667 (1987)].

Accordingly, the term "sequence similarity" in all its grammatical forms refers to the degree of identity or correspondence between nucleic acid or amino acid sequences of proteins that do not share a common evolutionary origin [see Reeck et al., 1987, supra]. However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding TRF, whether genomic DNA or cDNA, can be isolated from any source, particularly from a human cDNA or genomic library. Methods for obtaining a TRF gene, as well as modifying it to produce an A-TRF are well known in the art, as described above [see, e.g., Sambrook et al., 1989, supra].

Accordingly, any animal cell potentially can serve as the nucleic acid source for the molecular cloning of a TRF gene. The DNA may be obtained by standard procedures known in the art from cloned DNA (e.g., a DNA "library"), by chemical synthesis, by cDNA cloning, or by the cloning of genomic DNA, or fragments thereof, purified from the desired cell [see, for example, Sambrook et al., 1989, supra; Glover, D. M. (ed.), 1985, DNA Cloning: A Practical Approach, MRL Press, Ltd., Oxford, U.K. Vol. I, II]. Clones derived from genomic DNA may contain regulatory and intron DNA regions in addition to coding regions; clones derived from cDNA will not contain intron sequences. Whatever the source, the gene or the corresponding modified gene encoding an A-TRF should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired TRF gene may be accomplished in a number of ways. For example, if an amount of a portion of a TRF gene or its specific RNA, or a fragment thereof, is available and can be purified and labeled, the generated DNA fragments may be screened by nucleic acid hybridization to the labeled probe [Benton and Davis, Science, 196:180 (1977); Grunstein and Hogness, Proc. Natl. Acad. Sci. U.S.A., 72:3961 (1975)]. For example, a set of oligonucleotides corresponding to the partial amino acid sequence information obtained for the TRF protein can be prepared and used as probes for DNA encoding a TRF. Preferably, a fragment is selected that is highly unique to a TRF. Those DNA fragments with substantial homology to the probe will hybridize. As noted above, the greater the degree of homology, the more stringent hybridization conditions can be used. In a specific embodiment, stringency hybridization conditions are used to identify a homologous TRF gene.

Further selection can be carried out on the basis of the properties of the gene, e.g., if the gene encodes a protein product having the isoelectric, electrophoretic, amino acid composition, or partial amino acid sequence of a TRF as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for a TRF or an A-TRF thereof.

A TRF gene can also be identified by mRNA selection, i.e., by nucleic acid hybridization followed by in vitro translation. In this procedure, nucleotide fragments are used to isolate complementary mRNAs by hybridization. Such DNA fragments may represent available, purified TRF DNA, or may be synthetic oligonucleotides designed from the partial amino acid sequence information. Immunoprecipitation analysis or functional assays (e.g., TRF or A-TRF activity) of the in vitro translation products of the products of the isolated mRNAs identifies the MRNA and, therefore, the complementary DNA fragments, that contain the desired sequences. In addition, specific mRNAs may be selected by adsorption of polysomes isolated from cells to immobilized antibodies specifically directed against TRF.

A radiolabeled TRF cDNA can be synthesized using the selected mRNA (from the adsorbed polysomes) as a template. The radiolabeled mRNA or cDNA may then be used as a probe to identify homologous TRF DNA fragments from among other genomic DNA fragments.

The present invention also relates to cloning vectors containing genes encoding the A-TRFs of the invention. The production and use of such derivatives and analogs related to the A-TRF are within the scope of the present invention. In a specific embodiment, the derivative or analog thereof, is capable of binding a full-length, wild-type TRF, but the resulting heterodimer is incapable of binding the telomere repeat sequence that the wild-type TRF binds.

The A-TRF can be made by altering nucleic acid sequences encoding an A-TRF by making substitutions, additions or deletions that provide for functionally equivalent molecules. Preferably, such derivatives are made that have enhanced or increased effect on telomere elongation relative to the truncated TRF of Example 1. For example, a preferred A-TRF may bind TRF more tightly than the truncated TRF of Example 1.

Due to the degeneracy of nucleotide coding sequences, other DNA sequences which encode substantially the same amino acid sequence as an altered TRF gene may be used in the practice of the present invention including those comprising conservative substitutions thereof. These include but are not limited to modified allelic genes, modified homologous genes from other species, and nucleotide sequences comprising all or portions of altered TRF genes which are altered by the substitution of different codons that encode the same amino acid residue within the sequence, thus producing a silent change. Likewise, the A-TRF derivatives of the invention include, but are not limited to, those containing, as a primary amino acid sequence, all or part of the amino acid sequence of an A-TRF protein including altered sequences in which functionally equivalent amino acid residues are substituted for residues within the sequence resulting in a conservative amino acid substitution. And thus, such substitutions are defined as a conservative substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to significantly affect apparent molecular weight as determined by polyacrylamide gel electrophoresis, or isoelectric point.

Particularly preferred conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. Pro may be introduced because of its particularly planar structure, which induces β-turns in the protein's structure.

The genes encoding A-TRF derivatives and analogs of the invention can be produced by various methods known in the art. The manipulations which result in their production can occur at the gene or protein level. For example, an A-TRF gene sequence can be produced from a native TRF clone by any of numerous strategies known in the art [Sambrook et al., 1989, supra]. The sequence can be cleaved at appropriate sites with restriction endonuclease(s), followed by further enzymatic modification if desired, isolated, and ligated in vitro. In the production of the gene encoding a derivative or analog of A-TRF, care should be taken to ensure that the modified gene remains within the same translational reading frame as the A-TRF gene, uninterrupted by translational stop signals, in the gene region where the desired activity is encoded.

Additionally, the A-TRF-encoding nucleic acid sequence can be produced by in vitro or in vivo mutations, to create and/or destroy translation, initiation, and/or termination sequences, or to create variations in coding regions and/or form new restriction endonuclease sites or destroy preexisting ones, to facilitate further in vitro modification. Preferably such mutations will further enhance the specific properties of the A-TRF gene product. Any technique for mutagenesis known in the art can be used, including but not limited to, in vitro site-directed mutagenesis [Hutchinson, C., et al., *J. Biol. Chem.*, 253:6551 (1978); Zoller and Smith, DNA, 3:479–488 (1984); Oliphant et al., *Gene*, 44:177 (1986); Hutchinson et al., *Proc. Natl. Acad. Sci. U.S.A.*, 83:710 (1986)], use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70). A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs with unnatural amino acids. Substitutions and deletions will preferably be performed in the DNA binding region of the protein, for example when the TRF is human TRF1, the DNA binding region has an amino acid sequence of SEQ ID NO:12.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of Altered TRF Polypeptides

The nucleotide sequence coding for an A-TRF, or a functionally equivalent derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding an A-TRF of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding the corresponding TRF and/or its flanking regions. Any person with skill in the art of molecular biology or protein chemistry, in view of the present disclosure, would readily know how to assay the protein expressed as described herein, to determine whether such a modified protein is indeed an A-TRF. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant A-TRF protein of the invention, or functionally equivalent derivative, or chimeric construct may be expressed chromosomally, after integration of the coding sequence by recombination. In this regard, any of a number of amplification systems may be used to achieve high levels of stable gene expression [See Sambrook et al., 1989, supra]. Chromosomal integration, e.g., by homologous recombination is desirable where permanent expression is required, such as to immortalize an antibody-producing plasma cell. In other embodiments, such as for in vitro propagation of cells for transplantation, transient transfection such as with a plasmid, is preferable. This way, the cell can be propagated indefinitely in vitro, but will terminally differentiate when reintroduced in vivo.

The cell containing the recombinant vector comprising the nucleic acid encoding an A-TRF is cultured in an appropriate cell culture medium under conditions that provide for expression of the A-TRF by the cell.

Any of the methods previously described for the insertion of DNA fragments into a cloning vector may be used to construct expression vectors containing a gene consisting of appropriate transcriptional/translational control signals and the protein coding sequences.

These methods may include in vitro recombinant DNA and synthetic techniques and in vivo recombination (genetic recombination).

Expression of an A-TRF may be controlled by any promoter/enhancer element known in the art, but these regulatory elements must be functional in the host selected for expression. Promoters which may be used to control A-TRF gene expression include, but are not limited to, the SV40 early promoter region [Benoist and Chambon, *Nature*, 290:304–310 (1981)], the promoter contained in the 3' long terminal repeat of Rous sarcoma virus [Yamamoto, et al., *Cell*, 22:787–797 (1980)], the herpes thymidine kinase promoter [Wagner et al., *Proc. Natl. Acad. Sci. U.S.A.*, 78:1441–1445 (1981)], the regulatory sequences of the metallothionein gene [Brinster et al., *Nature*, 296:39–42 (1982)]; prokaryotic expression vectors such as the β-lactamase promoter [Villa-Kamaroff, et al., *Proc. Natl. Acad. Sci. U.S.A.*, 75:3727–3731 (1978)], or the tac promoter [DeBoer, et al., *Proc. Natl. Acad. Sci. U.S.A.*, 80:21–25 (1983)]; see also "Useful proteins from recombinant bacteria" in *Scientific American*, 242:74–94 (1980); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells [Swift et al., *Cell*, 38:639–646 (1984); Ornitz et al., *Cold Spring Harbor Symp. Quant. Biol.*, 50:399–409 (1986); MacDonald, *Hepatology*, 7:425–515 (1987)]; insulin gene control region which is active in pancreatic beta cells [Hanahan, *Nature*, 315:115–122 (1985)], immunoglobulin gene control region which is active in lymphoid cells [Grosschedl et al., *Cell*, 38:647–658 (1984); Adames et al., *Nature*, 318:533–538 (1985); Alexander et al., *Mol. Cell. Biol.*, 7:1436–1444 (1987)], mouse mammary tumor virus control region which is active in testicular, breast, lymphoid and mast cells [Leder et al., *Cell*, 45:485–495 (1986)], albumin gene control region which is active in liver [Pinkert et al., *Genes and Devel.*, 1:268–276 (1987)], alpha-fetoprotein gene control region which is active in liver [Krumlauf et al., *Mol. Cell. Biol.*, 5:1639–1648 (1985); Hammer et al., *Science*, 235:53–58 (1987)], alpha 1-antitrypsin gene control region which is active in the liver [Kelsey et al., *Genes and Devel.*, 1:161–171 (1987)], beta-globin gene control region which is active in myeloid cells [Mogram et al., *Nature*, 315:338–340 (1985); Kollias et al., *Cell*, 46:89–94 (1986)], myelin basic protein gene control region which is active in oligodendrocyte cells in the brain [Readhead et al., *Cell*, 48:703–712 (1987)], myosin light chain-2 gene control region which is active in skeletal muscle [Sani, *Nature*, 314:283–286 (1985)], and gonadotropic releasing hormone gene control region which is active in the hypothalamus [,Mason et al. *Science*, 234:1372–1378 (1986)].

Expression vectors containing a nucleic acid encoding an A-TRF of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding A-TRF is inserted within the "selection marker" gene sequence of the vector, recombinants containing the A-TRF insert can be identified by the absence of the A-TRF gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX [Smith et al., *Gene*, 67:31-40 (1988)], pMB9 and their derivatives, plasmids such as RP4; phage DNAS, e.g., the numerous derivatives of phage γ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamHl cloning site; Summers), pVL1393 (BamHl, SmaI, XbaI, EcoRI, NotI, ,XmaIII, BglII, and PstI cloning site; Invitrogen), pVL1392 (BglII, PstI, NotI, XmaIII, EcoRI, XbaI, SmaI, and BamH cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamHl and KpnI cloning site, in which the BamHl recognition site begins with the initiation codon; Summers), pAc701and pAc702 (same as pAc700, with different reading frames), pAc360 (BamHl cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (199 1). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamHl, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamHl cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHl cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstM, NotI, SbaI, and ApaI cloning site, G418 selection; Invitrogen), pRc/RSV (HindIII, SpeI, BstXI, NotI, XbaI cloning site, G418 selection; Invitrogen). and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHl, ApaI, NheI, SacII, KpnI, and HindIII cloning site; TK- and β-gal selection), and pTKgptF1S (EcoRI, PstI, SalI, AccI, HindII, SbaI, BamHl, and Hpa cloning site, TK or XPRT selection).

Yeast expression systems can also be used according to the invention to express the A-TRF protein. For example, the non-fusion pYES2 vector (XbaI, SphI, ShoI, NotI, GstXI, EcoRI, BstXI, BamHl, SacI, KpnI, and HindIII cloning sit; Invitrogen) or the fusion pYESHisA, B, C (XbaI, SphI, ShoI, NotI, BstXI, EcoRI, BamHl, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an non-glycosylated core protein product. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the A-TRF activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu et al., *J. Biol. Chem.* 267:963–967 (1992); Wu and Wu, J Biol. Chem., 263:14621–14624 (1988); Hartmut et al., Canadian Patent Application No. 2,012,311, filed Mar. 15, 1990).

Gene Therapy and Transgenic Vectors

A gene encoding an A-TRF protein can be introduced either in vivo, ex vivo, or in vitro in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. For example, in the treatment of ataxia telangiectasia, T lymphocytes can be specifically targeted. Examples of particular vectors include, but are not limited to, a defective herpes virus 1 (HSV1) vector [Kaplitt et al., *Molec. Cell. Neurosci.*, 2:320–330 (1991)], an attenuated adenovirus vector, such as the vector described by Stratford-Perricaudet et al. [*J. Clin. Invest.*, 90:626–630 (1992)], and a defective adeno-associated virus vector [Samulski et al., *J Virol.*, 61:3096–3101 (1987); Samulski et al., *J. Virol.*, 63:3822–3828 (1989)]. Preferably, for in vitro administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ

(IFN-γ), or anti-CD4 antibody, can be administered to block humoral or cellular immune responses to the viral vectors [see, e.g., Wilson, *Nature Medicine*, (1995)]. In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., *Cell*, 33:153 (1983); Temin et al., U.S. Pat. No. 4,650,764; Temin et al., U.S. Pat. No. 4,980,289; Markowitz et al., *J. Virol.*, 62:1120 (1988); Temin et al., U.S. Pat. No. 5,124,263; International Patent Publication No. WO 95/07358, published Mar. 16, 1995, by Dougherty et al.; and Kuo et al., *Blood*, 82:845 (1993).

Targeted gene delivery is described in International Patent Publication WO 95/28494, published October 1995.

Alternatively, the vector can be introduced by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.*, 84:7413–7417 (1987); see Mackey, et al., *Proc. Natl. Acad. Sci. U.S.A.*, 85:8027–8031 (1988)]. The use of cationic lipids may promote encapsulation of negatively charged nucleic acids, and also promote fusion with negatively charged cell membranes [Felgner and Ringold, *Science*, 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., 1988, supra]. Targeted peptides, e.g., hormones or xneurotransmitters, and proteins such as antibodies, or non-peptide molecules could be coupled to liposomes chemically.

It is also possible to introduce the vector as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.*, 267:963–967 (1992); Wu and Wu, *J. Biol. Chem.*, 263:14621–14624 (1988); Hartmut et al., Canadian Patent Application No. 2,012,311, filed Mar. 15, 1990].

In a further embodiment, the present invention provides for co-expression of A-TRF and a telomerase and/or a telomerase enhancing gene under control of a specific DNA recognition sequence by providing a gene therapy expression vector comprising an A-TRF coding gene, and a telomerase gene and/or a telomerase enhancing gene under control of, inter alia, the telomerase regulatory sequence. In one embodiment, these elements are provided on separate vectors.

General Protein Purification Procedures

Initial steps for purifying the A-TRF of the present invention include salting in or salting out, such as in ammonium sulfate fractionations; solvent exclusion fractionations, e.g., an ethanol precipitation; detergent extractions to free membrane bound proteins using such detergents as TRITON X-100, TWEEN-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxypropyl] aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the using of a solid support such as phenylSepharose and a high salt buffer; affinity-binding, using, e.g., placing a specific telomeric repeat sequence on an activated support; immunobinding, using e.g., an antibody to an A-TRF bound to an activated support; as well as other solid phase supports including those that contain specific dyes or lectins etc. A further solid phase support technique that is often used at the end of the purification procedure relies on size exclusion, such as SEPHADEX and SEPHAROSE gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving protein purification employ a buffered solution. Unless otherwise specified, generally 25–100 mM concentrations of buffer salts are used. Low concentration buffers generally imply 5–25 mM concentrations. High concentration buffers generally imply concentrations of the buffering agent of between 0.1–2M concentrations. Typical buffers can be purchased from most biochemical catalogues and include the classical buffers such as Tris, pyrophosphate, monophosphate and diphosphate and the Good buffers [Good, N. E., et al., *Biochemistry*, 5:467 (1966); Good, N. E. and Izawa, S., *Meth. Enzimol.*, 24B:53 (1972); and Fergunson, W. J. and Good, N. E., *Anal. Biochem.*, 104:300 (1980] such as Mes, Hepes, Mops, tricine and Ches.

Materials to perform all of these techniques are available from a variety of sources such as Sigma Chemical Company in St. Louis, Mo.

Antibodies to the Altered TRFs

According to the present invention, the A-TRF as produced by a recombinant source, or through chemical synthesis, or through the modification of a TRF isolated from natural sources; and derivatives or analogs thereof, including fusion proteins, may be used as an immunogen to generate antibodies that specifically recognize the A-TRF and not TRF itself. Such antibodies include but are not limited to polyclonal, monoclonal, chimeric, single chain, Fab fragments, and a Fab expression library. The anti-A-TRF antibodies of the invention may be cross reactive, that is, they may recognize the A-TRF derived from a different natural TRF. Polyclonal antibodies have greater likelihood of cross reactivity. Alternatively, an antibody of the invention may be specific for a single form of an A-TRF, such as the truncated TRF having an amino acid sequence of SEQ ID NO:6.

Various procedures known in the art may be used for the production of polyclonal antibodies to the A-TRF or derivative or analog thereof. For the production of antibody, various host animals can be immunized by injection with the A-TRF, or a derivative (e.g., or fusion protein) thereof, including but not limited to rabbits, mice, rats, sheep, goats, etc. In one embodiment, the A-TRF can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward the A-TRF, or analog, or derivative thereof, any technique that provides for the production of antibody molecules by continuous cell lines in culture may be used. These include but are not limited to the hybridoma technique originally developed by Kohler and Milstein [*Nature*, 256:495–497 (1975)], as well as the trioma technique, the human B-cell hybridoma technique [Kozbor et al., *Immunology Today*, 4:72 (1983); Cote et al., *Proc. Natl. Acad. Sci. U.S.A.*, 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.*, 159:870 (1984); Neuberger et al., *Nature*, 312:604–608 (1984); Takeda et al., *Nature*, 314:452–454 (1985)] by splicing the genes from a mouse antibody molecule specific for an A-TRF together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce A-TRF-specific single chain antibodies. An additional embodiment of the invention utilizes the techniques described for the construction of Fab expression libraries [Huse et al., *Science*, 246:1275–1281 (1989)] to allow rapid and easy identification of monoclonal Fab fragments with the desired specificity for an A-TRF, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of the A-TRF and not TRF, one may assay generated hybridomas for a product which binds to the A-TRF fragment containing such epitope and choose those which do not cross-react with TRF. For selection of an antibody specific to the A-TRF from a particular source, one can select on the basis of positive binding with A-TRF expressed by or isolated from that specific source.

The foregoing antibodies can be used in methods known in the art relating to the localization and activity of the A-TRF, e.g., for Western blotting, imaging A-TRF in situ, measuring levels thereof in appropriate physiological samples, etc. using any of the detection techniques mentioned herein or known in the art.

In a specific embodiment, antibodies that agonize or antagonize the activity of A-TRF can be generated. Such antibodies can be tested using the assays described infra for identifying ligands.

Labels

The A-TRFs of the present invention, as well as nucleic acids that comprise the specific nucleotide sequences that TRFs bind, can all be labeled. Suitable labelsy include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker. In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. Such labels may also be appropriate for the nucleic acid probes used in binding studies with TRF. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419439 (1980) and in U.S. Pat. No. 4,857,453.

Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with 32p, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as [$^{35}$S]-methionine or [$^{32}$P]-orthophosphate. In addition to metabolic (or biosynthetic) labeling with [$^{35}$S]-methionine, the invention further contemplates labeling with [$^{14}$C]-amino acids and [$^{3}$H]-amino acids (with the tritium substituted at non-labile positions).

Drug Screening

In addition to rational design of agonists and antagonists based on the structure of the TRF dimerization domain for example, the present invention further contemplates an alternative method for identifying specific antagonists or agonists using various screening assays known in the art.

Accordingly any screening technique known in the art can be used to screen for agonists or antagonists of the TRF dimerization domain. The present invention contemplates screens for small molecule ligands or ligand analogs and mimics, as well as screens for natural ligands that bind to and agonize or antagonize TRF dimerization in vivo. For example, natural products libraries can be screened using assays of the invention for molecules that agonize or antagonize TRF dimerization activity.

Knowledge of the primary sequence of the TRF dimerization domain, and the similarity of that sequence with domains contained in other proteins, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, 1990, *Science* 249:386–390 (1990); Cwirla, et al., *Proc. Natl. Acad. Sci.*, 87:6378–6382 (1990); Devlin et al., *Science*, 249:404–406 (1990)], very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274(1987)] and the method of Fodor et al. [*Science* 251:767–773 (1991)] are examples. Furka et al. [*14th International Congress of Biochemistry*, Volume 5, Abstract FR:013 (1988); Furka, *Int. J Peptide Protein Res.* 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for ligands to the TRF dimerization domain according to the present invention.

Alternatively, assays for binding of soluble ligand to cells that express recombinant forms of the TRF dimerization domain can be performed. The soluble ligands can be provided readily as recombinant or synthetic polypeptides.

The screening can be performed with recombinant cells that express a TRF, an A-TRF, or fragment thereof, or alternatively, using purified protein, e.g., produced recombinantly, as described above. For example, the ability of labeled, soluble or solubilized A-TRF to bind ligand can be used to screen libraries, as described in the foregoing references.

In one such example, a phage library can be employed. Phage libraries have been constructed which when infected into host *E. coli* produce random peptide sequences of approximately 10 to 15 amino acids [Parmley and Smith, *Gene*, 73:305–318 (1988), Scott and Smith, *Science*, 249:386–249 (1990)]. Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive fragment of a TRF containing the dimerization domain e.g., for human TRF1 it is a peptide having the amino acid sequence of SEQ ID NO:11. After a specified incubation period, the filters can be thoroughly washed and developed for autoradiography. Plaques containing the phage that bind to the radioactive dimerization domain can then be identified. These phages can be fuirther cloned and then retested for their ability to hinder the formation of TRF homodimers and/or the binding of TRF to its telomere repeat sequence. Once the phages have been purified, the binding sequence contained within the phage can be determined by standard DNA sequencing techniques. Once the DNA sequence is known, synthetic peptides can be generated which represents these sequences.

It an alternative embodiment, the radioactive TRF fragment can contain the DNA binding domain, i.e., in human TRF1 it is a peptide having the amino acid sequence of SEQ ID NO:12. Plaques containing the phage that bind to the radioactive dimerization domain can be identified, further cloned and retested for their ability to hinder the binding of TRF to its telomere repeat sequence. Again, once the phages have been purified, the binding sequence contained within the phage can be determined by standard DNA sequencing techniques. Once the DNA sequence is known, synthetic peptides can be generated which represents these sequences.

These peptides can be tested, for example, for their ability to: (1) interfere with TRF forming a homodimer; and/or (2) interfere with TRF binding to its telomere repeat sequence. If the peptide interferes in the latter case, but does not interfere in the former case, it may be concluded that the peptide interferes with the TRF homodimer binding to its telomere repeat sequence.

The effective peptide(s) can be synthesized in large quantities for use in in vivo models and eventually in humans to stimulate telomere elongation. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, *Vaccine*, 10:175–178 (1990)].

Administration

According to the invention, the component or components of a therapeutic composition, e.g., an A-TRF and a pharmaceutically acceptable carrier, of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In a preferred aspect, an A-TRF of the present invention can cross cellular or nuclear membranes, which would allow for intravenous or oral administration. Strategies are available for such crossing, including but not limited to, increasing the hydrophobic nature of a molecule; introducing the molecule as a conjugate to a carrier, such as a ligand to a specific receptor, targeted to a receptor; and the like.

The present invention also provides for conjugating targeting molecules to an A-TRF. "Targeting molecule" as used herein shall mean a molecule which, when administered in vivo, localizes to desired location(s). In various embodiments, the targeting molecule can be a peptide or protein, antibody, lectin, carbohydrate, or steroid. In one embodiment, the targeting molecule is a peptide ligand of a receptor on the target cell. In a specific embodiment, the targeting molecule is an antibody. Preferably, the targeting molecule is a monoclonal antibody. In one embodiment, to facilitate crosslinking the antibody can be reduced to two heavy and light chain heterodimers, or the F(ab')$_2$ fragment can be reduced, and crosslinked to the A-TRF via the reduced sulfhydryl.

Antibodies for use as targeting molecule are specific for cell surface antigen. In one embodiment, the antigen is a receptor. For example, an antibody specific for a receptor on T lymphocyte receptor, can be used in the treatment of ataxia telangiectasia. This invention further provides for the use of other targeting molecules, such as lectins, carbohydrates, proteins and steroids.

In another embodiment, the therapeutic compound can be delivered in a vesicle, in particular a liposome [see Langer, *Science*, 249:1527–1533 (1990); Treat et al., in *Liposomes in the Therapy of Infectious Disease and Cancer*, Lopez-Berestein and Fidler (eds.), Liss: New York, pp. 353–365 (1989); Lopez-Berestein, ibid., pp. 317–327; see generally ibid.]. To reduce its systemic side effects, this may be a preferred method for introducing an A-TRF.

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used [see Langer, supra; Sefton, *CRC Crit. Ref Biomed. Eng.*, 14:201 (1987); Buchwald et al., *Surgery*, 88:507 (1980); Saudek et al., *N. Engl. J. Med.*, 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.*, 23:61 (1983); see also Levy et al., *Science*, 228:190 (1985); During et al., *Ann. Neurol.*, 25:351 (1989); Howard et al., *J. Neurosurg.*, 71:105 (1989)]. In yet another embodiment, a controlled release system can be placed in proximity of the therapeutic target, i.e., the brain, thus requiring only a fraction of the systemic dose [see, e.g., Goodson, in *Medical Applications of Controlled Release*, supra, vol. 2, pp. 115–138 (1984)]. Preferably, a controlled release device is introduced into a subject in proximity of the site of inappropriate immune activation or a tumor. Other controlled release systems are discussed in the review by Langer [*Science*, 249:1527–1533 (1990)].

Pharmaceutical Compositions. In yet another aspect of the present invention, provided are pharmaceutical compositions of the above. Such pharmaceutical compositions may be for administration for injection, or for oral, pulmonary, nasal or other forms of administration. In general, comprehended by the invention are pharmaceutical compositions comprising effective amounts of a low molecular weight component or components, or derivative products, of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. [1990, Mack Publishing Co., Easton, Pa. 18042] pages 1435–1712 which are herein incorporated by reference. The compositions may be prepared in liquid form, or may be in dried powder, such as lyophilized form.

Oral Delivery. Contemplated for use herein are oral solid dosage forms, which are described generally in Remington's Pharmaceutical Sciences, 18th Ed.1990 (Nack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925, 673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include an A-TRF (or chemically modified forms thereof) and inert ingredients which allow for protection against the stomach environment, and release of the biologically active material in the intestine.

Also specifically contemplated are oral dosage forms of the above derivatized component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. An example of such a moiety is polyethylene glycol.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Binders also may be used to hold the therapeutic agent together to form a hard tablet and include materials from natural products such as acacia, tragacanth, starch and gelatin.

An anti-frictional agent may be included in the formulation of the therapeutic to prevent sticking during the formulation process. Lubricants may be used as a layer between the therapeutic and the die wall. Glidants that might improve the flow properties of the drug during formulation and to aid rearrangement during compression also might be added. The glidants may include starch, talc, pyrogenic silica and hydrated silicoaluminate. In addition, to aid dissolution of the therapeutic into the aqueous environment a surfactant might be added as a wetting agent. Additives which potentially enhance uptake of the protein (or derivative) are for instance the fatty acids oleic acid, linoleic acid and linolenic acid.

Nasal Delivery. Nasal delivery of an A-TRF or telomere lengthening drug (or derivative) is also contemplated. Nasal delivery allows the passage of the protein to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defmed volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Transdermal administration. Various and numerous methods are known in the art for transdermal administration of a drug, e.g., via a transdermal patch. Transdermal patches are described in for example, U.S. Pat. No. 5,407,713, issued Apr. 18, 1995 to Rolando et al.; U.S. Pat. No. 5,352,456, issued Oct. 4, 1004 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. 5,008,110, issued Apr. 16, 1991 to Benecke et al.; and U.S. Pat. No. 4,921,475, issued May 1, 1990 to Sibalis, the disclosure of each of which is incorporated herein by reference in its entirety.

It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989 to Aruga et al., the disclosure of each of which is incorporated herein by reference in its entirety.

Pulmonary Delivery. Also contemplated herein is pulmonary delivery of the pharmaceutical compositions of the present invention. A pharmaceutical composition of the present invention is delivered to the lungs of a mammal while inhaling and traverses across the lung epithelial lining to the blood stream. Other reports of this include Adjei et al. [*Pharmaceutical Research*, 7:565–569 (1990); Adjei et al., *International Journal of Pharmaceutics*, 63:135–144 (1990) (leuprolide acetate); Braquet et al., *Journal of Cardiovascular Pharmacology*, 13(suppl. 5): 143–146 (1989) (endothelin-1); Hubbard et al., *Annals of internal Medicine*, Vol. III, pp. 206–212 (1989) ($\alpha$1-antitrypsin); Smith et al.,*J.

*Clin. Invest.*, 84:1145–1146 (1989) (α-1-proteinase); Oswein et al., "Aerosolization of Proteins", *Proceedings of Symposium on Respiratory Drug Delivery* II, Keystone, Colo., March, (1990) (recombinant human growth hormone); Debs et al., *J. Immunol.*, 140:3482–3488 (1988) (interferon-γ and tumor necrosis factor alpha); Platz et al., U.S. Pat. No. 5,284,656 (granulocyte colony stimulating factor)]. A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

All such devices require the use of formulations suitable for the dispensing of pharmaceutical composition of the present invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified pharmaceutical composition of the present invention may also be prepared in different formulations depending on the type of chemical modification or the type of device employed.

Formulations suitable for use with a nebulizer, either jet or ultrasonic, will typically comprise pharmaceutical composition of the present invention (or derivative) dissolved in water at a concentration of about 0.1 to 25 mg of biologically active ingredients of a pharmaceutical composition of the present invention per mL of solution. The formulation may also include a buffer and a simple sugar (e.g., for stabilization and regulation of osmotic pressure of a pharmaceutical composition of the present invention). The nebulizer formulation may also contain a surfactant, to reduce or prevent surface induced aggregation of the pharmaceutical composition of the present invention caused by atomization of the solution in forming the aerosol.

The liquid aerosol formulations contain a pharmaceutical composition of the present invention and a dispersing agent in a physiologically acceptable diluent. The dry powder aerosol formulations of the present invention consist of a finely divided solid form of a pharmaceutical composition of the present invention and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of nasal or pulmonary administration of a drug are well known in the art, and manipulation of formulations, aerosolization means and construction of a delivery device require at most routine experimentation by one of ordinary skill in the art.

Often, the aerosolization of a liquid or a dry powder formulation for inhalation into the lung will require a propellent. The propellent may be any propellant generally used in the art.

Specific non-limiting examples of such useful propellants are a chlorofluorocarbon, a hydrofluorocarbon, a hydrochlorofluorocarbon, or a hydrocarbon, including trifluoromethane, dichlorodifluoromethane, dichlorotetrafluoroethanol, and 1,1,1,2-tetrafluoroethane, or combinations thereof.

Systems of aerosol delivery, such as the pressurized metered dose inhaler and the dry powder inhaler are disclosed in Newman, S. P., *Aerosols and the Lung*, Clarke, S. W. and Davia, D. editors, pp.197–22 and can be used in connection with the present invention.

In general, as described in detail infra, pharmaceutical composition of the present invention is introduced into the subject in the aerosol form in an amount between about 0.01 mg per kg body weight of the mammal up to about 1 mg per kg body weight of said mammal. In a specific embodiment, the dosage is administered as needed. One of ordinary skill in the art can readily determine a volume or weight of aerosol corresponding to this dosage based on the concentration of pharmaceutical composition of the present invention in an aerosol formulation of the invention.

Liquid Aerosol Formulations. The present invention provides aerosol formulations and dosage forms. In general such dosage forms contain a pharmaceutical composition of the present invention in a pharmaceutically acceptable diluent. Pharmaceutically acceptable diluents include but are not limited to sterile water, saline, buffered saline, dextrose solution, and the like.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure.

Aerosol Dry Powder Formulations. It is also contemplated that the present aerosol formulation can be prepared as a dry powder formulation comprising a finely divided powder form of pharmaceutical composition of the present invention and a dispersant.

Formulations for dispensing from a powder inhaler device will comprise a finely divided dry powder containing pharmaceutical composition of the present invention (or derivative) and may also include a bulking agent, such as lactose, sorbitol, sucrose, or mannitol in amounts which facilitate dispersal of the powder from the device, e.g., 50 to 90% by weight of the formulation. The pharmaceutical composition of the present invention (or derivative) should most advantageously be prepared in particulate form with an average particle size of less than 10 mm (or microns), most preferably 0.5 to 5 mm, for most effective delivery to the distal lung.

In a further aspect, recombinant cells that have been transformed with the altered TRF gene and that express high levels of the polypeptide can be transplanted in a subject in need of an A-TRF. Preferably autologous cells transformed with an A-TRF are transplanted to avoid rejection; alternatively, technology is available to shield non-autologous cells that produce soluble factors within a polymer matrix that prevents immune recognition and rejection.

Methods of Treatment, Methods of Preparing a Medicament. In yet another aspect of the present invention, methods of treatment and manufacture of a medicament are provided. Conditions alleviated or modulated by the administration of the present derivatives are those indicated above.

Dosages. For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing.

Administration with other compounds. For treatment of aging and/or a disease one may administer the A-TRFs (or derivatives) in conjunction with telomerase and/or a telomerase stimulating agent.

Thus, the A-TRF polypeptide can be delivered by intravenous, intraarterial, intraperitoneal, intramuscular, or subcutaneous routes of administration. Alternatively, the A-TRF polypeptide, properly formulated, can be administered by nasal or oral administration. A constant supply of the A-TRF can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

A subject in whom administration of the A-TRF is an effective therapeutic regiment for cancer or in the alternative to counteract the aging process is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLES

EXAMPLE 1

TELOMERES LENGTH CONTROL BY THE HUMAN TELOMERIC PROTEIN TRF1

INTRODUCTION:

Telomeres are terminal structural elements found at the end of chromosomes. They are made up of multiple repeat units of DNA and serve to protect natural double-stranded DNA ends from degradation, fusion, and recombination with chromosomal internal DNA. The repeat units are typically five to eight base pairs long and the number of repeat units vary between 300 to 5000 in humans.

Human telomeres are maintained by telomerase, an ribonucleoprotein reverse transcriptase that can elongate chromosome ends with arrays of TTAGGG repeats. The stability of telomeres in several telomerase-positive human cell lines indicates that telomere maintenance is regulated. TRF1, human telomeric repeat binding factor, is now demonstrated to be involved in this process. Long term overexpression of TRF1 in the telomerase-positive tumor cell line HT1080 resulted in a gradual and progressive telomere shortening. Conversely, a dominant-negative allele that inhibited binding of endogenous TRF1 to telomeres, induced telomere elongation. The dominant-negative allele encoded an A-TRF1, more specifically a truncated form of TRF1 missing the DNA binding domain, which hindered the binding of TRF1 to its DNA binding site, TTAGGG. The results identify TRF1 as a negative regulator of telomere elongation and show that human telomere maintenance is controlled by a negative feedback mechanism that stabilizes telomeres in telomerase-expressing cells. Since telomerase activity levels were not affected by TRF1, it may be concluded that TRF1 controls telomere length by inhibiting telomerase at the ends of individual telomeres.

METHODS

Inducible gene expression system. HT1080 cells were stably co-transfected with the tTA-expression vector pUHD15-1 and hygromycin resistance plasmid pBPGKHyg. About 50 hygromycin-resistant clones were expanded and tested for expression of transiently transfected luciferase reporter plasmid pUHC13-1 in the absence and presence of doxycycline (100 ng/ml). Clone HTC75 showed an approximately 100-fold increase in luciferase expression upon withdrawal of doxycycline. Next, HTC75 cells were stably co-transfected with neomycin resistance plasmid pSXneo and either TRF1, FLAG-TRF1 or A-TRF1$^{66-385}$ were cloned into the tTA-regulated expression vector pUHD10-3. For each construct about 25 G418-resistant clones were tested for inducible expression of the appropriate protein by immunofluorescence microscopy and western blotting using anti-FLAG antibody M2 (Eastman-Kodak), and gelshift analysis of whole-cell extracts using a telomeric repeat probe.

Long-term cell culture. All cells were grown in DMEM supplemented with 10% bovine calf serum (Irving Science). Clones indicated in the text were passaged 1:16 when approximately 80% confluent (typically every 3 days). All clones were grown in parallel with and without doxycycline (Sigma; 100 ng/ml). The presence of hygromycin (90 mg/ml) or G418 (150 mg/ml) in the growth media was alternated every two weeks.

Antibodies. Antibody Ab371C2 against the acidic domain of TRF1 was affinity-purified in two steps from a rabbit polyclonal serum against baculovirus-expressed TRF1 protein (bacTRF1). First, the antiserum was purified against bacTRF1 coupled to CNBr-activated agarose. Next, the resulting antibodies were purified against a bacterially expressed fusion protein consisting of Glutathione-S-transferase and amino acid residues 1–71 of TRF1 representing the acidic domain. Purified Ab 371C2 did not cross-react with any part of TRF1 outside the acidic domain, as confirmed by western blotting and immunofluorescence microscopy of various TRF1 deletion mutants. All fluorochrome-conjugated antibodies (Jackson ImmunoResearch Laboratories) were multilabeling grade.

Cell extracts. Cells grown to about 80% confluency in 10 cm petri dishes were harvested by scraping in phosphate-buffered saline. Cells were pelleted and incubated 30 minutes at 4 °C. in 250 μl buffer C [20 mM HEPES-KOH (pH 7.9), 1 mM Dithiothreitol, 0.5 mM phenylmethylsulfonyl fluoride, 25 % glycerol, 0.1 mM EDTA, 5.0 mM $MgCl_2$ and 0.42 M KCl] with 0.2% Nonidet β-40. After centrifugation (10 minutes at 14,000×g) the supernatant was dialyzed against buffer D [20 mM HEPES-KOH (pH 7.9), 0.5 mM Dithiothreitol, 0.5 mM phenylmethylsulfonyl fluoride, 20 % glycerol, 0.2 mM EDTA, 0.2 mM EGTA and 0.1 M KCl] and stored at −70 °C. until use for gelshift assays, western blotting, and TRAP assays. Protein content was determined by the Bradford assay (BioRad).

Genomic blotting and telomere length estimation. Genomic DNA was isolated from cells at indicated PDs, digested to completion with HinfI and RsaI and quantitated by fluorometry using Hoechst 33258. Genomic blots were made as described as follows. Genomic blotting of telomeric DNA was performed with 0.7% agarose gels which were run in the presence of ethidium bromide at 1–2 V/cm in TAE buffer (0.04 M Tris-Acetate pH 8.3/1 mM EDTA). The fractionated DNA was depurinated in situ by a 20 min incubation in 0.25 N HCl, then denatured and nicked with 0.5 M NaOH/1.5 M NaCl (2×20 min) and finally neutralized in 0.5 M Tris-HCl pH 7.5/3 M NaCl (2×20 min). The DNA was subsequently transferred to an Hybond-N membrane (Amersham)in 20×SSC (3 M NaCl/0.3 M Na-Citrate pH 7.0) for 3 hours and cross-linked by ultraviolet light exposure in a Stratalinker (Stratagene). After a 20 min pre-hybridization, the membranes were hybridized overnight at 65° C. with the TTAGGG repeat probe in 0.5 M sodium phosphate buffer pH 7.2 containing 1 mM EDTA, 7% SDS, and 1% BSA. The probe used is a 800 base pair DNA fragment from plasmid pSty11 composed primarily of TTAGGG repeats which was labelled with Klenow enzyme using a 5' $(CCCTAA)_2$3' primer and alpha-$^{32}$P-labelled dCTP. Post-hybridization washes were performed in 40 mM sodium phosphate buffer pH 7.2, 1 mM EDTA, 1% SDS at 65° C. Various exposures were made using a PhosphorImager.

The median telomeric restriction fragment length was determined by PhosphorImager analysis using ImageQuant software and was not corrected for the fact that long telomeres give a stronger hybridization signal than short telomeres.

RESULTS AND DISCUSSION

The role of TRF1 in telomere length regulation, was investigated by studying the effects of long-term overexpression of a wildtype and a dominant negative mutant TRF1 on the telomere length in a telomerase-positive human tumor cell line containing stable telomeres. The tetracycline-controlled gene expression system in the human fibrosarcoma cell line HT1080 (resulting in cell line HTC75) was established. This expression system was used for inducible expression of full length TRF1, a TRF1 allele containing an N-terminal FLAG epitope (FLAG-TRF1), and an A-TRF1, i.e., a TRF1 deletion mutant encompassing amino acids 66–385 (TRF1$^{66-385}$) having an amino acid sequence of SEQ ID NO:6 (FIG. 1A). Western analysis showed doxycycline negatively controlled expression of each of these TRF1 proteins in clonal HT1080tTA cell lines transfected with the constructs (FIG. 1B).

Induced overexpression of the full length TRF1 and the FLAG-TRF1 resulted in a 10–30 fold increase in the TTAGGG repeat binding activity as detected by quantitative gel-shift assays on extracts of the HT1080tTA lines. The expression level of the A-TRF1$^{66-385}$ protein was consistently low compared to the other TRF1 alleles. Expression of wildtype or mutant TRF1 proteins did not affect the viability or growth rate of the cells.

Figure 2B:
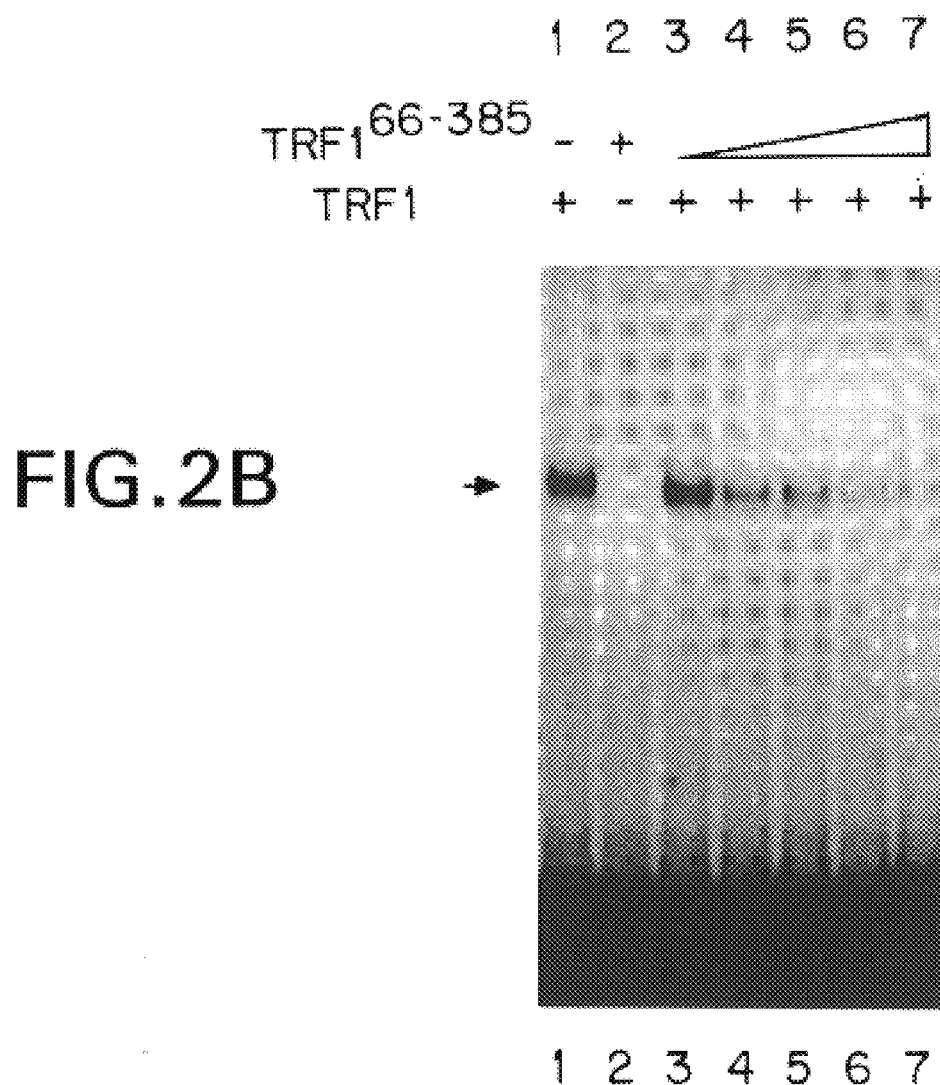

The deletion mutant, A-TRF1$^{66-385}$, acted as a dominant interfering mutant. TRF1 binds telomeric DNA as a homodimer, using a large dimerization domain to position two identical Myb-related DNA binding motifs on its telomeric recognition site (see FIG. 1A for the domain structure of TRF1). A-TRF1$^{66-385}$ contains the dimerization domain and putative nuclear localization sequences, but lacks the DNA-binding motif (FIG. 1A), but if it bound wildtype TRF1 it would form a heterodimer. The effect of A-TRF1$^{66-385}$ on the DNA binding of wildtype TRF1 in a gel-shift assay with in vitro translated proteins was investigated. In vitro synthesis of A-TRF1$^{66-385}$ resulted in a polypeptide that was slightly smaller than TRF1 (FIG. 2A, lanes 1 and 2) consistent with the Western analysis of transfected HT1080tTA cells (FIG. 1B, lane 8). Wildtype TRF1 formed a complex with telomeric DNA, whereas A-TRF1$^{66-385}$ showed no DNA-binding activity (FIG. 2B, lanes 1 and 2). Co-translation of TRF1 and A-TRF1$^{66-385}$ (FIG. 2A, lanes 3–7) under conditions previously shown to allow dimerization[10], demonstrated that A-TRF1$^{66-385}$ caused a dose-dependent inhibition of DNA-binding activity of TRF1 (FIG. 2B, lanes 3–7). Thus, while synthesis of TRF1 alone yielded the expected TTAGGG repeat binding activity, co-translation of TRF1 with the mutant A-TRF1$^{66-385}$ protein abolished the ability of TRF1 to bind to DNA, indicating that the A-TRF, A-TRF1$^{66-385}$, is a dominant negative mutant.

Figure 2C:
Figure 2D:
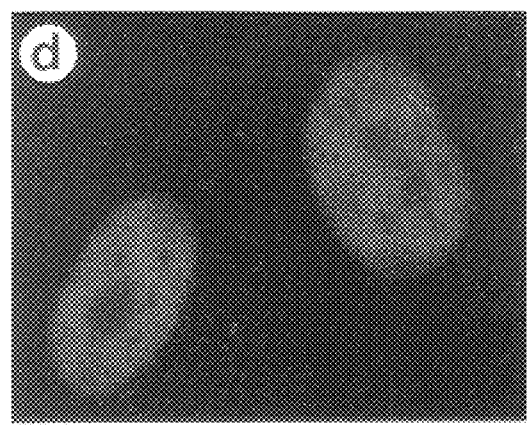
Figure 2E:
Figure 2F:
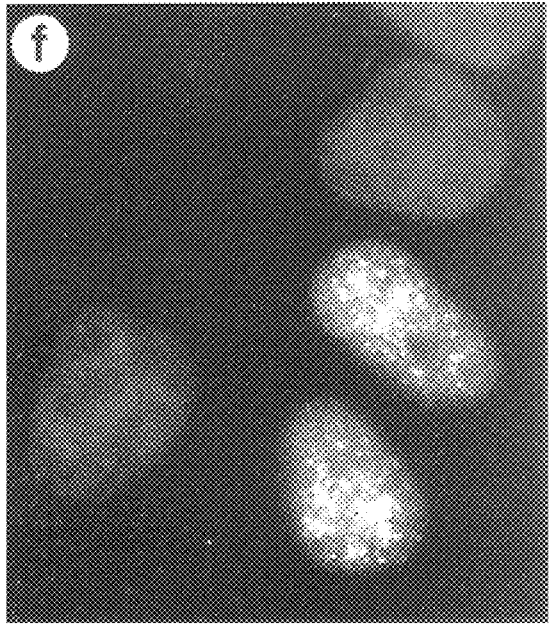
Figure 2G:
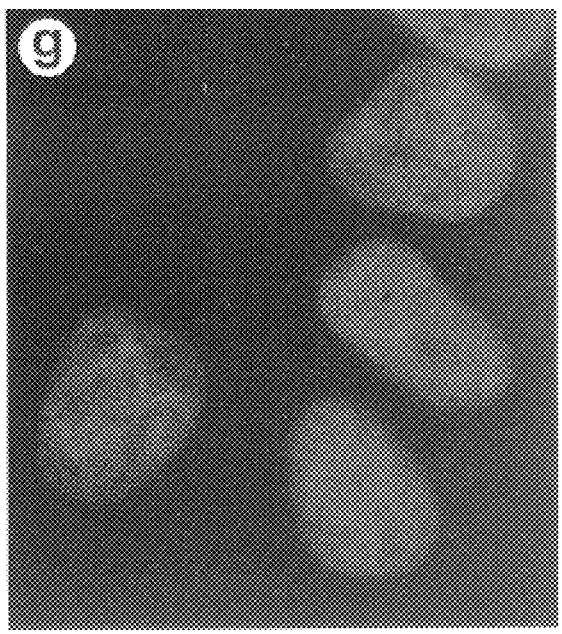

Evidence was obtained that this dominant negative effect on DNA binding also resulted in the loss of TRF1 accumulation at the telomeres in vivo. Immunofluorescent labeling using a rabbit polyclonal antibody against the acidic domain of TRF1 (Ab 371C2, see METHODS), combined with fluorescent in situ hybridization using a telomere-specific $[CCCUAA]_{27}$ RNA probe showed that endogenous TRF1 in HeLa cells was located in a speckled distribution that coincided with telomeric repeat DNA (FIGS. 2C–2E). This indicated that endogenous TRF1 was primarily located at telomeres in interphase nuclei. In contrast, immunolocalization of transfected A-TRF1$^{66-385}$ in HeLa cells using a mouse monoclonal anti-FLAG antibody revealed that this protein was homogeneously distributed throughout the nuclear volume (FIG. 2F). Thus, the deletion of the Myb homology region in A-TRF1$^{66-385}$ resulted in the TRF not accumulating at the telomeres. To test whether the mutant protein affected the localization of the endogenous TRF1 to telomeres dual labelling immunofluorescence with Ab 371C2 was carried out to detect endogenous wildtype TRF1; an anti-FLAG monoclonal antibody was used to detect A-TRF1$^{66-385}$. As can be readily seen, the distribution of endogenous TRF1 was drastically altered in cells that expressed A-TRF1$^{66-385}$ (FIGS. 2F and 2G). In the transfected cells, the endogenous TRF1 protein often did not show a punctate pattern, indicating that TRF1 was dislodged from the telomeres. Furthermore, there was a direct relationship between the expression level of A-TRF1$^{66-385}$ and the loss of endogenous TRF1 from the telomeres. The displaced TRF1 was present throughout the nuclear volume in these cells presumably, but it was too low in abundance to reveal a dispersed pattern in immuno-staining experiments. These results demonstrate that expression of A-TRF1$^{66-385}$ reduces the amount of TRF1 present around telomeres during interphase.

TABLE 1

TELOMERE LENGTH CONTROL BY TRF1

| HT1080 clone | TRF1 construct | Δ telomere length after 88 PD without doxycycline |
|---|---|---|
| B6 | vector | 0.0 kb |
| D4 | full length TRF1 | −1.0 kb |
| D16 | full length TRF1 | −0.6 kb |
| D20 | full length TRF1 | +0.7 kb |
| C14 | FLAG-TRF1 | −0.3 kb |
| C20 | FLAG-TRF1 | −0.6 kb |
| K4 | A-TRF1$^{66-385}$ | +0.5 kb |
| K10 | A-TRF1$^{66-385}$ | +2.4 kb |
| K15 | A-TRF1$^{66-385}$ | +2.8 kb |
| K16 | A-TRF1$^{66-385}$ | +2.9 kb |
| K17 | A-TRF1$^{66-385}$ | +1.0 kb |

Telomere length control in HT1080 cells was altered by changes in the level of TRF1. A control cell line transfected with the vector showed stable telomeres over 124 population doublings (PDs). There was no effect of doxycycline on telomere length (FIG. 3A and Table 1). In contrast, cells over-expressing TRF1 showed gradual and progressive telomeric decline when grown under inducing conditions, i.e., in the absence of doxycycline (FIG. 3B). The loss of telomeric sequences was evident from the shortening of the terminal restriction fragments and from a reduction in the TTAGGG repeat hybridization intensity. Telomeres were shortened in 4 out of 5 cell lines that overexpressed either full length or FLAG-tagged TRF1 (Table 1). In three clones (D4, D16, and C20) the decline was only observed in absence of doxycycline. Clone C14, a clone that expressed FLAG-tagged TRF1 at considerable levels independent of induction, showed a moderate loss of telomeric DNA both in the induced and non-induced state. These results implicated TRF1 in the regulation of telomere length. The variation in the rate of telomere shortening in the different cell lines varied between 3–11 bp per population doubling (Table 1).

In contrast, HT1080 cells that express the dominant negative A-TRF1$^{66-385}$ allele showed a gradual increase in telomere length. In the K10 clone shown in FIG. 3C, telomeres showed progressive elongation over about 80 PDs with a rate of approximately 35 bp/PD. Eventually the telomeres stabilized. At this stage in the culture, telomere length remained under control of the dominant negative allele of TRF1 since repression of the gene at PD 104 with doxycycline resulted in a gradual shortening of the telomeres. Induced telomere elongation was also observed in four additional independent HT1080tTA clones expressing the dominant negative TRF1 mutant (Table 1). In each case, telomere elongation was enhanced in the absence of doxycycline, indicating that the elongation is due to expression of the A-TR16&-385 protein. The altered dynamics appeared to affect all telomeres to approximately the same degree, leading to a gradual consorted elongation of the telomeric pattern. After extensive growth of the cell lines (88 PDs) the telomeres had elongated by 0.4 to 2.9 kb (Table 1). The terminal restriction fragments visualized by genomic blotting (FIG. 3) harbor approximately 1.5 kb of subtelomeric DNA. Based on this estimation the telomere alterations in the A-TRF1$^{66-385}$ expressing cell lines appears to represent between a 20% to 105% increase in the length of the telomeric repeat array. A commensurate increase in the TTAGGG repeat signal was also observed (FIG. 3C).

Telomere maintenance in human cell lines can occur by at least two pathways: a telomerase-mediated elongation, and a telomerase-independent elongation that may involve recombination, known as Alternative Lengthening of Telomeres (ALT). The fact that elongation of the telomeres in cells expressing A-TRF1$^{66-385}$ was gradual indicates that this A-TRF is involved in the telomerase-dependent pathway. Further evidence for this conclusion is that while the ALT pathway results in telomeres that are extremely heterogeneous in length, often extending over a 30 kb size range, the telomeres in the A-TRF1$^{66-385}$ expressing cell lines maintained approximately the same length heterogeneity as the parental HT1080 cells (FIG. 3). Therefore, the present results indicate that the A-TRF and by analogy TRF1 function in the telomerase-dependent pathway of telomere maintenance.

Figure 4:
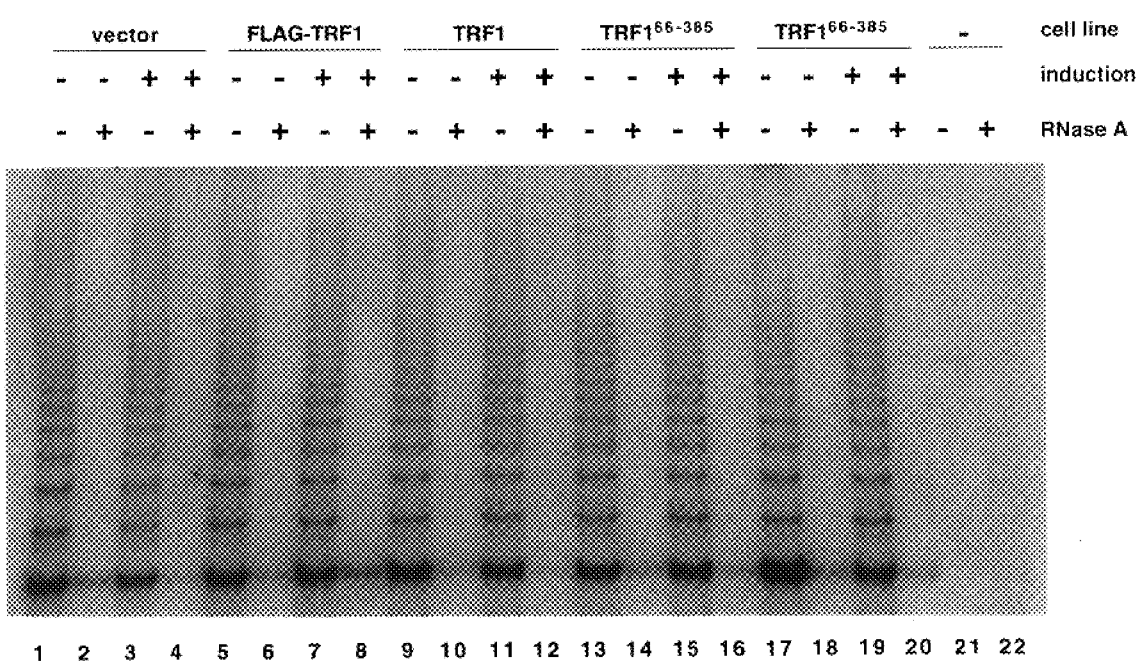
FIG. 4. Overexpression of TRF1, FLAG-TRF1, or A-TRF1$^{66-385}$ do not affect telomerase activity: TRAP (Telomeric Repeat Amplification Protocol) assays for telomerase activity on HT1080tTA clones expressing the indicated TRF1 alleles. Extracts from cell lines B7 (lanes 1–4), C20 (lanes 5–8), D16 (lanes 9–12), K4 (lanes 13–16) and K15 (lane 17–20) were prepared after growth for 28 PDs in the presence (-induction) or absence (+induction) of (-induction) of doxycycline and assayed for telomerase activity as described previously. Lanes 21–22 contain control reactions in the absence of extract. Even lanes contain reactions performed in the presence of 80 ng heat treated RNase A.
Figure 5:
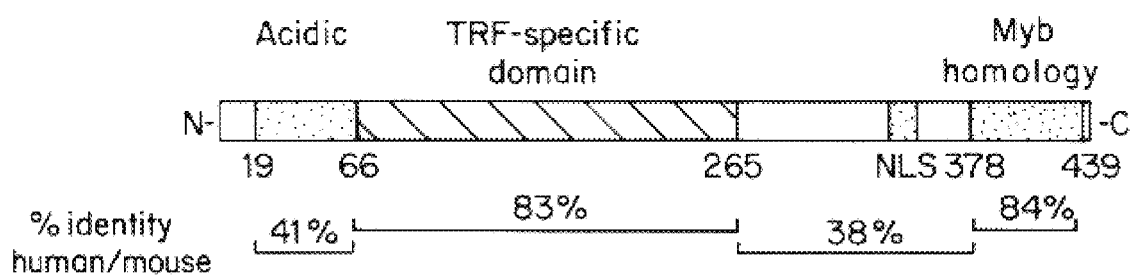
FIG. 5. Schematic of the domains of human TRF1 (hTRF1) and their conservation in mouse TRF1 (mTRF1)

Furthermore, the effects of TRF1 and its corresponding dominant negative mutant, determined in the present study, are consistent with TRF1 being a negative regulator of telomerase-mediated telomere elongation. Additional studies were therefore undertaken to learn what role TRF1 plays in the regulation telomerase activity. Extracts from cells expressing full length TRF1, the FLAG-tagged version of the protein, or the dominant negative allele were examined for telomerase activity using the PCR-based TAP assay. Similar telomerase activity was detected in each of the cell lines in Table 1 and no difference was found between cells grown in the presence or absence of doxycycline (FIG. 4). In each case, the telomerase activity was inhibited by mild RNase A treatment, as expected since telomerase is a ribonucleoprotein reverse transcriptase. The results also eliminated the possibility that TRF1 modulates telomere dynamics through a effecting the expression of telomerase activity (FIG. 4).

Taken together these results indicate that one function of TRF1 is to control telomere length, revealing an interesting parallel with the yeast telomeric proteins Rap1p and Ta1p. TRF1 is also inferred to have a negative effect on telomere length maintenance by telomerase. Since TRF1 affected telomere length without changing the telomerase activity in cell extracts, TRF1 appears to provide a negative feedback signal to telomerase at individual telomeres. According to this model, longer telomeres (elongated by telomerase) recruit more of the telomerase inhibitor TRF1, than shorter telomeres. As a result elongated telomeres will exert a stronger negative feedback effect on telomerase eventually leading to a complete inhibition of the enzyme. Such telomeres may then undergo gradual telomere shortening with successive rounds of replication until they no longer bind sufficient TRF1 to inhibit telomerase. The resulting telomere length homeostasis is a dynamic process governed by expression levels of TRF1 and telomerase. The presence of a critical concentration of TRF1 could either limit the accessibility of the telomere terminus to telomerase or modulate the activity of the enzyme once it is bound to the chromosome end. It has not yet been determined whether the interaction between TRF1 and telomerase is direct or involves other telomere associated proteins. It should also be noted that TRF1 could be involved in altering the rate at which telomeres are shortened during DNA replication. Since telomere dynamics have been implicated in human aging and cancer, it is important to further study the contribution of TRF1 to changes in the length of human telomeres in normal, aging, and malignant cells.

EXAMPLE 2

TRF1 IS A DIMER THAT CAN BEND TELOMERIC DNA

INTRODUCTION:

Human TRF1 binds to DNA as a dimer, thus suggesting that, like Rap1p and c-Myb, TRF1 contacts the DNA with two helix-turn-helix motifs. Results obtained with the yeast two-hybrid assay in conjunction with in vitro DNA binding studies implicate the TRF-specific conserved domain in dimerization. The analogy between Rap1p and TRF1 may be further extended by the finding that TRF1, like Rap1p [Vignais and Sentenac, *J. Biol. Chem.*, 264:8463–8466 (1989); Gilson et al., *J. Mol. Biol.*, 231:293–310 (1993); Muller et al., *J. Struct. Biol.*, 113:1–12 (1994)] bends DNA and binds along telomeric repeat arrays without strong cooperative interactions. Based on the conservation of this property in human and yeast telomeric proteins, DNA bending appears to be relevant to telomere function in vivo.

MATERIALS AND METHODS

Coupled in vitro transcription/translation: TRF1 deletion mutants used for the in vitro coupled transcription/translation experiments were cloned in the vector pET28(a) (Promega) in the NcoI and EcoRI sites using PCR-generated fragments. The GFP-TRF1 fusion product was cloned in pBluescriptKS+. PCR-directed mutagenesis was used to eliminate from this construct the start codon of the TRF1 gene by mutating it from ATG to ATT in order to suppress the occurrence of internal translation at this position. The GFP sequence was obtained from pS65T-C I (Clontech). Expression of TRF1 derivatives was achieved by using a rabbit reticulocyte lysate system (Promega) using reaction conditions essentially as described by the supplier. Briefly, between 0.2 to 1 µg of total plasmid DNA was used per 20 µl reaction containing T7 RNA polymerase in the presence of $^{35}$S-methionine (to visualize products on SDS-PAGE) or without labeled amino acids (for gel-shift assays). After the transcription/translation reaction samples were diluted 1:5 with the addition of 80 µl of buffer D [Chong et al., 1995, supra]. Of this mixture, 0.5–5 µl was used in gel-shift reactions.

Gel-shift assays: Gel-shift assays were performed as described previously [Zhong et al., 1992, supra] using labeled restriction fragments as probes. Most of the experiments were performed with a 142 base pair HindIII-Asp718 fragment from the plasmid pTH 12 [Zhong et al., 1992, supra], which contains 12 tandem TTAGGG repeats. In addition, an EcoRI fragment from pTH5 [de Lange et al., Mol. Cell. Biol., 10:518–527 (1990] containing 27 tandem TTAGGG repeats was employed. Competitions were executed with pTH5. The source of TRF1 was either in vitro translation product (above) or HeLa TRF1 purified over P11, DEAE, CM-sepharose, a column containing *E. coli* chromosomal DNA, and a column containing TTAGGG repeat DNA [Chong et al., 1995, supra]. All detectable TTAGGG repeat binding activity in this fraction could be super-shifted with a TRF1 specific antibody that does not react with TRF2 [Ludérus et al., 1996, supra].

Yeast two-hybrid analysis: LexA-TRF1 hybrids were generated by PCR amplification of DNA sequences encoding the indicated amino acids from a plasmid containing the full length hTRF1 cDNA (phTRF1.4.7, [Chong et al., 1995, supra)] followed by insertion into the EcoRI and BamHl sites of vector pBTM 116 [Bartel et al., *Using the two-hybrid system to detect protein-protein interaction*, IRL Press, Oxford, pp. 153–179 (1993)]. GAD-TRF1 hybrids were generated similarly using vector pACT2 (Clontech). All fusion proteins contained a few additional amino acids (encoded by vector linker sequences) at their carboxyl termini. Expression of the LexA-TRF1 fusion proteins was verified by Western blotting using an anti-LexA antibody.

Two-hybrid experiments were performed in the yeast strain L40 (MATa his3Δ200 trp1-901 leu2-3, 112ade2 LYS: . (lexAop) -HIS3 URA3:: (lexAop)$_8$-lacZ) [Hollenberg et al., *Mol. Cell Biol.*, 15:3813–3822 (1995)]. β-galactosidase activities were measured essentially as described [Guarantee, *Methods Enzimol.*, 101:181–191 (1983)] except that cells were disrupted by freeze-thawing using liquid N$_2$. The average value of three individual transformants for each set of plasmid constructs is reported. Values from individual transformants differed by less than 30% from the average.

DNA bending assay: PCR primers were used to generate DNA fragments with the composition indicated in FIG. 9 using pTH3, pTH6, and pTH12 [Zhong et al., 1992, supra] as templates, which contain 3, 6, and 12 tandem TTAGGG repeats, respectively. The products were end-labelled with $^{32}$P-γ-ATP and polynucleotide kinase and the labelled fragments were isolated by preparative acrylamide gel-electrophoresis. Gel-shift reactions with partially purified HeLa TRF1 were performed as described above and the migration of the complexes was analyzed as described by Ferrari et al. [Ferrari et al., 1992, supra], and Thompson and Landy [*Nucl. Acids Res.*, 16:9687–9705 (1988)].

Expression of human TRF1 (hTRF1) in insect cells: An N-terminally histidine-tagged version of human TRF1 was cloned in the baculovirus expression vector pBacPak8 (Clontech). This vector was used to co-transfect insect Sf21 cells together with linearized baculovirus BacPak6 (Clontech). Recombinant viruses were plaque-purified, screened for TRF1 expression, and amplified. For protein production, a 100 ml suspension culture of Sf21 cells was infected at an m.o.i. of ~10 pfu/cell and harvested after 40 hours. Cells were washed twice in PBS and resuspended in 4 ml of 5 mM imidazole, 500 mM NaCl, 20 mM Tris-HCl pH 7.9. After sonication the extract was centrifuged on a SW55 rotor at 20,000 rpm for 20 minutes at 4° C. The supernatant was filtered through a 0.45 µm filter and applied batch-wise to 400 µl (settled volume) of Ni-charged Sepharose resin (Pharmacia). After extensive washing of the resin, TRF1 was eluted with 2 ml of 1 M imidazole, 500 mM NaCl and 20 mM Tris-HCl pH 7.9. The purified protein was dialyzed against buffer D containing 0.3 mM KCl [Chong et al., 1995, supra]. As judged from Coomassie staining, the resulting hTRF1 protein appeared to be 95–99% pure.

Circularization assay: Asp718-cut kinase end-labeled 217 bp DNA fragment containing an array of 27 TTAGGG repeats was used. The DNA was incubated for 20 minutes at room temperature either with active or heat-inactivated (55° C. for 30 minutes) baculovirus-expressed hTRF1 in 20 mM Hepes-KOH pH 7.9, 200 mM KCl, 10 mM MgCl$_2$, 2 mM DTT. For the hTRF1 titration experiments (FIG. 10A) reactions were carried out with 35 ng DNA per ml and hTRF1 protein concentrations that varied from 15 to 2000 ng/ml. For rate measurements (FIG. 10B), the DNA concentration was 40 ng/ml and hTRF1 was added to 500 ng/ml. ATP was added to 1 mM and ligase to 10 U/ml (protein titration) or to 1000 U/ml (rate measurements). Ligation reactions were performed at 23° C. and allowed to proceed for 30 minutes (protein titration) or from 0 to 128 minutes (rate measurements). Reactions were stopped by the addition of ½ volume of stop buffer (75 mM EDTA, 3 mg proteinase K/ml, 15% glycerol) and incubation at 55° C. for 15 minutes. Exonuclease treated samples were phenol extracted, ethanol precipitated, resuspended in 20 µl of 40 mM Tris-HCl pH 7.5, 20 mM MgCl$_2$, 50 mM NaCl and 50 units of T7 gene6 exonuclease (USB) and incubated for 2 hours at 37° C. Digestions were terminated by the addition of ½ volume of stop buffer and incubation at 55° C. for 15 minutes. Samples were run on 6% polyacrylamide gels in TBE. Quantitation of products was obtained by PhosphorImager (Molecular Dynamics).

Figure 6A:
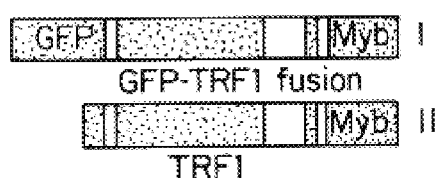
FIGS. 6A–6C. Human TRF1 (hTRF1), binds DNA as a dimer.
Figure 6B:
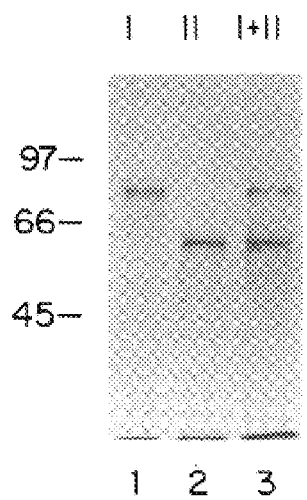

RESULTS hTRF1 binds telomeric DNIA as a dimer: TRF1 harbors only a single Myb repeat, and therefore might bind to DNA as a homodimer. Cloned TRF1 protein produced by in vitro translation in a rabbit reticulocyte lysate is known to bind to DNA probes containing 12 telomeric tandem repeats (the optimal TRF1 binding site) resulting in a complex that co-migrates with hTRF1 purified from HeLa cells [Chong et al., 1995, supra]. This system was employed to synthesize two hTRF1 derivatives of different sizes and study the gel-shift complexes formed by mixtures of these proteins, a strategy employed by Hope and Struhl to show dimerization for GCN4 [Hope and Struhl, *EMBO J.*, 6:2781–2784 (1987)]. A larger derivative of hTRF1 (I in FIG. 6A) was created by fusing the 26-kDa Green Fluorescent Protein (GFP) onto the N-terminus. As expected, in vitro translation of the GFP-TRF1 fusion and hTRF1 (II in FIG. 6A), resulted in two polypeptides that differed by approximately 26 kDa in their apparent MW (FIG. 6B, lanes 1 and 2).

Figure 6C:
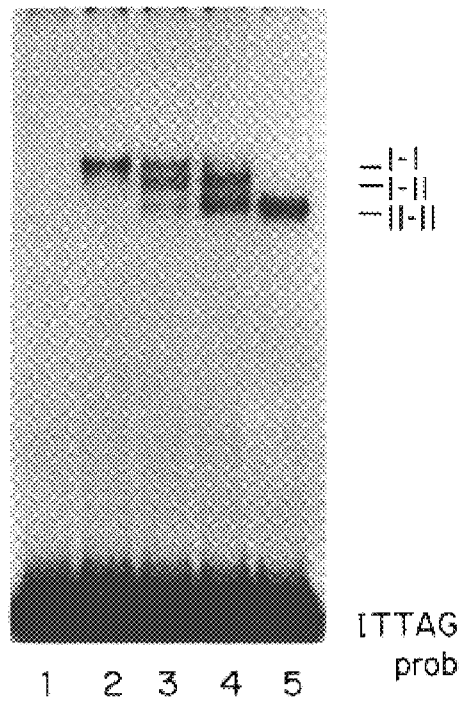

Both forms of hTRF1 were active for DNA binding and gave rise to gel-shift complexes of different migration behavior with the larger protein creating a slower migrating complex (FIG. 6C, lanes 2 and 5). When the two hTRF1 derivatives were co-translated (FIG. 6B, lane 3), the same two gel-shift complexes were apparent (FIG. 6C, lanes 3 and 4). In addition, a third complex was formed that migrated to an intermediate position in the native gel. This third complex was not observed in binding reactions with either of the hTRF1 derivatives alone (FIG. 6C), indicating that its formation depended on the presence of both proteins. Furthermore, the ratio of the three complexes was influenced by the ratio of the two plasmids added to the coupled in vitro transcription/translation system (FIG. 6C).

Since the third complex migrated in between the complexes observed with each TRF1 derivative alone, it is likely to contain an intermediate protein mass. The simplest interpretation of these results is that hTRF1 binds to DNA as a dimer. Acc ording to this interpretation, the slowest migrating complex represents a homodimer of the GFP-TRF1 fusion, the fastest migrating complex represents a homodimer ofhTRF1, and the middle complex represents a heterodimer formed by interaction of these two polypeptides. No gel-shift complexes were observed that could represent hTRF1 monomers. When both proteins were synthesized separately and incubated together, no formation of heterodimers could be demonstrated in subsequent DNA binding assays, suggesting that hTRF1 dimers do not exchange subunits rapidly.

Dimerization is mediated by the TRF-specific conserved domain: To determine which sequences in hTRF1 are responsible for dimer formation, the yeast two-hybrid system was employed [Fields and Song, *Nature*, 340:245–246 (1989)]. Co-expression of full length HTRF1 fused to LexA (LexA-TRF1) and full length hTRF1 fused to the GAL4 activation domain (GAD-TRF1) resulted in transcriptional activation of the lacZ reporter gene that was dependent on the TRF1 sequences in both hybrids (FIG. 7). Moreover, activation was not restricted to the LexA reporter system, since similar activation was observed when hTRF1 was fused to the GAL4 DNA binding domain.

First it was determined whether the Myb repeat was required for TRF1-TRF1 interaction. Deletion of the carboxyl-terminal 119 amino acids of TRF1 (LexAΔ320-C) from both the LexA- and the GAD-TRF1 hybrids did not diminish activation, indicating that the Myb domain was not required for interaction.

To further define the dimerization domain, a series of carboxyl- and amino-terminal deletions of LexA-TRF1 was tested for interaction with GAD-TRF1. Deletion of the C-terminal 25% of TRF1 (LexAΔ263-C) had no effect on activation. In contrast, partial (LexAΔ210-C) or complete (LexAΔ68-C) removal of the conserved domain abolished the interaction with GAD-TRF1.

Deletion of the amino terminus of TRF1 demonstrated that the acidic domain was not required for dimerization. LexAΔN-66 displayed a lower, but reproducible level of activation that was dependent on the presence of GAD-TRF1 and not found with GAD alone. Further deletion into the amino terminal region of the conserved TRF-specific domain (LexAΔN-83) completely abolished activation.

While each of the fusion proteins was stably expressed as determined by Western blotting (see Materials and Methods), the possibility that the lack of activity of LexAΔ210-C, LexAΔ68-C, and LexAΔN-83 is due to missfolding of these deletion mutants could not be excluded.

The amino- and carboxyl-terminal deletions suggested that the TRF-specific conserved domain was required for dimerization. To determine whether this part of TRF1 was sufficient for the interaction, a LexA-TRF1 fusion protein containing only the conserved domain (LexA66-263) was co-expressed with GAD-TRF1. The resulting activation of the reporter gene demonstrates that the TRF-specific conserved domain is both necessary and sufficient for dimerization with TRF1.

Certain LexA-TRF1 derivatives (specifically, LexAΔ263-C, LexAΔ68-C, and LexA66-263) were found to weakly activate transcription of the LexA reporter gene in a manner that is independent of TRF1 sequences in the GAD fusion partner (FIG. 7). Thus, both the acidic domain and the TRF-specific conserved domain have some intrinsic ability to activate transcription in this context.

hTRF1 dimers require two Myb domains for DNA binding in vitro: hTRF1 deletion mutants were tested by gel-shift assay of in vitro synthesized proteins for their ability to bind to telomeric DNA (FIG. 8). While full length hTRF1 bound to a $[TTAGGG]_{12}$ probe in this assay (FIG. 8B, lane 5), hTRF1 truncated at position 320 (Δ320-C) did not bind to DNA (FIG. 8B, lane 4). Since this deletion removes the Myb domain, the lack of DNA binding with Δ320-C truncation is consistent with the requirement of the Myb motif for interaction with the telomeric site. However, while the Myb domain is necessary for DNA binding, it does not appear to be sufficient for this activity, as shown by the lack of complex formation with deletions ΔN-196 and ΔN-376 (FIG. 8B, lanes 2 and 3).

These results suggested that dimer formation is a prerequisite for DNA binding, as both ΔN-196 and ΔN-376 lack the dimerization domain as defined by the two-hybrid assay. In agreement with this view, removal of the first 28 or 46 amino acids did not affect the DNA binding activity of hTRF1 (FIG. 8C, lanes 3 and 4). In addition, ΔN-65 was clearly capable of DNA binding, albeit with diminished activity (FIG. 8C, lane 5).

The requirement for dimerization could be explained if stable interactions with telomeric DNA depend on the coordinate binding of two Myb repeats. To test this possibility, it was determined whether hTRF1 dimers need to contain both Myb repeats to bind to DNA. To this end, full length hTRF1 was co-translated with increasing amounts of the ΔC-320 mutant under conditions known to generate heterodimers (FIG. 8D). The resulting mixtures were found to contain a single DNA binding activity forming a complex that co-migrated with the full length hTRF1 complex. No second, smaller complex predicted to occur if the heterodimer lacking the second Myb motif could bind to DNA was observed. Furthermore, as more mutant hTRF1 was synthesized in the reactions, the abundance of the hTRF1 gel-shift complex diminished (FIG. 8D), as would be expected if heterodimers with only a single Myb motif failed to bind DNA. These results were consistent with the notion that two Myb motifs are required for the formation of a stable DNA-protein complex and indicated that this requirement is met by the formation of hTRF1 homodimers. The positioning of the two Myb motifs on the telomeric DNA may be important, since a simple fusion of the dimerization domain onto the Myb domain did not result in active protein (Δ263-376, see FIG. 8A).

hTRF1 bends DNA: c-Myb, the plant transcription factor Myb.Ph3, and Rap1p each induce a bend in their target site [Vignais and Sentenac, 1989, supra; Gilson et al., 1993, supra; Muller et al., 1994, supra; Saikumar et al., *Oncogene*, 9:1279–1287 (1994); Solano et al., *Plant J.*, 8:673–682 (1995)]. In order to determine whether hTRF1 shares this feature, an approach analogous to the circular permutation assay developed by Wu and Crothers was employed [Wu and Crothers, *Nature*, 308:509–513 (1984)]. To generate probes for this assay, PCR amplification was used to produce five DNA fragments of equal length, each harboring a hTRF1 binding site at a different position relative to the ends of the molecule (FIG. 9A). Using this strategy on three similar plasmid templates with variable TTAGGG repeat array lengths (FIG. 9A), three sets of permuted probes were generated which carried 3, 6, or 12 tandem TTAGGG repeats (referred to as 3mer, 6mer and 12mer probes).

Labeled DNA probes were incubated with purified HeLa TRF1 under conditions in which one TRF1 dimer binds per probe molecule [Zhong et al., 1992, supra] and the mobility of the resulting complexes was analyzed on native polyacrylamide gels. The permuted sets of fragments had the same electrophoretic mobility as expected from their equal lengths. Complexes were formed with each of the permuted 6mer and 12mer probes with approximately the same efficiency and this binding was TRF1-specific as demonstrated by competition with a plasmid carrying an array of TTAGGG repeats (FIG. 9B). As shown in FIG. 9B for the 6mer and 12mer probes, an effect of the position of the hTRF1 binding site within the probes was observed. Slower migrating complexes were obtained when the binding site for hTRF1 was located more centrally in the DNA molecule, consistent with the induction of DNA bending upon hTRF1 binding. A similar anomalous migration pattern indicative of bent DNA was observed with the hTRF1 complexes formed on the set of 3mer probes but, in agreement with a previous report [Zhong et al., 1992, supra], the binding was very weak.

To determine the locus and extent of DNA bending, the relative mobility of each hTRF1-DNA complex was plotted against the flexure displacement and these data points were interpolated with a quadratic function [Ferrari et al., 1992, supra] to derive an estimate of the deviation from linearity (FIG. 9C). Values ranging from 64–66° were found in five experiments with the 6mer set and similar values of 57° and 59° resulted from two experiments with the 12mer probes, indicating that TRF1 induced a shallow distortion in which the DNA deviates from linearity by approximately 60°. A similar bending angle was deduced when the equation derived by Thompson and Landy was used [Thompson and Landy, 1988, supra]. The minimum of the parabola maps the site of bending to approximately two base pairs 5' of the center of the TTAGGG repeat arrays in both sets of probes. Since it is not known where TRF1 binds within the TTAGGG repeat arrays, it could not be determined where this bend is in relation to the position of TRF1 in the probes.

In some cases, the shape of the protein itself, rather that a protein-induced bend, is thought to be responsible for the anomalous migration of DNA-protein complexes in the circular permutation assay [Gartenberg et al., *Proc. Natl. Acad. Sci. USA*, 87:6034–6038 (1990)]. Therefore independent evidence that hTRF1 distorts its binding substrate was sought through the use of the circularization assay [Kotlarz et al., *EMBO J.*, 5:799–803 (1986)]. Since the rate of intramolecular ligation of small DNA fragments is affected by the presence of a natural or protein-induced DNA bend, we determined the effect of hTRF1 on circularization of a 217 bp restriction fragment containing 27 tandem TTAGGG repeats. The reaction was monitored by gel-electrophoresis of samples that were treated with T7 gene6 exonuclease to facilitate identification of the exonuclease-resistant ligation product representing the circular form of the 217 bp fragment. In three independent experiments, the appearance of the circular ligation product was enhanced when active baculovirus-derived hTRF1 was added to the reactions and the formation of the circle depended on the concentration of the hTRF1 protein in the reactions (FIG. 10A). At the highest protein concentrations, the enhancing effect of TRF1 is partially lost, possibly because the binding of multiple TRF1 dimers to one DNA molecule cancels out the bending angles. No enhancement was observed when the hTRF1 protein was heat-inactivated for 30 minutes at 55° C. before addition to the reactions (FIG. 10B). In addition, no enhancement occurred with a 192 bp fragment that does not contain TTAGGG repeats, indicating that the effect is due to TRF1 binding to its telomeric site. The extent to which TRF1 enhanced the rate of circularization was determined as shown in FIG. 10B or without prior treatment with exonuclease. In three experiments TRF1 was found to enhance circularization by 8- to 16-fold at early time points. At later time points (>1 hour), the effect was less strong (2-fold) possibly because TRF1 is inactivated in the reactions. Rate measurements using the 192 bp control fragment that lacked a TRF1 binding site, showed that TRF1 did not have a non-specific effect on the rate of DNA circularization. These results are consistent with the notion that TRF1 induces a bend in telomeric DNA.

hTRF1 dimers bind along TAGGG repeat arrays without strong cooperativity: The next question was how does hTRF1 interact with long arrays of TTAGGG repeats that represent more closely the extended tracts of telomeric repeats at human chromosome ends? Gel-shift experiments were performed with a DNA probe containing an array of 27 telomeric repeats and increasing amounts of partially purified hTRF1 from HeLa nuclear extract. As more protein was used in the reactions, larger complexes were observed (FIG. 11) which increased in size in four incremental steps, consistent with the acquisition of four dimeric hTRF1 units by the [TTAGGG]$_{27}$ probe. It is not excluded that this probe can accommodate additional hTRF1 dimers; such higher order complexes might not be resolved easily by the gel-system used in these experiments. Thus, consistent with previous results and the binding of hTRF1 to probes with 3 TTAGGG repeats [Zhong et al., 1992, supra], the binding of four hTRF1 dimers to a [TTAGGG]$_{27}$ probe argues that the minimal hTRF1 binding site is not larger than 7 tandem repeats.

The ability of hTRF1 to interact with itself to form dimers raised the possibility that hTRF1 might display cooperative interactions when binding along the length of long telomeric tracts. However, the recruitment of additional hTRF1 dimers to hTRF1/DNA complexes does not appear to be strongly enhanced compared to binding to the free probe (FIG. 11).

The appearance of additional bound units of hTRF1 with increasing amounts of HeLa nuclear extract seems to be progressive and gradual. Note for example the persistence of complex II (containing two hTRF1 dimers) throughout the titration. Thus, no evidence was found for strong cooperative interactions on these and other probes with long telomeric arrays.

DISCUSSION

This study revealed several novel features of TRF1 that are relevant to its function at mammalian telomeres. Human TRF1 was found to form a homodimer through interactions involving the TRF-specific, conserved domain in the N-terminal half of the protein. Dimerization was a prerequisite for DNA binding, presumably because it brings together two copies of the second domain conserved in human and mouse TRF1, the Myb-related DNA binding motif. In addition, TRF1 was found to form extensive protein arrays along the telomeric DNA and binding of TRF1 induced a shallow bend in its telomeric site. These results reveal striking similarities between TRF1 and the yeast telomeric protein Rap1p and argue that these proteins may have an architectural role at telomeres in yeasts and mammals respectively that has not been previously appreciated.

Whereas the majority of Myb-related DNA binding proteins carry two or three Myb repeats, the TRF proteins belongs to the class of Myb proteins that harbor only a single Myb motif. TRF1 binds as a homodimer, thus creating an overall architecture that is functionally similar to other Myb proteins in the sense that two Myb-repeats are linked in one protein. In addition, similar to what is seen with c-Myb and Rap1p [Henry et al., 1990, supra; Saikumar et al., 1990, supra], both Myb repeats in the TRF1 dimers are required for DNA binding, indicating a unifying theme for Myb-related DNA binding proteins: the use of a pair of helix-turn-helix (HTH) motifs to recognize DNA. Since its primary sequence indicates that TRF2 has a similar domain structure, it is likely that this theme of twin Myb repeats juxtaposed on DNA by dimerization extends to this telomeric protein.

The present results suggest that dimerization may also play a role in DNA site recognition by other single-Myb repeat proteins, such as Tbf1p, IBP, BFP-1, MybSt1, Adf1, and CHD1 [England et al., 1991. supra; Liu and Tye, *Genes Dev.*, 5:49–59 (1991); da Costa e Silva et al., 1993, supra; Baranowskij et al., 1994, supra; Lugert and Werr, 1994, supra; Stokes and Perry, 1995, supra]. Interestingly, many of these proteins have been shown to interact with a DNA recognition sequence that features direct repeats, consistent with a DNA binding mode in which homodimerization positions two identical helix-turn-helix motifs in contact with tandemly repeated sites. These considerations raise the possibility that single-Myb repeat proteins in general may interact with direct repeats.

While in c-Myb the two HTH motifs come in direct contact with each other, contacting a single short site in the major groove, in Rap1p the two Myb repeats are separated by a linker, contacting two distinct, directly repeated sites. Since c-Myb and Rap1p clearly have different interactions with their recognition sites, it is not possible to predict the structure of the TRF1-DNA complex at this stage. Nevertheless, the binding of tandem repeats by TRFs appears to be a direct reflection of the presence of two identical recognition helices in the dimers and that the two HTH motifs are used independently in contacting adjacent repeats. Several examples of homodimeric factors that bind to direct repeats have been reported in both yeast (e.g. HAP1[Zhang and Guarantee, *Genes Dev.*, 8:2110–2119 (1994)]) and higher eukaryotes (e.g. RAR [Towers et al., *Proc. Natl. Acad. Sci. USA*, 90:6310–6314 (1993)]). These factors dimerize through symmetrical protein-protein interactions and their ability to bind to direct repeats is attributed to free swiveling of the DNA binding domain around a flexible linker. The poorly conserved domain of TRF1 located between the dimerization domain and the Myb repeat similarly functions as a flexible hinge region.

The finding that TRF1 dimerization occurs in the yeast two-hybrid system indicates that TRF1 dimerizes independent of its binding to telomeric DNA. Further evidence for such preformed TRF1 dimers was obtained from the fractionation of HeLa derived TRF1 on a SuperDex gel-filtration column on which TRF1 migrates as a 100–120 kDa protein, consistent with a homodimer of the 50-kDa hTRF1 polypeptide. The exchange of subunits between TRF1 dimers has not been observed, suggesting that, once formed, TRF1 dimers may be relatively stable.

Bilaud et al. have shown that the isolated Myb repeat domains of both TRF1 and TRF2 can bind TTAGGG repeats in a SouthWestern assay [Bilaud et al., 1996, supra]. While it is not clear that the binding activity of these fragments is similar to full length protein, it seems likely that in the SouthWestern assay the attachment of the Myb domains to a solid matrix can (at least partially) substitute for the requirement for dimerization. A second possibility is that the isolated Myb domain of the TRF proteins can form a complex with DNA under conditions of high DNA and/or protein concentration.

Each of the activities of TRF1 described here, binding to DNA with two Myb repeats, absence of strong cooperative interactions, and DNA bending are also seen with Rap1p, the major duplex telomeric DNA binding protein in yeast (reviewed in [Smith and de Lange, 1997]). The resemblance of TRF1 to Rap1p is particularly striking because the primary sequences of these proteins are not similar, indicating that biochemical features of these telomeric proteins are conserved even as their primary sequences evolve rapidly. The identified properties of these telomeric proteins appear to be conserved because they reflect key aspects of their function at telomeres.

DNA bending by telomeric proteins could induce a higher order structure at telomeres that is required for their function. It is noteworthy that human telomeres appear to be very compact structures when visualized by immunogold EM [Ludérus et al., 1996, supra], suggesting that some protein is responsible for their tight packaging in interphase nuclei. The ability of TRF1 to bend DNA could contribute considerably to the overall configuration of the telomeric DNA. Although a single TRF1 dimer induced only a minor distortion in vitro, the acquisition of as few as three TRF1 binding units along the telomeric tracts could result in the folding back of the telomere on itself. Thus, TRF1 binding could drastically alter the overall structure of the telomeric complex in a manner that is important for telomere function. Duplex telomeric DNA binding proteins in yeasts have been implicated in telomere length regulation [Conrad et al., *Cell*, 63:739–750 (1990); Lustig et al., *Science*, 250:549–553 (1990); McEachern and Blackburn, 1995, supra; Zakian, 1995a, supra; Krauskopf and Blackburn, 1996, supra, in suppression of telomere-telomere recombination [Li and Lustig, *Genes Dev.*, 10:1310–1326 (1996)], in telomeric silencing [Kyrion et al., *Mol. Cell. Biol.*, 12:5159–5173 (1992); Shore, 1994, supra; Cooper et al., 1997, supra), and in telomere function in meiosis or sporulation [Cooper et al., 1997, supra]. Each of these aspects of telomere function may well depend on a critical configuration of the telomeric complex achieved (in part) via DNA distortions.

In summary, TRF1 is a mammalian telomeric protein that binds to the duplex array of TTAGGG repeats at chromosome ends. TRF1 has homology to the DNA binding domain of the Myb family of transcription factors, but unlike most Myb-related proteins, TRF1 carries one rather than multiple Myb-type DNA binding motifs. TRF1 binds DNA as a dimer using a large conserved domain near the N-terminus of the protein for TRF1-TRF1 interactions. Dimerization was observed both in a complex with DNA as well as in the yeast two-hybrid assay. TRF1 dimers were found to require both Myb repeats for the formation of a stable complex with DNA, indicating a parallel between the DNA binding mode of TRF1 and other Myb-related proteins. TRF1 was found to have a number of biochemical similarities to Rap1p, a distantly-related DNA binding protein that functions at telomeres in yeast. Rap1p and hTRF1 both require two Myb motifs for DNA binding and both factors bind along their cognate telomeric sequences without showing strong cooperative interactions between adjacent proteins. Furthermore, hTRF1 was found to bend its telomeric site to an angle of ~120°. Since Rap1p similarly distorts telomeric DNA, DNA bending appears to be important for the function of telomeres in yeast and mammals.

EXAMPLE 3

TRF2 PROTECTS HUMAN TELOMERES FROM END TO END FUSIONS

Summary

TRF2 is found to be required for cellular proliferation and for the protection of chromosome ends in human cells. Overexpression of two deletion derivatives of TRF2 lacking the basic N-terminus induced an irreversible growth arrest with characteristics of cellular senescence. A strong dominant negative allele causing the loss of endogenous TRF2 from telomeres, induced end-to-end chromosome fusions detectable in metaphase and anaphase cells. Telomeric DNA persisted at the fusions, demonstrating that TTAGGG repeat arrays per se are not sufficient to maintain telomere integrity. TRF2 protects chromosome ends from fusion, through the maintenance of the correct structure at telomere termini.

Introduction

Telomeres in somatic human cells shorten by 50–200 bp per cell division [Cooke and Smith, Cold Spring Harbor Symp. Quant. Biol., LI:213–219 (1986); Harley et al., Nature, 345:458–460 (1990); Hastie et al., Nature, 346:866–868 (1990); reviewed in Harley et al., In Telomeres, Cold Spring Harbor Press, Cold Spring Harbor, N.Y. (1995)]. Programmed telomere shortening in normal human cells may function as a tumor suppresser mechanism that limits the growth potential of transformed cells [reviewed in de Lange, In Telomeres, Cold Spring Harbor Press, Cold Spring Harbor, N.Y. (1995)]. In agreement, telomere length is strongly correlated with the proliferative capacity of normal human cells and the catalytic subunit of telomerase (hTRT/hEst2p) is upregulated in human tumors and immortalized cells [Allsopp et al., Proc. Natl. Acad. Sci. USA, 89:10114–10118 (1992); Meyerson et al., Cell, 90:785–795 (1997); Nakamura et al., Science, 277:955–959 (1997)].

Loss of telomere function in human cells results in the formation of dicentric chromosomes and other abnormalities created through end-to-end fusions [Counter et al., EMBO J., 11: 1921–1929 (1992)]. Both in senescent cells and in tumor cells, dicentric chromosomes, rings, and sister-chromatid fusions are correlated with critically shortened telomeres [reviewed in de Lange, In Telomeres, Cold Spring Harbor Press, Cold Spring Harbor (1995)]. These observations, taken together with evidence for a protective role of telomeres from yeast, ciliates, flies, and maize, have led to the supposition that chromosome ends lacking telomeric DNA fail to recruit a terminal protein complex required for their protection. However, there has been no direct evidence of telomeric proteins protecting chromosome ends from end-to-end fusion and it has remained obscure how such factors might act.

Two human telomeric DNA binding proteins have been identified herein. TRF1 was isolated as a double-stranded TTAGGG repeat binding protein from HeLa cells [Chong et al., Science, 270:1663–1667 (1995); U.S. patent application Ser. No. 08/519,103 filed Aug. 25, 1995; U.S. patent application Ser. No. 08/938,052 filed Sep. 26, 1997; both of which are hereby incorporated by reference in their entireties]. This factor is a homodimeric protein with a C-terminal helix-turn helix motif similar to the Myb and homeodomain DNA binding folds [Bianchi et al., EMBO J., 16:1785–1794 (1997)] [reviewed in Smith and de Lange, Trends in Genetics, 13:21–26 (1997); and Konig and Rhodes, Trends Biochem. Sci., 22:43–47 (1997)]. TRF2 carries a similar C-terminal Myb motif but is different from TRF1 in that its N-terminus is very basic rather than acidic [Bilaud et al., Nature Genetics, 17:236–239 (1997); Broccoli et al., Nature Gen., 17:231–235 (1997); U.S. patent application Ser. No. 8/938,052 filed Sep. 26, 1997] (FIG. 12A). Both proteins bind specifically to double-stranded TTAGGG repeats in vitro and are located at telomeres in vivo. The two TRFs are ubiquitously expressed and current evidence is consistent with most human telomeres containing both factors bound simultaneously throughout the cell cycle [Chong et al., Science, 270:1663–1667 (1995); U.S. patent application Ser. No. 08/519,103 filed Aug. 25, 1995; Broccoli et al., Nature Gen., 17:231–235 (1997); U.S. patent application Ser. No. 08/938,052 filed Sep. 26, 1997; Smith and de Lange, Trends in Genetics, 13:21–26 (1997); van Steensel and de Lange, Nature, 385:740–743]. TRF1 has been shown to be a negative regulator of telomere length maintenance [van Steensel and de Lange, Nature, 385:740–473; Example 1, above]. A key role for TRF2 is demonstrated for a second function of telomeres, the protection of chromosome ends from end-to-end fusion, is disclosed herein.

Experimental Procedures

Expression vectors. The cDNA encoding full-length human TRF2 was placed under the tetracyclin-controlled promoter by cloning the EcoRI fragment of plasmid phTRF216-1 [Broccoli et al., 1997; U.S. patent application Ser. No. 08/938,052 filed Sep. 26, 1997] into vector pUHD10-3, resulting in plasmid pTethTRF2. To facilitate the creation of constructs encoding truncated proteins with an N-terminal FLAG-tag, expression vector pTetNFLAG was constructed by inserting a linker encoding a FLAG tag and an EcoRI site into the SacII and BamHI sites of pUHD10-3. Next, a nucleic acid encoding TRF2$^{\Delta B}$ (amino acid sequence SEQ ID NO:16) and a nucleic acid encoding TRF2$^{\Delta B \Delta M}$ (amino acid sequence SEQ ID NO:14) were each cloned into the EcoRI and BamHI sites of pTetNFLAG (in-frame with the FLAG-tag) by PCR cloning, using Pfu-polymerase, plasmid phTRF216-1 as template, with 5'TTGAATTCGAGGCACGGCTGGAAGAG3' (SEQ ID NO:19) as forward primer for both constructs, 5'CGG-GATCCTGTTTCAGTTCATGCCAA3' (SEQ ID NO:20) as backward primer for TRF2$^{45\text{-}500}$ and 5'CGGGATCCTCAT-TCTACAGTCCACTTCTGCT3' (SEQ ID NO:21) as backward primer for TR-F2$^{45\text{-}454}$.

Induction of TRF2 polypeptides in HTC75 cells. The empty vector pUHD10-3 and the pUHD10-3-derived constructs for expression of the TRF2 alleles were each co-transfected with neomycin resistance plasmid pNY-HI into cell line HTC75 using the calcium phosphate co-precipitation. HTC75 is a hygromycin resistant HT1080-derived clonal cell line that stably expresses the tetracyclin-controlled transactivator (tTA) [Gossen and Bujard, *Proc. Natl. Acad. Sci. USA*. 89:5547–5551 (1992); van Steensel and de Lange, *Nature*, 385:740–743 (1997); U.S. patent application Ser. No. 08/800,264 filed Feb. 13, 1997]. Transfected cells were grown in the presence of doxycyclin (100 ng/ml) and G418 (600 (μg/ml). For each construct approximately 25 G418-resistant cell lines were isolated by ring cloning and tested for expression of TRF2 polypeptides after 24 hours of induction. Expression of TPF2$^{\Delta B\Delta M}$ and TRF2$^{\Delta B}$ was tested by immunofluorescence microscopy and western blotting using anti-FLAG antibody M2 (Eastman Kodak); expression of wild-type TRF2 was tested by gelshift assays using a TTAGGG repeat probe and by western blotting using affinity-purified serum #508 (see below). All clones were grown in DMEM supplemented with 10% bovine calf serum or bovine fetal serum and 150 μg G418 per ml. All clones were grown in parallel with or without doxycyclin (100 ng/ml).

Polyclonal antibody against TRF2. A 28-mer peptide (pep28) encompassing amino acid residues 16–42 of human TRF2 (SEQ ID NO:18) with an additional N-terminal cysteine was synthesized (BioSynthesis, Lewisville, Tex.) and conjugated to maleimide-activated Keyhole Limpet Haemocyanin (KLH, Pierce, Rockford, Ill.). Serum from a rabbit immunized with the pep28-KLH conjugate was affinity-purified against pep28 cross-linked to SulfoLink coupling gel (Pierce) using standard procedures [Harlow and Lane, Antibodies, a laboratory manual, Cold Spring Harbor Press (1988)]. The resulting purified antibody #508 reacts specifically with TRF2 in western blotting and immunofluorescence labeling assays. The antibody does not cross-react with TRF1.

Whole-cell extracts. Cells grown in 10 cm dishes were washed with 5 ml cold phosphate buffered saline (PBS), harvested by scraping in 1 ml PBS per dish and centrifuged 2 minutes in an Eppendorf microfuge at setting 4,000 g. Subsequent steps were all carried out on ice or at 4° C. The cell pellets (~4 million cells) was resuspended in 200 μl buffer C (20 mM Hepes-KOH pH 7.9, 420 mM KCl, 25% glycerol, 0.1 mM EDTA, 5 mM MgCl$_2$, 1 mM dithiothreitol, 0.5 mM phenylmethylsulfonyl fluoride, 0.2% Nonidet P-40, 1 μg leupeptin per ml, 1 μg pepstatin per ml, 1 μg aprotinin per ml), incubated for 30 minutes and centrifuged for 10 minutes in an Eppendorf microfuge at 14,000 g. The supernatant was dialyzed 2–5 hrs against 100 ml of buffer D (20 mM Hepes-KOH pH 7.9, 100 mM KCl, 20% glycerol, 0.2 mM EDTA, 0.2 mM EGTA, 0.5 mM dithiothreitol, 0.5 mM phenylmethylsulfonyl fluoride), frozen in liquid nitrogen and stored at −80° C. Protein content of the extracts was measured using the Bradford assay (BioRad, Hercules, CA.) using bovine serum albumin as a standard.

Western blotting. Twenty fg of whole-cell extract proteins were separated on 10% SDS-polyacrylamide gels and transferred to nitrocellulose by electroblotting. Ponceau S staining confirmed equal loading of the samples. Blots were pre-incubated 30 minutes in 10% non-fat milk powder and 0.5% Tween-20 in PBS. All subsequent incubations and washing steps were carried out in 0.1% non-fat dry milk powder and 0.1% (w/v) Tween-20 in PBS. Blots were incubated for 12–16 hours at 4° C. with either anti-FLAG antibody M2 or anti-TRF2 antibody #508, followed by three 10 minute washing steps. Next, blots were incubated 45 minutes with horseradish peroxidase conjugated sheep-anti-mouse (Jackson Immuno Research Labs) or donkey-anti-rabbit antibody (Amersham) and washed three times for 10 minutes. Bound antibody was detected using the ECL kit (Arnersham).

Immunofluorescence labelling and microscopy. The HeLaI.2.11 cell line, a subclone of HeLaI [Saltman et al., *Chromosoma*, 102:121–128 (1993)] bearing telomeres of >25 kb, was transfected by electroporation with pTethTRF2, pTetFLAGhTRF2$^{\Delta B}$, or pTetFLAGhTRF2$^{\Delta B\Delta M}$ together with the tTA-expression vector pUHD15-1 [Gossen and Bujard, *Proc. Natl. Acad. Sci. USA*, 89:5547–5551 (1992)]. Cells were grown for 24 hours on Alcian Blue coated coverslips in the absence of doxycyclin. Fixation and immunostaining were carried out as described [Chong et al., *Science*, 270:1663–1667 (1995); U.S. patent application Ser. No. 08/519,103 filed Aug. 25, 1995; van Steensel and de Lange, *Nature*, 385:740–743 (1997); U.S. patent application Ser. No. 08/800,264 filed Feb. 13, 1997]. TRF2 was detected with polyclonal antibody #508 (see above) raised and affinity purified against an N-terminal peptide of TRF2. The FLAG epitope tag was detected with the M2 anti-FLAG monoclonal antibody (Eastman Kodak). TRF1 was detected with a mouse polyclonal serum (#2) directed against the full length protein or with antibody 371C2. Rabbit antibodies were detected with FITC- or Cy3-conjugated donkey-anti-rabbit antibodies (Jackson ImmunoResearch Labs). Mouse antibodies were detected with FITC-conjugated donkey-anti-mouse antibody (Jackson ImmunoResearch Labs). Control experiments indicated that secondary antibodies did not show any cross-reaction. To exclude that binding of anti-TRF1 (#371C2, [van Steensel and de Lange, *Nature*, 385:740–743 (1997); U.S. patent application Ser. No. 08/800,264 filed Feb. 13, 1997]) and anti-TRF2 (#508) antibodies to endogenous TRF proteins was prevented by anti-FLAG antibody M2 through steric hindrance, the cells were pre-inducated overnight with #371C2 or #508 before adding M2.

Micrographs were recorded on a Zeiss Axioplan microscope with a Kodak DCS200 digital camera. Images were noise-filtered, corrected for background and merged using Adobe Photoshop.

Cell growth curves and Argalactosidase assay. Cells were plated in duplicate at various densities (~0.1–4.0 * 10$^6$ cells/15 cm dish) the day before the experiment. On day 0, all plates were washed three times with medium containing G418 (150 μg/ml), with or without doxycyclin (100 ng/ml). On indicated days cells were harvested and counted, and cell pellets were frozen at −80° C. for isolation of genomic DNA. Whole-cell extracts were prepared from dishes grown in parallel. In most experiments, cells were split at day 4 (1:32–1:4) for day 6 and day 9 time points.

Cells induced for 9 days were stained for β-galactosidase using the method described in Dimri et al. [*Proc. Natl. Acad. Sci. USA*, 92:9363–9367 (1995)], but with phosphate buffer instead of citrate/phosphate buffer. Cells were washed in PBS, pH 7.2, fixed for 5 minutes in 2% formaldehyde/0.2% glutaraldehyde solution in PBS, washed again in PBS (pH 7.2) and stained with X-gal (1 mg/ml) in 150 mM NaCl, 2 mM MgCl$_2$, 5 mM K$_3$Fe(CN)$_6$, 5 mM K$_4$Fe(CN)$_6$, and 40 mm NaPi pH 6.0, pH 4.0 or pH 7.0, for 6 to 12 hours at 37° C.

Chromosome analysis in metaphase and anaphase cells. Four to six days after induction (as indicated in the text) cells were incubated with 0.1 μg demecolcine per ml for 90 minutes, harvested by trypsinization, incubated for 7 minutes at 37° C. in 0.075 M KCl, and fixed in freshly prepared methanol: glacial acidic acid (3:1 vol/vol). Cells were stored at 4° C. and when needed dropped onto wet slides and air dried.

For DAPI staining of DNA, slides with metaphase spreads were incubated 10 minutes in 0.5 μg 4', 6-diamino-2-phenylindole (DAPI)(Sigma) per ml PBS, washed for 2 minutes in PBS, and mounted in 90% glycerol/10% PBS containing 1 mg p-phenylene diamine (Sigma)/ml.

For trypsin banding, metaphase spreads prepared as above were incubated in banding solution (2× trypsin-EDTA (Gibco), 1× Hanks Balanced Salt Solution(Gibco) in water) for 45 to 75 seconds at 37° C. and stained with filtered staining solution (16% Giemsa Blood Staining Solution (J.T.Baker), 4% Giemsa Solution (Fisher) in Tris-Maleic acid buffer pH 5.6) for 60–75 seconds at room temperature.

Anaphase cells were visualized by DAPI staining of cells grown on cover slips for the indicated number of days in the presence or absence of doxycyclin.

FISH. In situ hybridization was executed according to Lansdorp et al. [*Hum. Mol. Gen.*, 5:685–691 (1996)]. Hybridization was performed with 0.5 μg/ml FITC-conjugated$(C_3TA_2)_3$ peptide nucleic acid (PNA) probe (Biotech GmbH), and after washing, the cells were embedded in 90% glycerol/10% PBS containing 1 mg p-phenylene diamine (Sigma Chemical Company, Inc.) per ml, supplemented with 0.2 μg 4',6-diamino-2-phenylindole (DAPI) per ml.

Genomic blotting and Bal31digestion. Isolation of genomic DNA, genomic blotting and telomere-length estimation were carried out as described [van Steensel and de Lange, *Nature*, 385:740–743 (1997); U.S. patent application Ser. No. 08/800,264 filed Feb. 13, 1997]. For the Bal31 nuclease experiment, about 65 μg undigested genomic DNA was incubated at 30° C. with 13 units Bal31 nuclease (mixed, New England Biolabs, Beverly, Mass.) in 390 μl buffer containing 600 mM NaCl, 12 mM $CaCl_2$, 12 mM $MgCl$, 20 mM Tris-HCl, 1 mM EDTA, pH 8.0. At indicated time points, 30 μl samples were taken and inactivated by addition of 2μl 0.5 M EGTA and incubation for 10 minutes at 65° C. Bal31treated DNA samples were extracted with phenol/chloroform, precipitated with ethanol and digested with HinfI and RsaI. To ensure equal loading on agarose gels, all DNA samples were quantified after restriction enzyme digestion by fluorometry using Hoechst 33258 dye.

G-strand overhang assay. The non-denaturing hybridization assay to detect G-strand overhangs was carried out essentially as described [Makarov et al., *Cell*, 88:657–666 (1997)]. $[TTAGGG]_4$ and $[CCCTAA]_4$ oligonucleotide probes were end-labeled using $\gamma$-$^{32}$P-ATP (3000 Ci/mmol, Arnersham) and T4 polynucleotide kinase. Depending on the experiment, 2.5–5.0 μg HinfI/RsaI digested genomic DNA was ethanol-precipitated, resuspended in 21 μl hybridization buffer (50 mM Tris-HCl pH 8.0, 50 mM NaCl, 1 mM EDTA), added to 4 μl labeled probe (8 nM) and incubated 10–16 hrs at 50° C.in a Perkin-Elmer PCR-thermocycler. Hybridized samples were size-fractionated on 0.8% agarose gels in 1×TAE. The gels were dried on Whatman DE-81 filterpaper and exposed to autoradiography film or a PhosphorImager screen. As a control, 4 μg HinfI/RsaI digested DNA was treated for 30 minutes at 30° C. with 0, 10 or 40 Units Mung Bean nuclease (New England Biolabs) in MB buffer (50 mM sodium acetate, 30 mM NaCl, 1 mM ZnSO4, pH 5.0), inactivated by addition of0.01% SDS, and ethanol-precipitated before carrying out the overhang assay. Inspection of the ethidium bromide stained gel confirmed that Mung Bean nuclease did not have any detectable endonuclease activity. Treatment with 40 U of Mung Bean nuclease completely abolished the overhang signal. Annealing with a $[TTAGGG]_4$ probe did not reveal a signal at the position of the telomeres. For quantitation of the G-strand overhangs, hybridization intensity was measured using ImageQuant software by integration of the signal of the entire lane between ~1.5 and 30 kb. DNA samples from cells grown with or without doxycyclin were always analyzed in parallel and run on the same gel.

TRAP assay. Reactions were performed with whole cell extracts as described elsewhere [Broccoli et al., *Proc. Natl. Acad. Sci. USA*, 92:9082–9086 (1995)]. Protein concentrations in the extracts were determined by Bradford assay (BioRad) and 0.5 μg protein was used per extract. RNase digestions were done in parallel to the untreated reaction by addition of 0.2 μg DNase free RNAse A to the telomerase extension reaction.

Results

Inhibition of TRF2 by TRF2 analogs. An inducible expression system was used to further examine the role of TRF2 at human telomeres. This expression system is based on the cell line HTC75, a Tetracyclin-inducible derivative of the human fibrosarcoma cell line HT1080 was used. This expression system was previously employed for the functional analysis of TRF1 [van Steensel and de Lange, *Nature*, 385:740–743 (1997); Example 1, above]. Using this approach, a full length TRF2 protein and two truncated alleles in a doxycyclin-controlled fashion, were expressed. One allele (TRF2$^{\Delta B}$, having a nucleic acid sequence of SEQ ID NO:15, and an amino acid sequence of SEQ ID NO:16) lacked the N-terminal basic domain and the second allele (TRF2$^{\Delta B \Delta M}$, having a nucleic acid sequence of SEQ ID NO:13, and an amino acid sequence of SEQ ID NO:14) also lacked the C-terminal Myb domain (FIG. 12A). The two truncated proteins were endowed with an N-terminal FLAG tag allowing their detection with a FLAG-specific monoclonal antibody. For detection of full length TRF2, a polyclonal antibody directed against amino acids 16–42 was raised and affinity purified (antibody #508, see FIG. 12B). Clonal HTC75 cells transfected with each of the three TRF2 contructs were derived and shown to express appropriately-sized TRF2 polypeptides in an inducible manner with expression reaching plateau levels 1–2 days post-induction (FIG. 12B). Expression of the endogenous TRF2 protein was not affected by doxycyclin (FIG. 12B). Overexpression of full length TRF2 was also demonstrated by a gel-shift assay for the detection of TTAGGG repeat binding activity.

Consistent with previous experiments using epitope-tagged protein [Broccoli et al., *Nature Gen.*, 17:231–235 (1997): U.S. patent application Ser. No. 08/938,052 filed Sep. 26, 1997], endogenous TRF2 protein localized to telomeres throughout the cell cycle evident from the punctate pattern in interphase and the terminal localization of TRF2 signals in metaphase (FIGS. 13A and 13B). Furthermore, TRF2 co-localized with TRF1 in interphase nuclei. Transient overexpression of TRF2 did not significantly affect the localization of TRF1 at telomeres (FIGS. 13C and 13D). Similarly to full length TRF2, TRF2$^{\Delta B}$ accumulated at telomeres, consistent with previous evidence that the basic domain is not required for the localization of this protein to chromosome ends [Broccoli et al., *Nature Gen.*, 17:231–235 (1997); U.S. patent application Ser. No. 08/938,052 filed Sep. 26, 1997]. Cells expressing high levels of TRF2$^{\Delta B}$ showed diminished levels of the endogenous full length TRF2 on telomeres, evidencing a weak dominant interfering activity for this allele (FIG. 13F). The effect of TRF2$^{\Delta B}$ on the binding of endogenous TRF1 to telomeres was much less conspicuous than the effect on TRF2 and loss of TRF1 signal was only obvious in transiently transfected cells expressing extremely high levels of TRF2B (FIGS. 13G and 13H). Overexpression of TRF2$^{\Delta B}$ caused displacement of TRF2 but not TRF1 from telomeres indicating that the accumulation of the TRFs at telomeres involves more than their simple binding to TTAGGG repeats.

TRF1 binds to telomeric DNA as a homodimer, requiring two Myb domains for stable association with its target site in vitro and in vivo [Examples 1 and 2, above]. This architecture has allowed the design of a dominant negative allele of TRF1 containing the dimerization domain and the nuclear localization sequence (NLS), but lacking the Myb DNA binding domain [van Steensel and de Lange, Nature, 385:740–743 (1997); Example 1]. Analogously, expression of a A-TRF2 (TRF2$^{\Delta B \Delta M}$, FIG. 12A) resulted in a diffuse nuclear staining without evidence for accumulation of this protein at telomeres as expected from the absence of its DNA binding domain (FIGS. 13I and 13K). The expression of TRF2$^{\Delta B \Delta M}$ clearly interfered with the accumulation of the endogenous TRF2 protein at telomeres (FIG. 13J). While TRF2 could be readily demonstrated at telomeres in untransfected control cells, no or little TRF2 protein was observed at telomeric sites in cells expressing the TRF2$^{\Delta B \Delta M}$, attesting to the dominant negative activity of this A-TRF. Consistent with the earlier finding that the dimerization domains of TRF1 and TRF2 do not show strong interactions in vitro [Broccoli et al., Nature Gen., 17:231–235 (1997); U.S. patent application Ser. No. 08/938,052 filed Sep. 26, 1997], TRF2$^{\Delta B \Delta M}$ did not affect the accumulation of the endogenous TRF1 protein on telomeres (FIGS. 13K and 13L).

TRF2$^{\Delta B \Delta M}$ and TRF2$^{\Delta B}$ Induce a Growth Arrest in HTC75 Cells. While overexpression of full length TRF2 had no significant effect on the short term growth of HTC75 cells, induction of TRF2$^{\Delta B \Delta M}$ and TRF2$^{\Delta B}$ led to nearly complete inhibition of growth after approximately 4 days of culturing in the absence of doxycyclin (FIGS. 14A and 14B). This growth arrest was accompanied by induction of a β-galactosidase activity detectable at pH 6 (FIG. 14C), an indication that the cells were undergoing changes akin to senescence [Dirni et al., Proc. Natl. Acad. Sci. USA, 92:9363–9367 (1995)] although the staining of the arrested HTC75 cells was less intense than senescent primary human fibroblasts. In addition, the cells became enlarged, had a vacuolated cytoplasm, and often showed multiple small nuclei (FIG. 14C), all morphological phenomena associated with senescence of human cells [Hayflick and Moorhead, Exp. Cell Res., 25:585–621 (1961); Sherwood et al., Proc. Natl. Acad. Sci. USA, 85:9086–9090 (1988)]. Consistent with senescence, the arrest appeared irreversible since addition of doxycyclin to the media (to repress synthesis of the TRF2 mutant proteins) on day 12 did not alter the morphology or the proliferative arrest of the cells over a period of 9 days. A substantial proportion of the cells in each culture failed to show convincing morphological alteration and did not stain with β-galactosidase at pH 6.0 (FIGS. 14C–H). Most of these cells expressed very low levels of the TRF2 deletion derivatives. Collectively, the data suggested that TRF2$^{\Delta B}$ and TRF2$^{\Delta B \Delta M}$ induced a growth arrest with phenotypic characteristics of senescence.

The A-TRF, TRF2$^{\Delta B \Delta M}$, Induces Chromosome End Fusions. Microscopic analysis of DAPI-stained cells expressing TRF2$^{\Delta B \Delta M}$ revealed the frequent occurrence of anaphase bridges and lagging chromosomes (FIGS. 15A–C). This phenotype was not observed after induction of control cells not expressing TRF2 proteins or in cells induced for full length TRF2 or TRF2$^{\Delta B}$ (FIG. 15D). (Cells expressing TRF2$^{\Delta B}$ often contained small DAPI-positive fragments that were detectable in anaphase.)

The incidence of anaphase bridges and lagging chromosomes was quantitated in a total of 100 anaphase cells expressing TRF2$^{\Delta B \Delta M}$, uninduced control cells, and in a cell line expressing TRF2$^{\Delta B}$. At day 4 after induction of TRF2$^{\Delta B \Delta M}$, 40% of the cells had one or more aberrant chromosome (a bridge or a lagging chromosome) and the culture showed on average 0.7 fusions per anaphase cell (FIG. 15D). By contrast, the level of anaphase bridges and lagging chromosomes was low (<0.1 per cell) in the uninduced control cells and in a cell line expressing TRF$^{\Delta B}$ (FIG. 15D).

Chromosome end fusions induced by TRF2$^{\Delta B \Delta M}$ were also detected in metaphase spreads. Colcemid treated cells showed dicentrics fused at one or both chromatids, multiple fused chromosomes, and ring chromosomes (FIGS. 15E–G and Table 2). After induction for 6 days, 88% of the metaphases showed at least one fusion (Table 2). Several cells showed trains of 3 or 4 chromosomes (FIGS. 15E–G) and one cell showed as many as 30 individual fusion events. On average there were 2.4 fusion events per cell in cultures of the T4 clone when induced to express TRF2$^{\Delta B \Delta M}$ for 4 or 6 days. Uninduced T4 cells showed only 0.4 events per cell (Table 2). Similarly, a second cell line (T19) expressing TRF2$^{\Delta B \Delta M}$ showed an increase of the fusion frequency from 0.6 to 3.5 per cell upon induction of this dominant negative allele of TRF2. Cells with end-to-end fusions were rare in a control HTC75 cell line transfected with the vector (B27) or in cells expressing TRF2$^{\Delta B}$ (S13) (Table 2). In each case less then 0.3 fusions were observed per cell and fusions were only seen in 10–20% of the cells. Some of these fusion events may actually represent fortuitous juxtaposition of chromosome ends during spreading. Thus, expression of the A-TRF2, i.e., the dominant negative allele of TRF2 increases the frequency of telomere fusions by at least 10 fold. The relatively high frequency of telomere fusions in the cell lines T4 and T19 in the presence of doxycyclin may be due to leaky expression of the TRF2$^{\Delta B \Delta M}$ protein in a fraction of the cells.

TABLE 2

Induction of Chromosome End Fusions by Mutant TRF2 Proteins

| Cell line | Inducible Gene | Induction | Growth Period (days) | Number of Cells Examined | Fraction with Fusions | Fusions per Cell |
|---|---|---|---|---|---|---|
| B27 | — | − | 4 | 50 | 22% | 0.2 |
| T4 | TRF2(ΔBΔM) | − | 4 | 100 | 38% | 0.4 |
| T4 | TRF2(ΔBΔM) | + | 4 | 100 | 77% | 2.4 |
| T4 | TRF2(ΔBΔM) | + | 6 | 50 | 88% | 2.4 |
| T19 | TRF2(ΔBΔM) | − | 4 | 50 | 52% | 0.6 |
| T19 | TRF2(ΔBΔM) | + | 4 | 50 | 78% | 3.5 |
| S13 | TRF2(ΔB) | − | 4 | 50 | 10% | 0.1 |
| S13 | TRF2(ΔB) | + | 4 | 50 | 20% | 0.2 |

It should be stressed that the detection of chromosome end fusions in anaphase and metaphase cells likely represent an underestimate of the actual number of events. For instance, in metaphase cells the sister-chromatid fusions or fusions that have been followed by chromosome breakage are not scored for, and fusions are only detectable in anaphase cells when a bridge or lagging chromosome results. Thus, the quantitation of chromosome ends fusions probably reflects a minimal estimate of the actual fusion frequency in the cells.

Taken together the cytogenetic analysis demonstrate that the expression of the A-TRF2 results in the removal of TRF2 from telomeres and leads to loss of telomeric protection which is detected as end-to-end fusion in anaphase and metaphase chromosomes. It was unlikely that this phenotype was caused by the presence of excess TRF2 protein in the nucleoplasm because overexpression of full length TRF2 similarly resulted in the presence of TRF2 throughout the nucleus, yet induction of anaphase bridges was not noted in such cells.

Fused Chromosome Ends Contain Telomeric DNA. Fusion of chromosome ends has been documented in cells containing DNA damage and in cells that have depleted their reservoir of telomeric DNA. In those cases, telomeric DNA is usually not detectable at the site of fusion [Blasco et al., Cell., 91:25–34 (1997)]. Therefore it seemed reasonable that the fusions in response to $TRF2^{\Delta B\Delta M}$ were similarly correlated with loss of telomeric DNA from individual chromosome ends. Using a fluoresceine-labelled peptide nucleic acid (PNA) $[CCCTAA]_3$ probe specific for telomeric DNA, in situ hybridizations were carried out on metaphase spreads from cells displaying the chromosome ends fusions. The results in FIGS. 15E–G showed that telomeric DNA was preserved at the site of chromosome end fusion. In the majority of cases, the signal at the fused ends was substantially stronger than that found at free telomeres, consistent with the telomeric stretches of both fused chromosome ends remaining intact.

$TRF2^{\Delta B\Delta M}$ Induces Molecular Joining of Telomeric DNA Sequences. In order to establish whether the joining of telomeres in $TRF2^{\Delta B\Delta M}$-expressing cells depended on a proteinaceous bridge, evidence was sought for telomere fusion in naked genomic DNA. Detection of telomeric restriction fragments in genomic DNA from vector control cells and cells expressing full length TRF2 or $TRF2^{\Delta B}$ showed no change in telomere structure over the course of the induction period (FIGS. 16A and 16B). In direct contrast, cells induced for the A-TRF $TRF2^{\Delta B\Delta M}$ revealed a dramatic alteration in the pattern of HinfI/RsaI fragments detectable with TTAGGG repeat probes (FIG. 16B). A new class of longer restriction fragments first became apparent at 4 days post-induction (FIG. 16C) and this set of new fragments increased in intensity, but not in length over the course of the 9 day experiment. The new class of TTAGGG repeat fragments was observed in four independent clonal $TRF2^{\Delta B\Delta M}$ cell lines and in each case they migrated at a MW exactly twice (ratio of 2.0±0.2 (n=4)) that of the length of the original population of telomeric fragments. Quantitation of genomic blots indicated that up to 22% (average value 13.8±6.1% (n=4)) of the TTAGGG repeat signal was found in the larger class of hybridizing material at day 9 post-induction.

The fact that the $TRF2^{\Delta B\Delta M}$-induced new TTAGGG repeat fragments were twice the size of the original telomeres suggested that these molecules might represent the chromosome end fusions that were first detected by cytogenetic analysis of metaphase and anaphase cells. Such structures would be expected to be resistant to exonuclease Bal31 treatment of intact genomic DNA, whereas this exonuclease should readily attack the new class of larger TTAGGG repeat fragments if they represented elongated telomeres. Bal31 digestion of genomic DNA from T4 cells expressing $TRF2^{\Delta B\Delta M}$ indeed showed the resistance of the longer TTAGGG repeat fragments to this exonuclease (FIG. 16D). Quantitation of a second data set obtained with $TRF2^{\Delta B\Delta M}$-expressing T19 cells (FIG. 16E) showed that while the original telomeric loci were gradually shortened by Bal31, the $TRF2^{\Delta B\Delta M}$-induced longer fragments were not affected by the enzyme. This result indicated that the new class of TTAGGG repeat fragments did not represent elongated telomeres. Therefore these longer species are derived from the fused chromosome ends. Since the detection of fused ends in naked DNA indicates that the telomeres are held together by nucleic acid interactions, these end-joining events may be referred to as telomeric fusions.

Telomere fusions might be mediated by (Hoogsteen) base-pairing between the G-strand overhangs at human telomeres. Such a configuration was previously shown to temporarily link the termini of yeast chromosomes which carry long G-tails in late S-phase. Since this type of association was shown to be labile at 72–78° C., it was determined whether the fused human telomeres could be similarly resolved by treatment at that temperature. As shown in FIG. 16F, the fused telomeres derived from $TRF2^{\Delta B\Delta M}$-expressing cells are resistant to a temperature of 85° C. and only melt out at higher temperatures that also denature bulk DNA. This observation argues against the presence of G-G basepairing in the 3' overhang as the main mechanism by which telomere fusions occur. However, it is conceivable that the human G-tails form more stable G-G base paired structures than yeast telomere overhangs. The observation that the fused telomeric fragments are resistant to Bal31 nuclease constitutes further evidence against G-tail interactions in the fused telomeres. Since Bal31 readily cleaves single-stranded DNA, including very short regions of unpaired sequences such as those occurring due to pyrimidine dimers [Linn and Roberts, Nucleases, Cold Spring Harbor Laboratory, Cold Spring Harbor (1982)], this enzyme would be expected to digest single-stranded regions within G-G basepaired telomeric tails and resolve the joins. Therefore the telomere fusions appear to be the result of end-to-end ligations of one or both telomeric strands.

Telomeric Fusions Correlate with the Loss of G-strand Overhangs. Ligation of telomere termini would be unexpected if, as proposed by Makarov et al. [Cell, 88:657–666 (1997)], all or most human telomeres contain long regions of single-stranded TTAGGG repeat DNA. Makarov et al.[Cell, 88:657–666 (1997)] have developed a method for the quantitative detection of single-stranded TTAGGG repeats at the ends of human chromosomes. In this technique, HinfI/RsaI digested non-denatured genomic DNA is annealed to labelled $[CCCTAA]_4$ oligonucleotide and the indirectly labelled telomeric fragments are detected by autoradiography of size fractionated DNA. This technique evaluates the relative amount of unpaired single-stranded TTAGGG repeats in genomic DNA but does not discriminate between loss of signal due to shortening of the G-tails, complete disappearance of G-tails, or reduced detection of G-tails due to G-G base pairing in the overhangs.

Using the $[CCCTAA]_4$ probe on DNA derived from the control cell line B27, G-strand overhangs at the ends of wildtype telomeres were readily detected (FIG. 17). To validate the method, it was first verified that the probe did not anneal to DNA that was pretreated with Mung Bean nuclease and that annealing of a [TTAGGG]$_4$ probe did not result in a telomeric pattern. Comparing the amount of unpaired TTAGGG repeat DNA in cells grown in the presence and absence of doxycyclin, no alteration in the signal was noted in cells induced to express full length TRF2 or the TRF2$^{\Delta B}$ allele (FIG. 17A). Similarly, overexpression of TRF1 or a A-TRF1, i.e., a dominant negative allele of TRF1 [van Steensel and de Lange, Nature, 385:740–743 (1997); Example 1, above] did not affect the presence of unpaired TTAGGG repeats at telomere termini. In direct contrast, cells expressing the A-TRF2 (TRF2$^{\Delta B \Delta M}$) displayed a consistent reduction in the amount of detectable G-tail sequences and no signal was present at the position of the larger terminal fragments representing the fused telomeres (FIGS. 17A and 17B). Quantitation of the data on four clonal cell lines showed that induction of the A-TRF2, TRF2$^{\Delta B \Delta M}$, for 6–9 days resulted in a 40–60% decline in the total single-stranded TTAGCG repeat signals at chromosome ends (FIG. 17C). These data indicated that TRF2$^{\Delta B \Delta M}$ expression resulted in the loss of detectable single-stranded TTAGGG repeats at chromosome ends.

TRF2 does not Affect Telomerase Expression. The loss of G-tail sequences in TRF2$^{\Delta B \Delta M}$-expressing cells could arguably be explained if TRF2 is a positive regulator of telomerase expression. Therefore an examination was performed of the telomerase levels in extracts of cells induced for the three types of TRF2 protein used in this study and matching uninduced controls using the PCR-based TRAP assay [Kim et al., Science, 266:2011–2015 (1994)]. The result revealed similar levels of robust telomerase activity in each cell type regardless of the presence of doxycyclin in the media (FIG. 17D), demonstrating that the telomerase activity is not affected by TRF2 in this setting and that the loss of G-tail DNA occurs through some other mechanism.

Discussion

Telomere Protection by TRF2. The 3' extension of TTAGGG repeats at human chromosome ends are likely to serve as a binding site for single-strand specific telomeric proteins but the actual factors involved in this function are still elusive. A candidate activity that could cap the TTAGGG repeats has been identified in Xenopus extracts [Cardenas et al., Genes Dev., 7:883–894 (1993)], G-strand overhangs are bound by terminus specific proteins in ciliates [Gottschling and Zakian, Cell, 47:195–205 (1986); Price, Mol. Cell. Biol., 10:3241–3431 (1990)], and budding yeast telomeres are protected from degradation by Cdc13p [Garvik, Mol. Cell. Biol., 15:6128–6138 (1995)], a protein with G-tail binding activity in vitro [Lin and Zakian, Proc. Natl. Acad. Sci. USA, 93:13760–13765 (1996); Nugent et al., Science, 274:249–252 (1996)]. However, human homologs of these factors have not been identified yet. It should also be noted that G-rich telomeric repeats have the ability to form G-G (Hoogsteen) basepaired folded structures with several alternative conformations [reviewed by Henderson, In Telomeres, Cold Spring Harbor Press, Cold Spring Harbor (1995)] that could potentially contribute to the protection of chromosome ends.

The telomeric fusions are probably the consequence of processing of unmasked telomere termini by enzymes normally acting on broken DNA. A possible scenario is that loss of TRF2 from the chromosome ends leads to disappearance of the G-tail overhangs and activation of a DNA damage response by the denuded telomeres. A cell cycle arrest might ensue under these conditions and those cells that process the offending ends into fused telomeres may preferentially continue in the cell cycle leading to the observed metaphase abnormalities and anaphase bridges. The occurrence of fused telomeres in turn creates problems in mitosis due to the mechanical difficulties in segregating dicentric chromosomes which require either a break in the spindle or a break in a chromatid. Thus, the loss of telomeric protection may well lead to activation of checkpoints at several stages of the cell cycle.

Chromosome End Fusions in Cells with Critically Shortened Telomeres. Telomere associations have been observed by cytogenetic inspection of chromosome behavior in a number of different settings, including senescent primary cells, cells transformed with viral agents, and in a large variety of tumor specimen [reviewed in de Lange, In Telomeres, Cold Spring Harbor Press, Cold Spring Harbor (1995)]. Although this was not always established in these studies, data accumulated over the past decade suggest that in most cases where telomere associations were observed, the telomeres may have been fairly short. Indeed in studies that measured telomere length directly, there is a correlation between shortened telomeres and their association in metaphase [Counter et al., EMBO J., 11:1921–1929 (1992); Saltman et al., Chromosoma, 102:121–128 (1993)]. Although the present invention is not predicated on any particular inventory our observations on the behavior of chromosome ends after loss of the duplex telomeric DNA binding protein, TRF2, are consistent with a molecular mechanism underlying these telomere associations: When the telomeres reach a critical minimsal length their ability to recruit sufficient TRF2 is diminished and end-to-end fusions result.

Telomeres and Cellular Senescence. Expression of two mutant TRF2 polypeptides induced a growth arrest in the human fibrosarcoma cells used in this study. This arrest had several features consistent with the induction of senescence, including a specific cellular morphology, expression of a β-galactosidase activity correlated with senescence, and the irreversible nature of the arrest. Regardless of the exact nature of this phenotype, the results indicate that transformed human cells are rather sensitive to the status of their telomeres and that interference with telomere function inhibits their proliferation of malignant cells.

Two mechanisms for the induction of the observed growth arrest can be entertained at this stage. Since the growth arrest in HTC75 cells is accompanied by chromosomal abnormalities, one possibility is that the arrest is a response to DNA damage arising from the A-TRF2 activity at telomeres. The second possibility is that there exists a specific pathway allowing cells to evaluate the status of their telomeres. For instance, the presence of the basic N-terminus of TRF2 on telomeres may be required to suppress cellular senescence. Overexpression of a mutant protein lacking this domain would then be expected to induce arrest by displacing the endogenous TRF2. Similarly, the strong dominant negative activity of TRF2$^{\Delta B \Delta M}$ would result in telomeres lacking the basic N-terminal domain of TRF2 and cause an arrest signal. Such a mechanism would allow cells to monitor the length of their telomeres and initiate a growth arrest and senescence program in response to critical shortening of the telomeres.

Requirements for Telomere Formation in Human Cells. Transfection of TTAGGG repeats into human cells leads to efficient de novo formation of fully functional telomeres [Farr et al., Proc. Natl. Acad. Sci. USA, 88:7006–7010 (1991)]. Previously it was reported that there was an excellent correlation between the binding specificity of TRF1 and the cis-acting requirements for de novo telomere formation in human cells has been determined [Hanish et al., Proc. Natl. Acad. Sci. USA, 91:8861–8865 (1994)], indicating that the acquisition of TRF1 might be an essential step in telomere healing. However, the subsequent cloning of TRF2 revealed that this protein has the same sequence preference as TRF1 [Broccoli et al., *Nature Gen.*, 17:231–235 (1997); U.S. patent application Ser. No. 08/938,052 filed Sep. 26, 1997], raising the possibility that TRF2, rather than TRF1 is involved in the conversion of the transfected DNA into a fuictional telomere. The finding that TRF2 is important for the protection of chromosome ends now indicates an alternative scenario for de novo telomere formation in human cells. Acquisition of TRF2 may be one of the early steps as the transfected telomere seed enters the nucleus. According to the current data, TRF2 has the ability to protect the TTAGGG repeats from ligation to other DNA. As a result, the TRF2-bound end of the transfected linear plasmid may be prevented from undergoing the recombination reaction that normally leads to chromosome-internal integration of transfected DNA. Recombination of the other (non-telomeric) end of the transfected DNA with a resident chromosomal locus will then lead to the observed chromosome fragmentation. Telomerase subsequently elongates the telomere seed to form a fully functional telomere.

Mechanisms of Telomere Function. A general view of the logic underlying the function of human telomeres is now emerging (FIG. 18). Human telomerase has long been understood to maintain the terminal sequences of human chromosome ends and thus counter DNA attrition with cell divisions. The need for telomere length maintenance is particularly obvious in immortalized cells and in the germline. The current results reveal a second function for telomerase: in addition to balancing the terminal sequence loss that accompanies DNA replication, in the process of synthesizing arrays of TTAGGG repeats, telomerase also ensures the continued presence of TRF2 binding sites at chromosome ends. Since TRF2 is required to prevent telomere fusions, telomerase thus maintains the protective activity of telomeres by constantly replenishing TRF2 binding sites that are lost from telomere termini with DNA replication. This second function of telomerase critically depends on the sequence of the telomerase products is a key aspect of the mechanism of telomere function.

Addition of TTAGGG repeats to chromosome ends also ensures the binding of a second telomeric protein, TRF1, that acts as a negative regulator of telomerase, modulating the length of the TFAGGG repeats arrays at chromosome ends (Example 1). Thus, the telomerase-mediated maintenance of telomeric TTAGGG repeats secures a functional and regulated telomeric complex required for the integrity of chromosome ends.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. An isolated nucleic acid encoding an altered vertebrate telomere repeat binding factor 2 (A-TRF2), wherein said A-TRF2:
   (a) contains a vertebrate telomere repeat binding factor 2 (TRF2) dimerization domain; and
   (b) impedes a TRF2 from binding to its specific telomere repeat sequence by forming a heterodimer with the TRF2.

2. The isolated nucleic acid of claim 1 wherein the telomere repeat sequence is TTAGGG.

3. The isolated nucleic acid of claim 1 wherein the A-TRF2 is a fragment of the TRF2.

4. The isolated nucleic acid of claim 3 wherein the A-TRF2 has an amino acid sequence selected from the group consisting of SEQ ID NO:14, and SEQ ID NO:14 comprising a conservative amino acid substitution thereof.

5. The isolated nucleic acid of claim 4 having the nucleotide sequence of SEQ ID NO:13.

6. The isolated nucleic acid of claim 1 wherein the A-TRF2 further comprises a dysfunctional DNA binding domain.

7. The isolated nucleic acid of claim 6 wherein the dysfunctional DNA binding domain is dysfunctional due to a deletion in the amino acid sequence of the DNA binding domain.

8. The isolated nucleic acid of claim 6 wherein the dysfunctional DNA binding domain is dysfunctional due to a non-conservative amino acid change in the amino acid sequence of the DNA binding domain.

9. The isolated nucleic acid of claim 1 wherein the A-TRF2 further comprises a DNA binding domain that is not a TRF2 DNA binding domain.

10. The isolated nucleic acid of claim 1 which is DNA.

11. A cloning vector which comprises the nucleic acid of claim 10.

12. An expression vector which comprises the nucleic acid of claim 10 operatively associated with an expression control sequence.

13. A unicellular host transfected or transformed with the expression vector of claim 12.

14. The unicellular host of claim 13 that is a bacterium.

15. A mammalian cell transfected or transformed with the expression vector of claim 12.

16. An isolated nucleic acid encoding an A-TRF2 having an amino acid sequence selected from the group consisting of SEQ ID NO:16, and SEQ ID NO:16 comprising a conservative amino acid substitution thereof.

17. The isolated nucleic acid of claim 16 having the nucleotide sequence of SEQ ID NO:15.

18. The isolated nucleic acid of claim 1 wherein the A-TRF2 has an amino acid sequence selected from the group consisting of SEQ ID NO:23, and SEQ ID NO:23 comprising a conservative amino acid substitution thereof.

19. The isolated nucleic acid of claim 18 having the nucleotide sequence of SEQ ID NO:22.

20. A method of producing an A-TRF2 comprising culturing a cell containing an expression vector comprising a nucleic acid encoding the A-TRF2 under conditions that result in the A-TRF2 being expressed, wherein said A-TRF2:
   (a) contains a vertebrate TRF2 dimerization domain; and
   (b) impedes a TRF2 from binding to its specific telomere repeat sequence by forming a heterodimer with the TRF2.

21. The method of claim 20 further comprising the step of purifying the expressed A-TRF2.

* * * * *